(12) United States Patent
Thacher et al.

(10) Patent No.: US 9,657,053 B2
(45) Date of Patent: *May 23, 2017

(54) MODULATORS OF RETINOID-RELATED ORPHAN RECEPTOR GAMMA

(71) Applicant: ORPHAGEN PHARMACEUTICALS, San Diego, CA (US)

(72) Inventors: Scott Thacher, San Diego, CA (US); Xiaolin Li, San Diego, CA (US); Robert Babine, Carlsbad, CA (US); Bruno Tse, San Francisco, CA (US)

(73) Assignee: ORPHAGEN PHARMACEUTICALS, San Diego, CA (US)

( * ) Notice: Subject to any disclaimer, the term of this patent is extended or adjusted under 35 U.S.C. 154(b) by 350 days.

This patent is subject to a terminal disclaimer.

(21) Appl. No.: 13/766,076

(22) Filed: Feb. 13, 2013

(65) Prior Publication Data

US 2013/0150333 A1 Jun. 13, 2013

Related U.S. Application Data

(63) Continuation of application No. 13/114,616, filed on May 24, 2011, now Pat. No. 8,389,739, which is a continuation of application No. 11/867,637, filed on Oct. 4, 2007, now abandoned.

(60) Provisional application No. 60/849,903, filed on Oct. 5, 2006.

(51) Int. Cl.
| | |
|---|---|
| *A61K 31/58* | (2006.01) |
| *A01N 41/06* | (2006.01) |
| *A01N 37/00* | (2006.01) |
| *C07J 9/00* | (2006.01) |
| *C07C 311/21* | (2006.01) |
| *C07D 401/14* | (2006.01) |
| *C07J 21/00* | (2006.01) |
| *C07D 249/12* | (2006.01) |
| *C07D 493/10* | (2006.01) |

(52) U.S. Cl.
CPC ............ *C07J 9/005* (2013.01); *A61K 31/58* (2013.01); *C07C 311/21* (2013.01); *C07D 249/12* (2013.01); *C07D 401/14* (2013.01); *C07D 493/10* (2013.01); *C07J 9/00* (2013.01); *C07J 21/00* (2013.01)

(58) Field of Classification Search
None
See application file for complete search history.

(56) References Cited

U.S. PATENT DOCUMENTS

| 6,274,612 B1 | 8/2001 | Bryan |
| 2002/0108138 A1 | 8/2002 | Guenther et al. |
| 2003/0100542 A1 | 5/2003 | Barraclough et al. |
| 2003/0228607 A1 | 12/2003 | Wagner et al. |
| 2004/0156826 A1 | 8/2004 | Dangond et al. |
| 2004/0259948 A1 | 12/2004 | Tontonoz et al. |
| 2005/0009837 A1 | 1/2005 | Forman |
| 2005/0171084 A1 | 8/2005 | Cairns et al. |
| 2006/0134670 A1 | 6/2006 | Piu et al. |
| 2007/0154487 A1 | 7/2007 | Littman et al. |

FOREIGN PATENT DOCUMENTS

| WO | WO 00/24757 | 5/2000 |
| WO | WO 2004/028339 | 4/2004 |
| WO | WO 2006/007486 | 1/2006 |
| WO | WO 2006/055786 | 5/2006 |

OTHER PUBLICATIONS

Eberl Gérard et al.: An essential function for the nuclear receptor RORγ(t) in the generation of fetal lymphoid tissue inducer cells. *Nat Immunol* 5:64-73, 2004.
Eberl Gérard et al.: Thymic Origin of Intestinal αB T Cells Revealed by Fate Mapping of RORγt+ Cells. *Science* 305:248-51, 2004.
Harrington, et al.: Interleukin 17-producing CD4+ effector T cells develop via a lineage distinct from the T helper type 1 and 2 lineages. *Nat Immunol* 6:1123-32, 2005.
Hindinger C, et al.: Liver X Receptor Activation Decreases the Severity of Experimental Autoimmune Encephalomyelitis. *J Neuroscience Res* 84:1225-1234, 2006.
Hirose T., et al.: RORγ: the third member of ROR/RZR orphan receptor subfamily that is highly expressed in skeletal muscle. *Biochem Biophys Res Commun* 205:1976-83., 1994.
Huang et al., "Expert Opin Ther Targets," (2007) 11(6):737-743.
Ivanov et al.: The Orphan Nuclear Receptor Rorγt Directs the Differentiation Program of Proinflammatory IL-17+ T Helper Cells. *Cell* 126:1121-1133, 2006.
Ivanov, et al. Role of RORγ in development and homeostasis of the immune system. Nuclear Receptors: Orphan Brothers, Banff, Alberta, Keystone Symposia 2006.
Jetten A.M. et al: Retinoid-related orphan receptors (RORs): roles in cell survival, differentiation and disease. *Cell Death Differ* 9:1167-71, 2002.
Lipinksi et al., "Advanced Drug Delivery Review," (2001) 46:3-26.

(Continued)

*Primary Examiner* — Bong-Sook Baek

(74) *Attorney, Agent, or Firm* — Knobbe Martens Olson & Bear LLP

(57) ABSTRACT

Methods for modulating (inhibiting or stimulating) retinoid-related orphan receptor γ (RORγ) activity. This modulation has numerous effects, including inhibition of $T_H$-17 cell function and/or $T_H$-17 cell activity, and inhibition of restimulation of $T_H$-17 cells, which are beneficial to treatment of inflammation and autoimmune disorders. Stimulation of RORγ results in stimulation of $T_H$-17 cell function and/or activity which is beneficial for immune-enhancing compositions (e.g., vaccines).

28 Claims, 21 Drawing Sheets

(56) References Cited

OTHER PUBLICATIONS

Medvedev A.: Cloning of a cDNA encoding the murine orphan receptor RZR/RORγ and characterization of its response element. *Gene* 181:199-206, 1996.
Ortiz et al.: A new orphan receptor expressed in the thymus that can modulate retinoid and thyroid hormone signals. *Mol Endocrinol* 9:1679-91., 1995.
Park H., et al.: A distinct lineage of CD4 T cells regulates tissue inflammation by producing interleukin 17. *Nat Immunol* 6:1133-41, 2005.
Rademaann et al., *Science* (2000) 287(5460):1947-1948.
Steinman L.: A brief history of $T_h17$, the first major revision in the $T_h1/T_h2$ hypothesis of T cell-mediated tissue damage. *Nat Med* 13:139-45, 2007.
Stehlin-Gaon C., et al., "All-*trans* retinoic acid is a ligand for the orphan nuclear receptor RORβ," *Nature Structural Biology* vol. 10, No. 10, pp. 820-825, Oct. 2003.
Ziwei Huang et al., "*Pharmacol Ther*." (2000) 86(3):201-215.
Zuoming, Sun., et al: Requirement for RORγ in Thymocyte Survival and Lymphoid Organ Development. *Science* 288:2369-2373, 2000.
Liu, Jie: Pharmacology of oleanolic acid and ursolic acid, Journal of Ethnopharmacology, vol. 49:57-68 (1995).
Xu, Toa, et al.: Ursolic Acid Suppresses Interleukin-17 (IL-17) Production by Selectively Antagonizing the Function of RORγt Protein, Journal of Biological Chemistry, vol. 286:22707-22710 (2011).

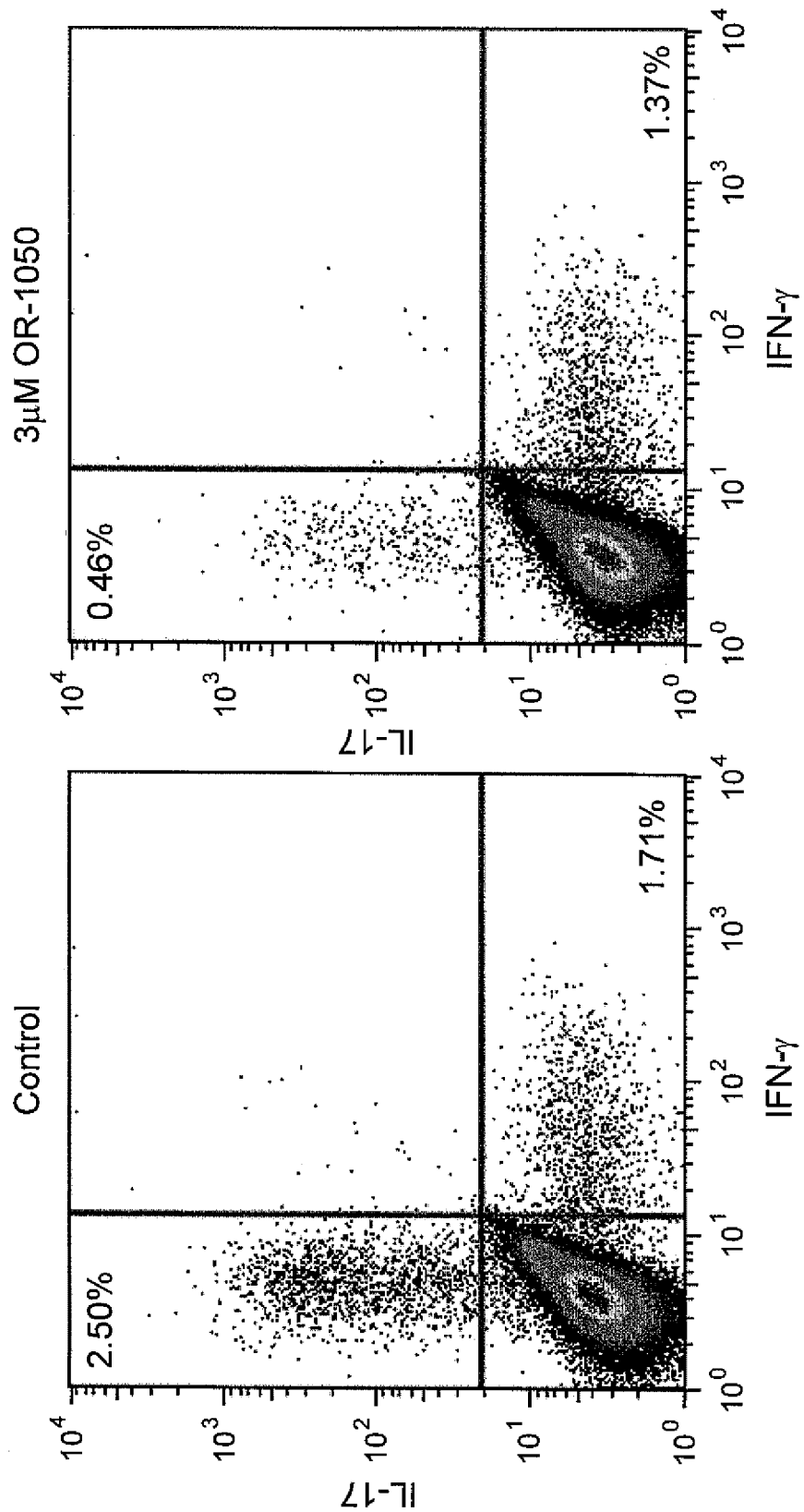

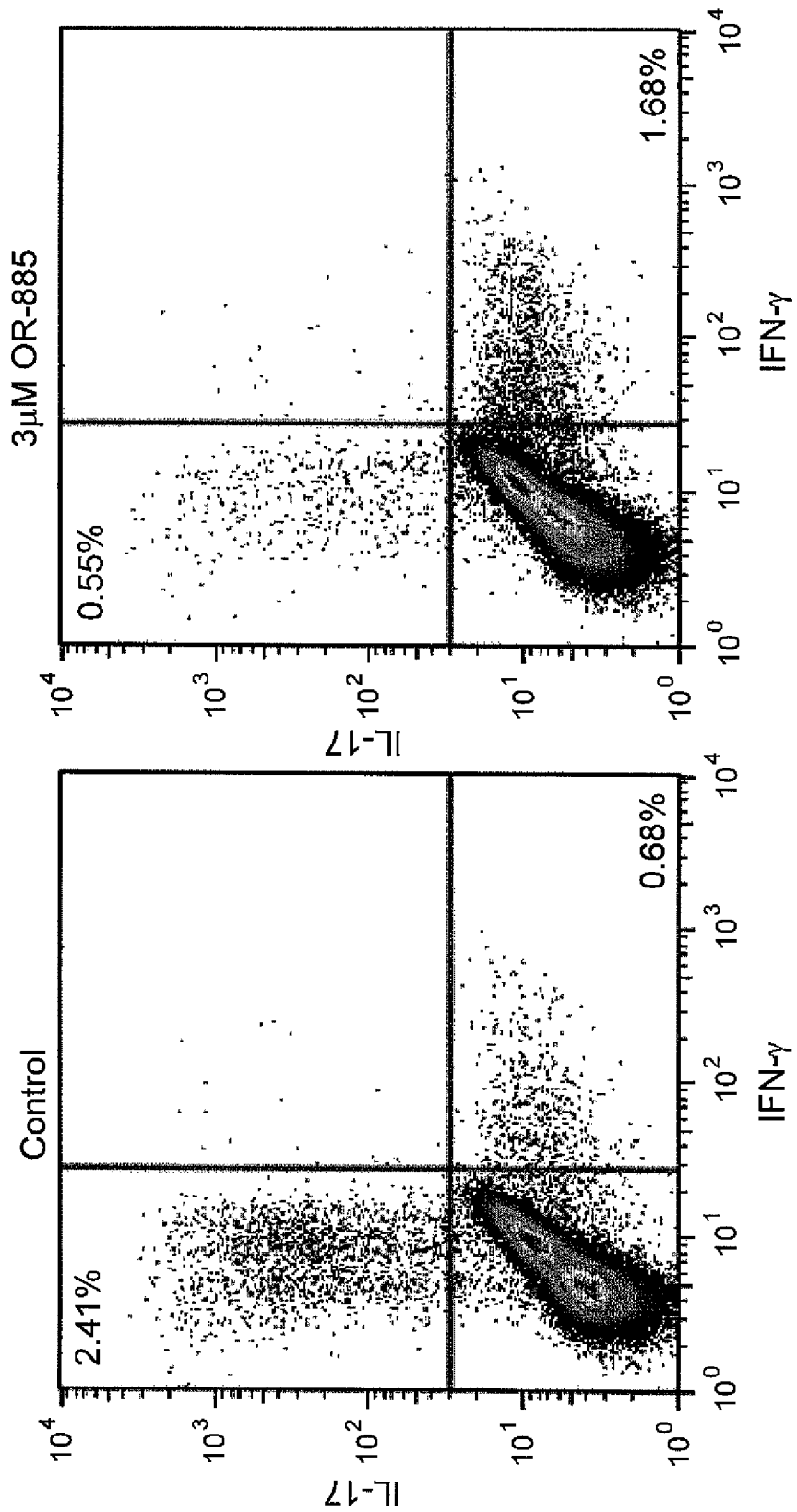

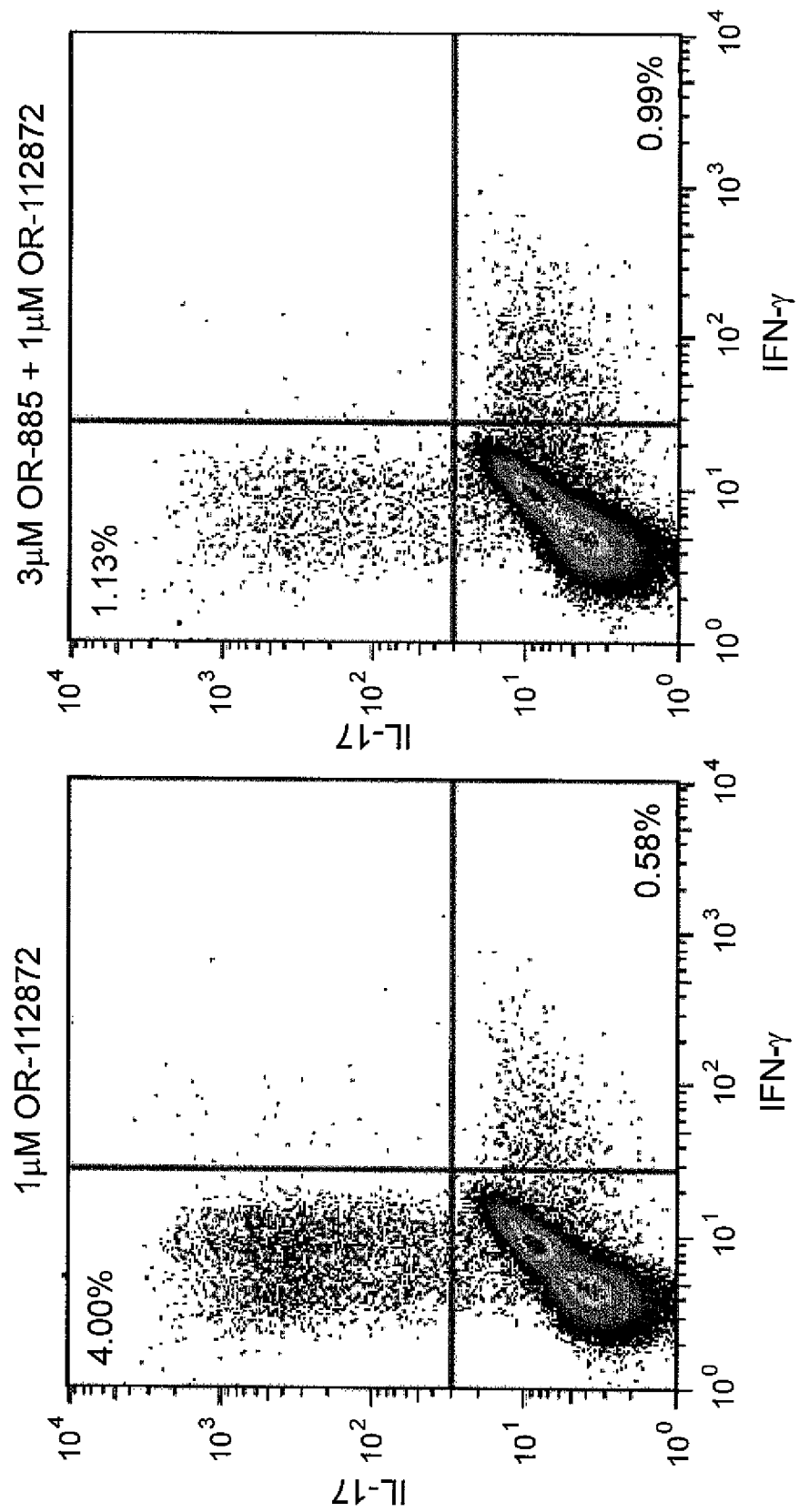

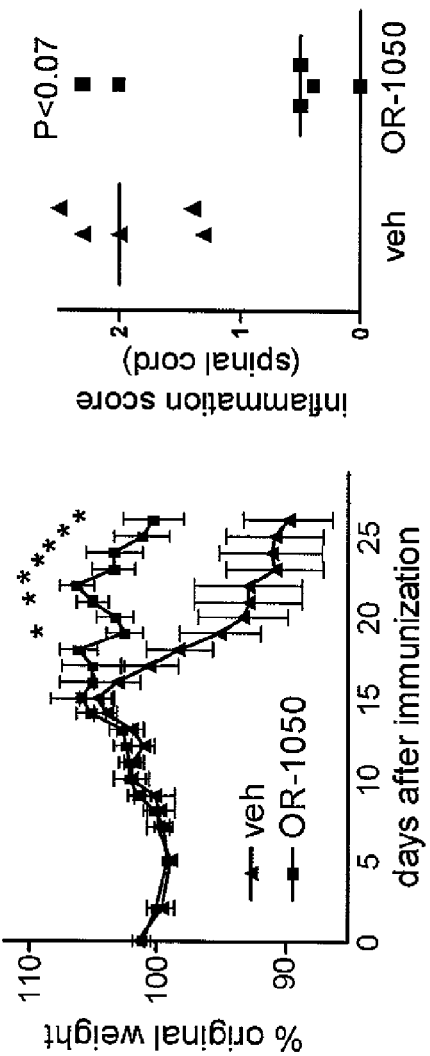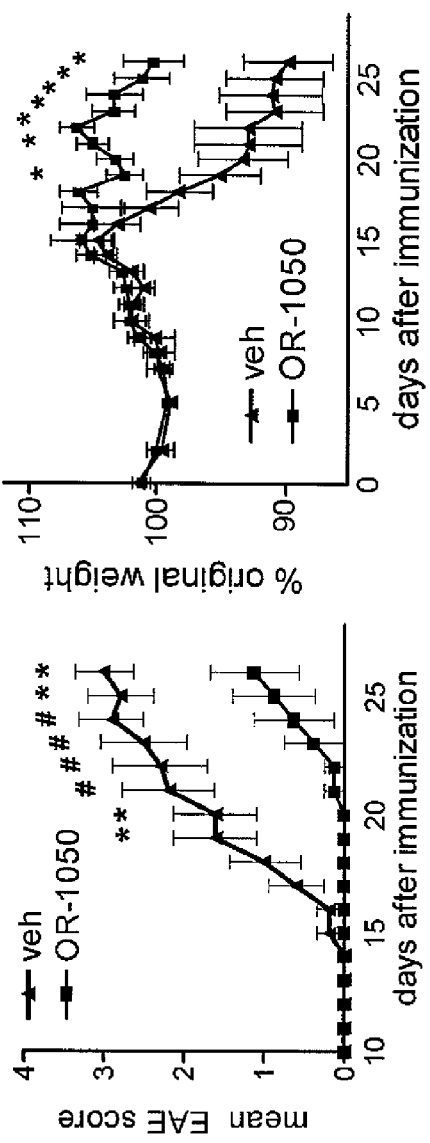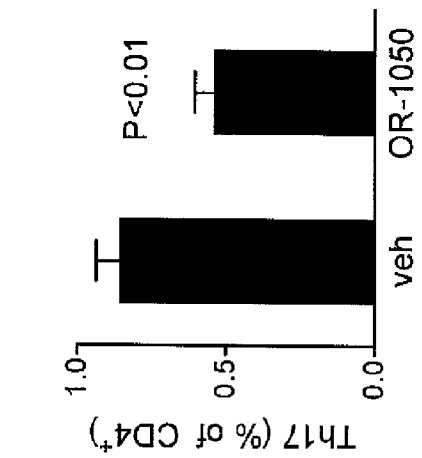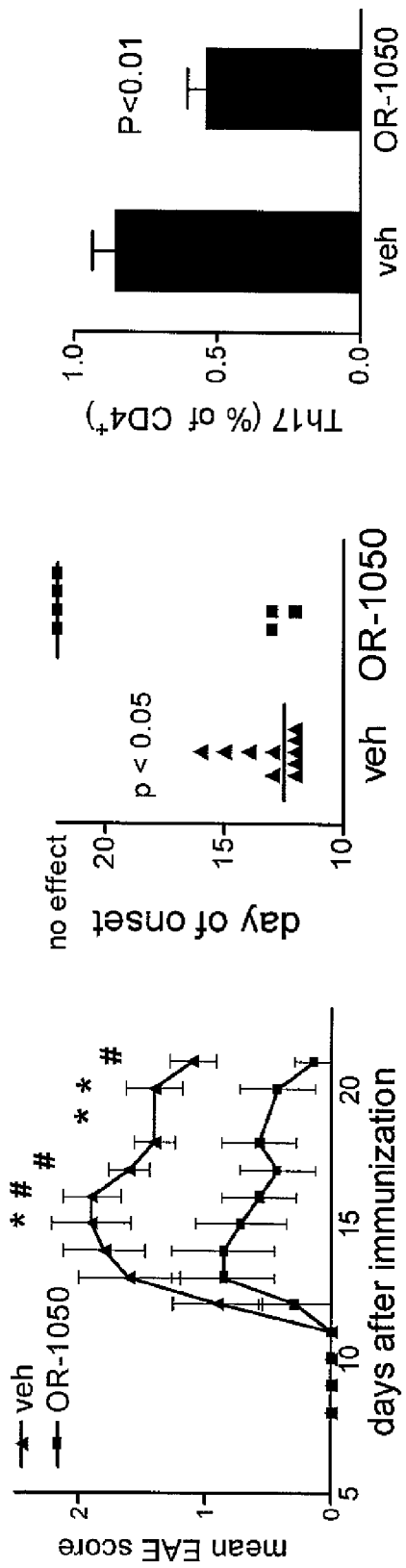
FIG. 11A  FIG. 11B  FIG. 11C
FIG. 11D  FIG. 11E  FIG. 11F

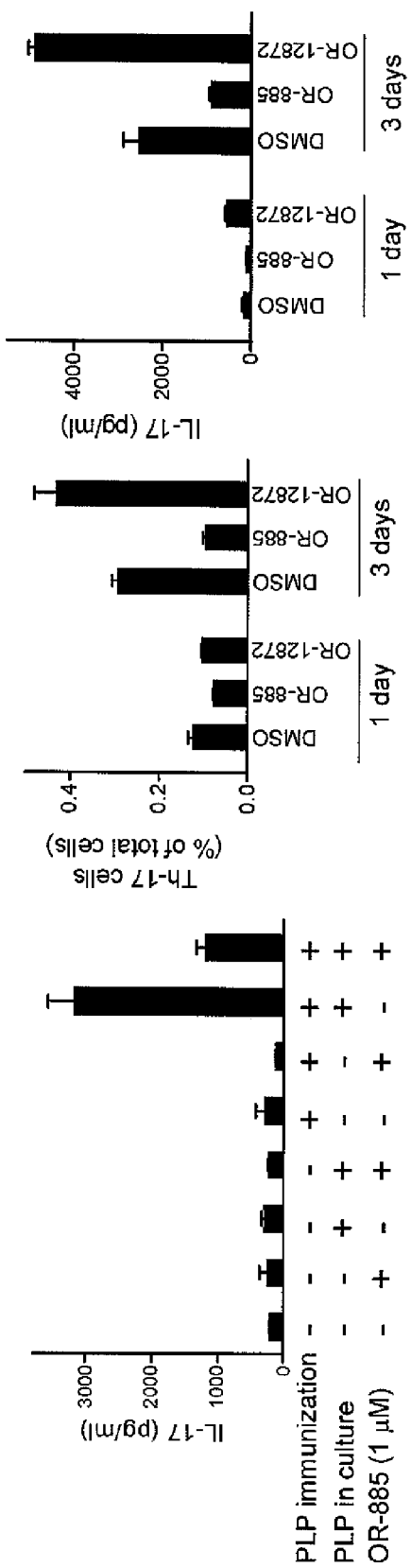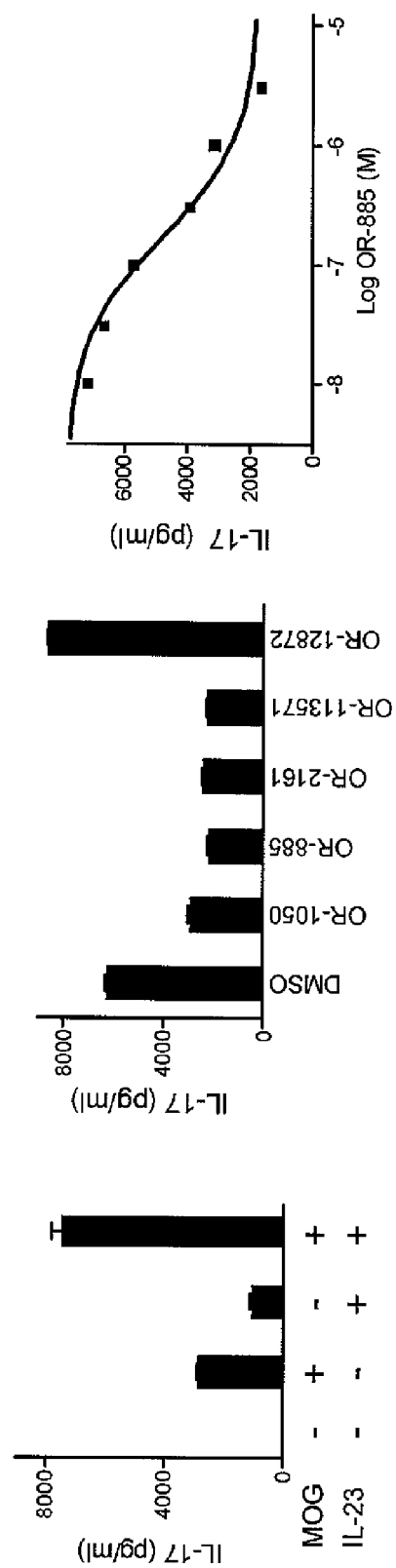

SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (3)...(3)
<223> OTHER INFORMATION: Xaa = any amino acid
<220> FEATURE:
<223> OTHER INFORMATION: Conserved peptide motif

<400> SEQUENCE: 1

Leu Xaa Xaa Leu Leu
 1               5

<210> SEQ ID NO 2
<211> LENGTH: 11
<212> TYPE: PRT
<213> ORGANISM: Homo sapiens

<400> SEQUENCE: 2

Arg Thr Val Leu Gln Leu Leu Leu Gly Asn Pro
 1               5                  10

<210> SEQ ID NO 3
<211> LENGTH: 15
<212> TYPE: PRT
<213> ORGANISM: Rattus norvegicus

<400> SEQUENCE: 3

Glu Arg Arg Thr Val Leu Gln Leu Leu Leu Gly Asn Ser Asn Lys
 1               5                  10                  15

<210> SEQ ID NO 4
<211> LENGTH: 15
<212> TYPE: PRT
<213> ORGANISM: Homo sapiens

<400> SEQUENCE: 4

Glu Arg Arg Thr Val Leu Gln Leu Leu Leu Gly Asn Pro Thr Lys
 1               5                  10                  15

<210> SEQ ID NO 5
<211> LENGTH: 15
<212> TYPE: PRT
<213> ORGANISM: Homo sapiens

<400> SEQUENCE: 5

Glu Arg Arg Thr Val Leu Gln Leu Val Val Gly Asn Pro Thr Lys
 1               5                  10                  15

<210> SEQ ID NO 6
<211> LENGTH: 15
<212> TYPE: PRT
<213> ORGANISM: Rattus norvegicus

<400> SEQUENCE: 6

Glu Arg Arg Thr Val Leu Gln Leu Val Val Gly Asn Ser Asn Lys
 1               5                  10                  15

<210> SEQ ID NO 7
<211> LENGTH: 444
<212> TYPE: DNA
<213> ORGANISM: Saccharomyces cerevisiae

<400> SEQUENCE: 7

```
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaaggtc tccgctgact agggcacatc tgacagaagt ggaatcaagg    180
ctagaaagac tggaacagct atttctactg atttttcctc gagaagacct tgacatgatt    240
ttgaaaatgg attctttaca ggatataaaa gcattgttaa caggattatt tgtacaagat    300
aatgtgaata agatgccgt cacagataga ttggcttcag tggagactga tatgcctcta    360
acattgagac agcatagaat aagtgcgaca tcatcatcgg aagagagtag taacaaaggt    420
caaagacagt tgactgtatc gccg                                            444
```

<210> SEQ ID NO 8
<211> LENGTH: 24
<212> TYPE: DNA
<213> ORGANISM: Artificial Sequence
<220> FEATURE:
<223> OTHER INFORMATION: Nucleic acid linker

<400> SEQUENCE: 8

```
ggatccgccc gggctggaat cgc                                             24
```

<210> SEQ ID NO 9
<211> LENGTH: 801
<212> TYPE: DNA
<213> ORGANISM: Mus musculus
<220> FEATURE:
<221> NAME/KEY: misc_feature
<222> LOCATION: 741
<223> OTHER INFORMATION: n = a, c, t, or g

<400> SEQUENCE: 9

```
attcccagtt tctgcagtgc cccagaggta ccatatgcct ctctgacaga catagagtac      60
ctggtacaga atgtctgcaa gtccttccga gagacatgcc agctgcgact ggaggacctt    120
ctacggcagc gcaccaacct cttttcacgg gaggaggtga ccagctacca gaggaagtca    180
atgtgggaga tgtgggagcg ctgtgcccac cacctcactg aggccattca gtatgtggtg    240
gagtttgcca gcggcttttc aggcttcatg gagctctgcc agaatgacca gatcatacta    300
ctgacagcag gagcaatgga agtcgtccta gtcagaatgt gcagggccta caatgccaac    360
aaccacacag tctttttttga aggcaaatac ggtggtgtgg agctgtttcg agccttgggc    420
tgcagcgagc tcatcagctc catatttgac ttttcccact tcctcagcgc cctgtgttt    480
tctgaggatg agattgccct ctacacggcc ctggttctca tcaatgccaa ccgtcctggg    540
ctccaagaga agaggagagt ggaacatctg caatacaatt tggaactggc tttccatcat    600
catctctgca agactcatcg acaaggcctc ctagccaagc tgccacccaa aggaaaactc    660
cggagcctgt gcagccaaca tgtggaaaag ctgcagatct ccagcacct ccaccccatc    720
gtggtccaag ccgccttccc nccactctat aaggaactct tcagcactga tgttgaatcc    780
cctgaggggc tgtcaaagtg a                                               801
```

<210> SEQ ID NO 10
<211> LENGTH: 148
<212> TYPE: PRT

<213> ORGANISM: Saccharomyces cerevisiae

<400> SEQUENCE: 10

```
Met Lys Leu Leu Ser Ser Ile Glu Gln Ala Cys Asp Ile Cys Arg Leu
1               5                   10                  15
Lys Lys Leu Lys Cys Ser Lys Glu Lys Pro Lys Cys Ala Lys Cys Leu
            20                  25                  30
Lys Asn Asn Trp Glu Cys Arg Tyr Ser Pro Lys Thr Lys Arg Ser Pro
        35                  40                  45
Leu Thr Arg Ala His Leu Thr Glu Val Glu Ser Arg Leu Glu Arg Leu
    50                  55                  60
Glu Gln Leu Phe Leu Leu Ile Phe Pro Arg Glu Asp Leu Asp Met Ile
65                  70                  75                  80
Leu Lys Met Asp Ser Leu Gln Asp Ile Lys Ala Leu Leu Thr Gly Leu
                85                  90                  95
Phe Val Gln Asp Asn Val Asn Lys Asp Ala Val Thr Asp Arg Leu Ala
            100                 105                 110
Ser Val Glu Thr Asp Met Pro Leu Thr Leu Arg Gln His Arg Ile Ser
        115                 120                 125
Ala Thr Ser Ser Glu Glu Ser Ser Asn Lys Gly Gln Arg Gln Leu
    130                 135                 140
Thr Val Ser Pro
145
```

<210> SEQ ID NO 11
<211> LENGTH: 8
<212> TYPE: PRT
<213> ORGANISM: Artificial Sequence
<220> FEATURE:
<223> OTHER INFORMATION: Peptide linker

<400> SEQUENCE: 11

```
Gly Ser Ala Arg Ala Gly Ile Arg
1               5
```

<210> SEQ ID NO 12
<211> LENGTH: 266
<212> TYPE: PRT
<213> ORGANISM: Mus musculus
<220> FEATURE:
<221> NAME/KEY: VARIANT
<222> LOCATION: 247
<223> OTHER INFORMATION: Xaa = any amino acid

<400> SEQUENCE: 12

```
Ile Pro Ser Phe Cys Ser Ala Pro Glu Val Pro Tyr Ala Ser Leu Thr
1               5                   10                  15
Asp Ile Glu Tyr Leu Val Gln Asn Val Cys Lys Ser Phe Arg Glu Thr
            20                  25                  30
Cys Gln Leu Arg Leu Glu Asp Leu Leu Arg Gln Arg Thr Asn Leu Phe
        35                  40                  45
Ser Arg Glu Glu Val Thr Ser Tyr Gln Arg Lys Ser Met Trp Glu Met
    50                  55                  60
Trp Glu Arg Cys Ala His His Leu Thr Glu Ala Ile Gln Tyr Val Val
65                  70                  75                  80
Glu Phe Ala Lys Arg Leu Ser Gly Phe Met Glu Leu Cys Gln Asn Asp
                85                  90                  95
Gln Ile Ile Leu Leu Thr Ala Gly Ala Met Glu Val Val Leu Val Arg
            100                 105                 110
```

```
Met Cys Arg Ala Tyr Asn Ala Asn Asn His Thr Val Phe Phe Glu Gly
            115                 120                 125
Lys Tyr Gly Gly Val Glu Leu Phe Arg Ala Leu Gly Cys Ser Glu Leu
        130                 135                 140
Ile Ser Ser Ile Phe Asp Phe Ser His Phe Leu Ser Ala Leu Cys Phe
145                 150                 155                 160
Ser Glu Asp Glu Ile Ala Leu Tyr Thr Ala Leu Val Leu Ile Asn Ala
                165                 170                 175
Asn Arg Pro Gly Leu Gln Glu Lys Arg Val Glu His Leu Gln Tyr
            180                 185                 190
Asn Leu Glu Leu Ala Phe His His His Leu Cys Lys Thr His Arg Gln
        195                 200                 205
Gly Leu Leu Ala Lys Leu Pro Pro Lys Gly Lys Leu Arg Ser Leu Cys
    210                 215                 220
Ser Gln His Val Glu Lys Leu Gln Ile Phe Gln His Leu His Pro Ile
225                 230                 235                 240
Val Val Gln Ala Ala Phe Xaa Pro Leu Tyr Lys Glu Leu Phe Ser Thr
                245                 250                 255
Asp Val Glu Ser Pro Glu Gly Leu Ser Lys
            260                 265
```

<210> SEQ ID NO 13
<211> LENGTH: 6
<212> TYPE: DNA
<213> ORGANISM: Artificial Sequence
<220> FEATURE:
<223> OTHER INFORMATION: Nucleic acid linker

<400> SEQUENCE: 13 ggatcc                                                              6

<210> SEQ ID NO 14
<211> LENGTH: 801
<212> TYPE: DNA
<213> ORGANISM: Homo sapiens

<400> SEQUENCE: 14
agccccagtt tccgcagcac accggaggca ccctatgcct ccctgacaga gatagagcac    60
ctggtgcaga gcgtctgcaa gtcctacagg agacatgcc agctgcggct ggaggacctg   120
ctgcggcagc gctccaacat cttctcccgg aggaagtga ctggctacca gaggaagtcc   180
atgtgggaga tgtgggaacg tgtgcccac cacctcaccg aggccattca gtacgtggtg   240
gagttcgcca agaggctctc aggctttatg gagctctgcc agaatgacca gattgtgctt   300
ctcaaagcag gagcaatgga agtggtgctg gttaggatgt gccgggccta caatgctgac   360
aaccgcacgg tctttttga aggcaaatac ggtggcatgg agctgttccg agccttgggc   420
tgcagcgagc tcatcagctc catctttgac ttctccccact ccctaagtgc cttgcacttt   480
tccgaggatg agattgccct ctacacagcc cttgttctca tcaatgccca tcggccaggg   540
ctccaagaga aaaggaaagt agaacagctg cagtacaatc tggagctggc ctttcatcat   600
catctctgca agactcatcg ccaaagcatc ctggcaaagc tgccacccaa ggggaagctt   660
cggagcctgt gtagccagca tgtggaaagg ctgcagatct ccagcacct ccaccccatc   720
gtggtccaag ccgctttccc tccactctac aaggagctct tcagcactga aaccgagtca   780
cctgtggggc tgtccaagtg a                                            801

<210> SEQ ID NO 15
<211> LENGTH: 2
<212> TYPE: PRT
<213> ORGANISM: Artificial Sequence
<220> FEATURE:
<223> OTHER INFORMATION: Peptide linker

<400> SEQUENCE: 15

Gly Ser
 1

<210> SEQ ID NO 16
<211> LENGTH: 266
<212> TYPE: PRT
<213> ORGANISM: Homo sapiens

<400> SEQUENCE: 16

Ser Pro Ser Phe Arg Ser Thr Pro Glu Ala Pro Tyr Ala Ser Leu Thr
 1               5                  10                  15

Glu Ile Glu His Leu Val Gln Ser Val Cys Lys Ser Tyr Arg Glu Thr
            20                  25                  30

Cys Gln Leu Arg Leu Glu Asp Leu Leu Arg Gln Arg Ser Asn Ile Phe
        35                  40                  45

Ser Arg Glu Glu Val Thr Gly Tyr Gln Arg Lys Ser Met Trp Glu Met
    50                  55                  60

Trp Glu Arg Cys Ala His His Leu Thr Glu Ala Ile Gln Tyr Val Val
65                  70                  75                  80

Glu Phe Ala Lys Arg Leu Ser Gly Phe Met Glu Leu Cys Gln Asn Asp
                85                  90                  95

Gln Ile Val Leu Leu Lys Ala Gly Ala Met Glu Val Val Leu Val Arg
            100                 105                 110

Met Cys Arg Ala Tyr Asn Ala Asp Asn Arg Thr Val Phe Phe Glu Gly
        115                 120                 125

Lys Tyr Gly Gly Met Glu Leu Phe Arg Ala Leu Gly Cys Ser Glu Leu
    130                 135                 140

Ile Ser Ser Ile Phe Asp Phe Ser His Ser Leu Ser Ala Leu His Phe
145                 150                 155                 160

Ser Glu Asp Glu Ile Ala Leu Tyr Thr Ala Leu Val Leu Ile Asn Ala
                165                 170                 175

His Arg Pro Gly Leu Gln Glu Lys Arg Lys Val Glu Gln Leu Gln Tyr
            180                 185                 190

Asn Leu Glu Leu Ala Phe His His His Leu Cys Lys Thr His Arg Gln
        195                 200                 205

Ser Ile Leu Ala Lys Leu Pro Pro Lys Gly Lys Leu Arg Ser Leu Cys
    210                 215                 220

Ser Gln His Val Glu Arg Leu Gln Ile Phe Gln His Leu His Pro Ile
225                 230                 235                 240

Val Val Gln Ala Ala Phe Pro Pro Leu Tyr Lys Glu Leu Phe Ser Thr
                245                 250                 255

Glu Thr Glu Ser Pro Val Gly Leu Ser Lys
            260                 265

<210> SEQ ID NO 17
<211> LENGTH: 660
<212> TYPE: DNA
<213> ORGANISM: Sacchraomyces cerevisiae

<400> SEQUENCE: 17

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360 gatttttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga aatccagcaa gtatatagca    600
tggcctttgc agggctggca agccacgttt ggtggtggcg accatcctcc aaaatcggat    660
```

<210> SEQ ID NO 18
<211> LENGTH: 212
<212> TYPE: DNA
<213> ORGANISM: Artificial Sequence
<220> FEATURE:
<223> OTHER INFORMATION: Nucleic acid linker

<400> SEQUENCE: 18

```
ggttcaacta gtggttctgg tcatcaccat caccatcact ccgcgggtct ggtgccacgc      60
ggtagtactg caattggtat gaaagaaacc gctgctgcta aattcgaacg ccagcacctg    120
gacagcccag atctgggtac cggtggtggc tccggtgatg acgacgacaa gagtcccatg    180
ggatatcggg gatccgcccg ggctggaatt cg                                 212
```

<210> SEQ ID NO 19
<211> LENGTH: 21
<212> TYPE: PRT
<213> ORGANISM: Artificial Sequence
<220> FEATURE:
<223> OTHER INFORMATION: Synthetic peptide

<400> SEQUENCE: 19

Met Glu Val Gly Trp Tyr Arg Ser Pro Phe Ser Arg Val Val His Leu
1               5                   10                  15
Tyr Arg Asn Gly Lys
            20

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

His Ser Leu Gly Lys Trp Leu Gly His Pro Asp Lys Phe
1               5                   10

MODULATORS OF RETINOID-RELATED ORPHAN RECEPTOR GAMMA

RELATED APPLICATIONS

This application is a continuation of U.S. application Ser. No. 13/114,616, filed May 24, 2011, which is a continuation of U.S. application Ser. No. 11/867,637, filed Oct. 4, 2007, which claims priority under 35 U.S.C. §119(e) to U.S. Provisional Application No. 60/849,903, filed Oct. 5, 2006. The contents of these applications are incorporated herein by reference in their entireties.

STATEMENT REGARDING FEDERALLY SPONSORED RESEARCH

This invention was made with government support under Grant Numbers 1 R43AI060447-01, 1 R03NS 050879-01, 1 R43DK071461-01, 1 R43 MH075461-01, 1 R43 NS 059219-01, 1 R43CA099875-01A1, and 1 R43AR055427-01 from the National Institutes of Health. The government has certain rights in the invention.

REFERENCE TO SEQUENCE LISTING

The present application is being filed along with a sequence listing in electronic format. The sequence listing is provided as a file entitled ORPH.001C2.txt, created Feb. 13, 2013 which is 12 KB in size. The information in the electronic format of the sequence listing is incorporated herein by reference in its entirety.

FIELD OF THE INVENTION

The present invention relates to methods for modulating (inhibiting or stimulating) retinoid-related orphan receptor γ (RORγ) activity. This modulation has numerous effects, including inhibition of $T_H$-17 cell function and/or $T_H$-17 cell activity, and inhibition of re-stimulation of $T_H$-17 cells, which are beneficial to treatment of inflammation and autoimmune disorders. In contrast, stimulation of RORγ results in stimulation of $T_H$-17 cell function and/or activity which is beneficial for immune-enhancing compositions (e.g., vaccines). More specifically, the present invention relates to methods for inhibiting differentiation of T cells into $T_H$-17 cells, or inhibiting the activity of $T_H$-17 cells and other T cells that express IL-17, by contacting a population of T cells that may include $T_H$-17 cells, with an antagonist of RORγ.

BACKGROUND OF THE INVENTION

Many forms of serious human disease result from an autoimmune attack on the body. Many forms of autoimmune disease, such as rheumatoid arthritis, multiple sclerosis, psoriasis, and Crohn's disease, are particularly difficult to treat. An activated CD4$^+$ T cell that releases interleukin-17 (IL-17), a powerful pro-inflammatory cytokine (Aggarwal, Ghilardi et al. 2003), and is referred to as a $T_H$-17 cell (Bettelli, Carrier et al. 2006; Mangan, Harrington et al. 2006; Veldhoen, Hocking et al. 2006), may be a significant pathogenic factor in autoimmune disease, based on observations that patients have high levels of IL-17 expression in target tissues. For example, the level of IL-17 mRNA was found to be elevated in brain autopsy tissue from patients with MS compared with controls, and the number of IL-17 positive mononuclear cells was also increased in the cerebrospinal fluid of affected patients (Matusevicius, Kivisakk et al. 1999; Lock, Hermans et al. 2002; Vaknin-Dembinsky, Balashov et al. 2006). Rheumatoid arthritis (RA) also appears to involve a T cell-mediated autoimmune reaction. The level of IL-17 mRNA in synovial fluid of rheumatoid arthritis patients is predictive of disease progression (Kirkham, Lassere et al. 2006). Furthermore, $T_H$-17 cells have been isolated from intestinal biopsies of patients with Crohn's Disease (Annunziato, Cosmi et al. 2007), and their frequencies are elevated in comparison to T cells isolated from normal intestine or peripheral blood. In disease tissue of psoriasis patients, levels of IL-22, another proinflammatory cytokine produced by $T_H$-17 cells, are elevated (Zheng, Danilenko et al. 2007).

$T_H$-17 cells, also referred to as IL-17$^+$CD4$^+$ T or $T_{IL-17}$ cells, have only been recently characterized and are distinct from the $T_H$1 and $T_H$2 lineages of CD4$^+$ effector T cells. The relationship of $T_H$-17 cells to the $T_H$1 and $T_H$2 lineages is diagrammed in FIGS. 1. $T_H$1 and $T_H$2-derived cytokines (such as IFN-γ and IL-4) block $T_H$-17 formation (FIG. 1) and targeted deletion of some transcription factors considered to be central for maintenance of the $T_H$1 and $T_H$2 phenotype have no major effect on $T_H$-17 differentiation (Harrington, Hatton et al. 2005; Park, Li et al. 2005). IL-23 expression in mouse is required for induction of T cell-derived IL-17, and in culture IL-23 seems to act as a survival factor for pre-existing $T_H$-17 cells but does not stimulate $T_H$-17 formation from naïve CD4$^+$ T cells. Instead, the combination of TGFβ and IL-6 is required to stimulate the formation of $T_H$-17 cells from naive mouse CD4$^+$ T cells, and there is genetic evidence in mouse for the involvement of IL-6 and TGFβ in $T_H$-17 formation in vivo (Bettelli, Carrier et al. 2006; Mangan, Harrington et al. 2006; Veldhoen, Hocking et al. 2006). The cytokine requirements for $T_H$-17 differentiation in human are somewhat different that in mouse but the $T_H$-17 phenotype is similar, including expression of IL-17, IL-22, and RORγ (Annunziato, Cosmi et al. 2007; Kebir, Kreymborg et al. 2007).

The older view that autoreactive CD4$^+$ $T_H$1 cells are a prime cause for the development or progression of MS and other forms of autoimmune disease has been challenged (Steinman 2007) by recent results from rodent models showing that mice with a targeted deletion in the p35 subunit of IL-12, which is required for the formation of $T_H$1 cells, are still highly susceptible to the induction of experimental autoimmune encephalomyelitis (EAE) after immunization with myelin antigens (Becher, Durell et al. 2002; Gran, Zhang et al. 2002). In contrast, the knockout of either p19, the unique subunit of the cytokine IL-23, or p40, a common subunit of the two cytokines IL-12 and IL-23, create mice that are resistant to the induction of EAE (Cua, Sherlock et al. 2003; Langrish, Chen et al. 2005).

In addition to EAE, development of disease in a mouse model of rheumatoid arthritis, collagen-induced arthritis (Courtenay, Dallman et al. 1980), is also dependent on IL-23 function and is correlated with an increased level of $T_H$-17 cell activity, such as release of IL-17 in affected tissues (Murphy, Langrish et al. 2003; Sato, Suematsu et al. 2006). Inhibition of IL-17 may be a viable alternative to inhibition of TNFα in treatment of RA (Lubberts, Koenders et al. 2005). Further, IL-23 expression is required for induction of IBD in mouse, and $T_H$-17 cells appear to be an important downstream mediator of IL-23 effect in this model (Yen, Cheung et al. 2006). Disease progression in EAE models is partially suppressed in IL-17$^{-/-}$ mice or after treatment with anti-IL-17 antibodies (Iwakura and Ishigame 2006). IL-17$^{-/-}$ mice also show reduced incidence and severity in a collagen-induced arthritis (CIA) model for rheumatoid arthritis and IL-17 antibodies have been shown to attenuate development of intestinal inflammation in rodent models of IBD (Nakae, Nambu et al. 2003; Yen, Cheung et al. 2006). Further, purified autoreactive $T_H$-17 cells strongly induce encephalomyelitis when transferred to naive mice, leading to more dramatic disease manifestation compared to disease induction by $T_H1CD4^+$ T cells (Langrish, Chen et al. 2005; Komiyama, Nakae et al. 2006). The IL-27 receptor is prominently expressed in $T_H$-17 cells and the action of IL-27 as an inhibitor of murine EAE is correlated to reduced $T_H$-17 cell number in the animal (Batten, Li et al. 2006; Stumhofer, Laurence et al. 2006). Therefore, the activity of murine $T_H$-17 cells is well correlated to disease.

Inhibition of the human equivalent of the mouse $T_H$-17 cell is a highly desirable target for new therapeutic agents to treat autoimmune disease. Recent findings implicate $T_H$-17 cells in the pathogenesis of Crohn's disease and more generally inflammatory bowel disease (IBD). Antibody to the common subunit of IL-23 and IL-12, p40, is safe and may be clinically effective in treatment of Crohn's disease (Mannon, Fuss et al. 2004). A recent Phase 2 clinical trial also shows that anti-p40 is highly effective in the treatment of psoriasis (Krueger, Langley et al. 2007). The identification of $T_H$-17 cells has not only provided insight into autoimmune pathogenesis, it has also revealed a major pathway of adaptive immunity for extracellular microbes (Mangan, Harrington et al. 2006; Annunziato, Cosmi et al. 2007). Stimulation of $T_H$-17 differentiation, function and cytokine release therefore has the potential to enhance protective immunity by increasing T cell reactivity to pathogenic organisms and other targets, such as cancer-associated antigens.

Structure and Function of RORγ

RORγ (NR1F3), a ligand-regulated nuclear transcription factor from the steroid/retinoid/thyroid family (Jetten, Kurebayashi et al. 2001), has been shown to be essential for CD4$^+$ $T_H$-17 development and/or function. RORγ participates in and is required for the development of $T_H$-17 cells. $T_H$-17 cells are absent from genetically-engineered mice that fail to express a specific splicing isoform of RORγ, RORγt (Ivanov, McKenzie et al. 2006; Littman and Eberl 2006). Furthermore, an RORγt-GFP transgene that expresses GFP from the RORγt promoter is expressed in CD4$^+$IL-17$^+$ T cells from the lamina propria of the gut and other tissues. In cell culture, transfection of RORγt into naïve murine CD4$^+$ T cells induces differentiation of these cells into IL-17 expressing T cells even in the absence of the inducing cytokines IL-6 and TGFβ. The data suggest that the transcriptional activity of RORγt is of major importance to $T_H$-17 cell differentiation and function (Ivanov, McKenzie et al. 2006). RORγt expression is induced in the presence of TGFβ and IL-6 or by TGFβ and IL-21, an autocrine cytokine released from developing $T_H$-17 cells in response to IL-6 (Ivanov, McKenzie et al. 2006; Korn, Bettelli et al. 2007; Nurieva, Yang et al. 2007; Zhou, Ivanov et al. 2007).

The expression of RORγ follows a similar pattern in human as in mouse T cells: RORγ is more highly expressed in IL-17 or IL-17/IFNγ expressing CD4$^+$ T cells (Th-17) than in CD4$^+$ T cells that express IFNγ alone (Th-1) (Acosta-Rodriguez, Napolitani et al. 2007; Acosta-Rodriguez, Rivino et al. 2007; Annunziato, Cosmi et al. 2007; Wilson, Boniface et al. 2007). Finally, it has been reported that other murine T cell types express RORγt, including γδTCR$^+$ cells, CD8$^+$ T cells, and iNKT cells (Ivanov, McKenzie et al. 2006; Ivanov and Littman 2007). Since these cells are also express IL-17, it is possible that RORγt is required for the differentiation of the IL-17$^+$ subpopulations of several other types of T cells.

Finally, in the absence of RORγt, mice are much less susceptible to the induction of EAE (Ivanov, McKenzie et al. 2006). These studies were carried out in immunodeficient mice. RORγt$^{-/-}$ mice lack lymph notes, and although they are resistant to the development of EAE, a further study was carried out by adoptive transfer of RORγt wild type or RORγt$^{-/-}$ bone marrow to immunodeficient mice. While transfer of normal bone marrow rendered the mice sensitive to the induction of EAE by peptide immunization, the RORγt$^{-/-}$ transfectants were substantially resistant (Ivanov, McKenzie et al. 2006). These data suggest that RORγt mediated regulation of T cell differentiation is involved in the development of autoimmune disease.

RORγ Structure. RORγ, like other members of the nuclear receptor family, has a bipartite structure with two major functional domains, a DNA binding domain (DBD) and a ligand binding domain (LBD, see FIG. 2) (Medvedev, Yan et al. 1996). Ligand-regulated transcription of the nuclear receptors is mediated through the LBD, which has been crystallized for many receptors (Li, Lambert et al. 2003), including RORα and RORβ, the receptors most closely related to RORγ. The RORγ LBD is predicted to have a binding pocket similar to RORα and RORβ (Stehlin, Wurtz et al. 2001; Kallen, Schlaeppi et al. 2004). The retinoic acid receptors (RARα, RARβ, and RARγ) are more distantly related and appear not to have a functional overlap with the RORs (Jetten, Kurebayashi et al. 2001).

The nuclear receptor LBD recruits transcriptional coregulators (FIG. 2) in response to small molecule compounds (Li, Lambert et al. 2003; Savkur and Burris 2004). These coregulatory proteins act as sensors for the conformational state of the ligand-bound complex and in turn regulate the recruitment of transcriptional factors to chromatin adjacent to the receptor. Short peptide domains of the coregulatory proteins required for interaction with the nuclear receptor contain the conserved sequence LXXLL (SEQ ID NO: 1), and synthetic peptide recruitment assays based on this motif are widely used to monitor the binding of agonists and antagonists to the nuclear receptor LBD (Lee, Elwood et al. 2002; Savkur and Burris 2004), including for an assay described herein for RORγ.

Functional Studies of RORγ. Recognition of specific DNA motifs by the nuclear receptor DBD determines specificity for gene transcription; however, little is known about specific gene targets for RORγ, and the major findings on RORγ function have been derived from studies of gene-targeted mice (Kurebayashi, Ueda et al. 2000; Sun, Unutmaz et al. 2000; Eberl and Littman 2004; Eberl, Marmon et al. 2004). RORγ has two splicing isoforms, RORγ and RORγt (He, Deftos et al. 1998). RORγt differs from RORγ by a truncation of 21 amino acids at the N-terminal and is the isoform specifically expressed in thymus, lymph node precursors, and $T_H$-17 cells (Eberl and Littman 2004; Eberl, Marmon et al. 2004; Ivanov, McKenzie et al. 2006; Littman and Eberl 2006), the major tissues affected in knockout studies of RORγ. The significance of the N-terminal deletion of RORγ is not known, but it is unlikely to affect ligand specificity or LBD function, which is encoded at the receptor's C-terminal and is identical in the two splicing isoforms.

In addition to its requirement for $T_H$-17 differentiation, RORγ has other discrete functions in the immune system. In its absence, the survival of the major subtype of developing T lymphocytes, the CD4$^+$CD8$^+$ double positive (DP) thymocytes, is reduced (Kurebayashi, Ueda et al. 2000; Sun, Unutmaz et al. 2000), and the embryonic formation of lymph nodes and Peyer's patches is blocked (Eberl, Marmon et al. 2004). RORγt is an early marker for the embryonic formation of lymphoid tissue inducer or LTi cells. LTi cells are involved in lymph node and Peyer's patch formation during embryogenesis (Eberl, Marmon et al. 2004). After birth, an LTi-like cell participates in formation of intermediate lymphoid follicles (ILFs) of the gut. These lymphoid structures appear to participate in the gut immune response (Eberl and Littman 2004). RORγ is also expressed in liver, muscle, and fat (Jetten, Kurebayashi et al. 2001; Fu, Sun et al. 2005). A recent study of RORγ$^{-/-}$ mice also suggests that the receptor has some regulatory effects on Phase 1 and Phase 2 detoxification enzymes (Kang, Angers et al. 2007).

Clinical Significance. Three major points of action of RORγ in the immune system have been identified in gene knockout studies; T cells, including the $T_H$-17 cell, lymph node formation, and survival of DP thymocytes. Of these, regulation of IL-17$^+$ T cell function, including $T_H$-17 differentiation, appears to be most relevant to human therapeutics. Not only is the receptor absolutely required for $T_H$-17 differentiation, but the supply of pathogenic $T_H$-17 cells must be constantly replenished since they are destroyed in target tissue (Gold, Linington et al. 2006). Inhibition of new $T_H$-17 formation will therefore have important benefits. RORγ is expressed in human memory $T_H$-17 cells (Acosta-Rodriguez, Rivino et al. 2007; Annunziato, Cosmi et al. 2007), and data presented herein shows that RORγ antagonists block IL-17 expression in human peripheral blood mononuclear cells (PBMCs). The primary source of IL-17 in PBMCs has been reported to be memory T cells (Shin, Benbernou et al. 1999). Finally, RORγ enhances, but is not absolutely required for, the survival of the major developing T cell type of the thymus, the DP thymocyte. In the knockout animal, there is no evidence of immunodeficiency although splenic and peripheral frequencies of some immune cell types are changed. However, there is a much higher rate of apoptosis among thymocytes and thymocyte number is reduced (Kurebayashi, Ueda et al. 2000; Zhang, Guo et al. 2003). The thymus of an adult has already atrophied to a considerable degree and can be reversibly suppressed by many forms of pharmacological treatment, including exposure to steroids (Haynes, Markert et al. 2000). These data suggest that secondary effects of an RORγ antagonist on thymic function in human may not be clinically significant.

Prior to 1990, no drugs to treat MS were available. In the last 15 years, several treatment options have emerged, primarily various forms of INFβ (Avonex, Rebif, Betaseron), Glatiramer acetate (Copaxone) and the chemotherapeutic drug mitoxantrone (Novantrone) (Rolak 2003). INFβ and Glatiramer acetate both appear to inhibit T cell activation and both drugs reduce the number of attacks in relapsing-remitting MS but have little effect in the progressive phase of the disease (Dhib-Jalbut 2002; Rolak 2003). The long-term benefits of these drugs are unclear. Mitroxantrone appears to retard progression and delay disability in secondary progressive MS. However, toxicity of this drug is very limiting and Mitroxantrone is considered a short-term treatment option. More recently, a humanized antibody to α4β1 integrin (NATALIZUMAB, Tysabri) has been approved for the treatment of MS and has been shown to slow disease progression and reduce relapse rate in several clinical trials using different outcome measures (Steinman 2005). Compared to existing treatments, the efficacy of Tysabri is quite dramatic. However, several cases of progressive multifocal leukoencephalopathy (PML), a lethal resurgence of a latent viral infection linked to the immunosuppressive action of the drug, led to withdrawal (Rudick, Stuart et al.). Tysabri has now been reintroduced into the market with much stricter patent monitoring. Tysabri likely blocks both $T_H$-17 and $T_H$1 cells. A novel small molecule drug that is specific for $T_H$-17 cells and does not compromise the antiviral activity of $T_H$1 cells could be safer and more effective for several reasons: (1) a small molecule drug, administered daily, can be rapidly withdrawn if significant side effects occur; (2) a small molecule drug is more readily manufactured and more easily administered than a biologic, such as Tysabri; and (3) $T_H$1 cells suppress $T_H$-17 differentiation and thus specific inhibition of $T_H$-17 cells may be more effective.

A number of other small molecule drugs are marketed for autoimmune diseases such as rheumatoid arthritis, IBD, and psoriasis. Many of these, such as methotrexate or azathioprine, carry significant toxicity because of anti-metabolite or anti-mitotic effects. Dosing is usually limited. A small molecule drug that has a more specific mechanism of action, such as inhibition of $T_H$-17 cells or other IL-17 expressing T cells, are likely to be safer and, hence, more efficacious as dosages may be elevated to have a substantial inhibitory effect on target cells.

Pharmacologically useful ligands to members of the ROR family of orphan nuclear receptors have not been identified in the published literature. Cholesterol and cholesterol sulfate occupy the ligand binding pocket within the receptor LBD of RORα as determined by x-ray crystallography (Kallen, Schlaeppi et al. 2002; Kallen, Schlaeppi et al. 2004), but, due to the fact that these molecules are plentiful in normal cells, it has not been possible to use these molecules in order to characterize RORα as a pharmacological target (Moraitis and Giguere 2003). A series of RORα ligands was published in 1996 (Missbach, Jagher et al. 1996; Wiesenberg, Chiesi et al. 1998), but these findings have not been independently replicated or evaluated by functional criteria described below. One of the proposed ligands for RORβ, melatonin, has been challenged in the literature (Becker-Andre, Wiesenberg et al. 1994; Greiner, Kirfel et al. 1996; Becker-Andre, Wiesenberg et al. 1997). More recently, it was proposed that all-trans retinoic acid and the synthetic retinoid ALRT 1550 are functional ligands for RORβ and that these two ligands also regulate RORγ in a similar manner, in both cases inhibiting the transcriptional activity of the receptors. All-trans retinoic acid and ALRT 1550 were referred to as "functional" ligands because they were presumed to both bind and regulate transcription through RORβ. The ligands are unlikely to be useful pharmacologically because they are potent activators of the retinoid receptors, RARα, RARβ, RARγ (Thacher, Vasudevan et al. 2000). Therefore all of these ligands fail the test of functional usefulness either on the criterion that their effects have not been reproducible, or because they are ubiquitous, or because they lack specificity. This application describes assay for RORγ, and RORγ ligands that have pharmacologically useful potency (in the range of 50 nM to 1 µM), that have good selectivity, as demonstrated by assays for other members of the nuclear receptor family. These ligands, both agonists and antagonists, have drug-like properties as indicated by rational structure activity relationships among analogues as well as other drug-like properties such as bioavailability and activity in cellular and animal models. Specific RORγ antagonists are predicted to be highly useful in treatment of autoimmune disease by blocking $T_H$-17 function. Agonists of RORγ are predicted to enhance immu-

SUMMARY OF THE INVENTION

The present invention provides a method of inhibiting $T_H$-17 cell differentiation from naïve T cells, or $T_H$-17 cell function/activity, comprising contacting a population of T cells that may include $T_H$-17 cells with an effective amount of an antagonist of retinoic acid related orphan receptor γ (RORγ). In one embodiment, $T_H$-17 cell function/activity is release of a cytokine. The cytokine may be interleukin-17 or interleukin-22. In one embodiment, the RORγ antagonist is at least 20-fold more potent as an RORγ antagonist than as an LXR agonist. In another embodiment, the $T_H$-17 cell differentiation or cytokine release is associated with an inflammatory or an autoimmune disorder. In another embodiment, the inflammatory or autoimmune disorder is arthritis, diabetes, multiple sclerosis, uveitis, rheumatoid arthritis, reactive arthritis, sarcoidosis, psoriasis, psoriatic arthritis, asthma, bronchitis, allergic rhinitis, chronic obstructive pulmonary disease, atherosclerosis, H. pylori infections, ulcers resulting from H. pylori infections, inflammatory bowel disease, Crohn's Disease ulcerative colitis or sprue. Preferably, the RORγ antagonist is a small molecule drug, and is preferably not a polynucleotide. In one embodiment, the antagonist has the structure:

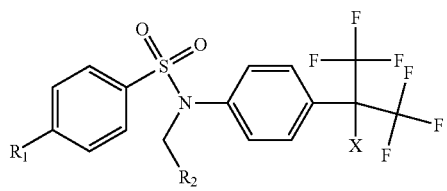

wherein $R_1$=H, $C_1$-$C_6$ alkyl, F, Cl, Br, I, NO2; $R_2$=$C_1$-$C_4$ alkyl; and X=OH, or a pharmaceutically acceptable salt, prodrug, derivative or metabolite thereof.

In one embodiment, the antagonist is OR-1050. In another embodiment, the antagonist has the structure:

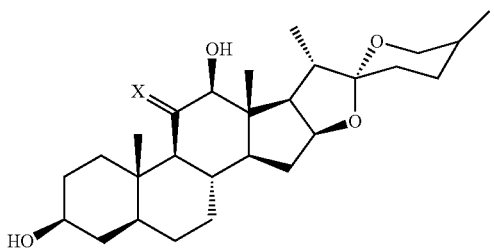

wherein X=O or is absent (X=H,H), or a pharmaceutically acceptable salt, prodrug, derivative or metabolite thereof.

In other embodiments, the antagonist is OR-885, OR-345, OR-13571, OR-2161, OR-133171, or a pharmaceutically acceptable salt, prodrug, derivative or metabolite thereof.

The present invention also provides a method of inhibiting $T_H$-17 cell differentiation from naïve T cells, or $T_H$-17 cell function/activity, in an individual in need thereof, comprising administering an effective amount of an RORγ antagonist to the individual. In one embodiment, the $T_H$-17 cell function/activity is release of a cytokine. In one embodiment, the cytokine is interleukin-17 or interleukin-22. In another embodiment, the RORγ antagonist is at least 20-fold more potent as RORγ antagonist than as LXR agonist. In one embodiment, the RORγ antagonist is orally administered. In another embodiment, the RORγ antagonist is administered on a daily basis without resulting in weight loss or hypertriglyceridemia. In another embodiment, the $T_H$-17 cell differentiation or cytokine release is associated with an inflammatory or autoimmune disorder. In another embodiment, the inflammatory or autoimmune disorder is arthritis, diabetes, multiple sclerosis, uveitis, rheumatoid arthritis, reactive arthritis, sarcoidosis, psoriasis, psoriatic arthritis, asthma, bronchitis, allergic rhinitis, chronic obstructive pulmonary disease, atherosclerosis, H. pylori infections, ulcers resulting from H. pylori infections or inflammatory bowel disease, Crohn's Disease, ulcerative colitis, or sprue. In one embodiment, the antagonist has the structure:

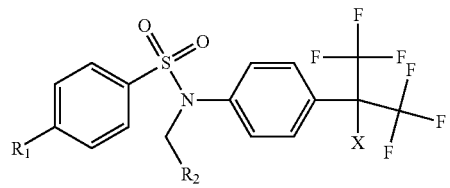

wherein $R_1$=H, $C_1$-$C_6$ alkyl, F, Cl, Br, I, NO$_2$; $R_2$=$C_1$-$C_4$ alkyl; and X=OH, or a pharmaceutically acceptable salt, prodrug, derivative or metabolite thereof.

In one embodiment, the antagonist is OR-1050. In another embodiment, the antagonist has the structure:

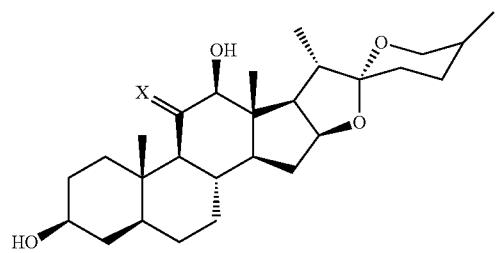

wherein X=O or is absent (X=H,H), or a pharmaceutically acceptable salt, prodrug, derivative or metabolite thereof.

In another embodiment, the antagonist is OR-885, OR-345, OR-13571, OR-2161, OR-133171 or a pharmaceutically acceptable salt, prodrug, derivative or metabolite thereof.

The present invention also provides a method of treating an inflammatory or autoimmune disease in an individual, comprising identifying an individual in need of such treatment, and administering an effective amount of an RORγ antagonist the individual. In another embodiment, the RORγ antagonist is at least 20-fold more potent as RORγ antagonist than as LXR agonist. In one embodiment, the RORγ antagonist is orally administered. In another embodiment, the RORγ antagonist is administered on a daily basis without resulting in weight loss or hypertriglyceridemia. In one embodiment, the inflammatory or autoimmune disorder is arthritis, diabetes, multiple sclerosis, uveitis, rheumatoid arthritis, reactive arthritis, sarcoidosis, psoriasis, psoriatic arthritis, asthma, bronchitis, allergic rhinitis, chronic obstructive pulmonary disease, atherosclerosis, H. pylori infections, ulcers resulting from *H. pylori* infections or inflammatory bowel disease. In one embodiment, the inflammatory bowel disease is Crohn's disease, ulcerative colitis or sprue. Preferably, the RORγ antagonist is a small molecule drug. It is preferably not a polynucleotide, including DNA, antisense, siRNA, and the like. In one embodiment, the antagonist has the structure:

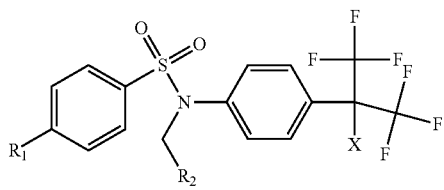

wherein R1=H, C1-C6 Alkyl, F, Cl, Br, I, NO2; R2=C1-C4 Alkyl; and X=OH, or a pharmaceutically acceptable salt, prodrug, derivative or metabolite thereof.

In one embodiment, the antagonist is OR-1050. In another embodiment, the antagonist has the structure

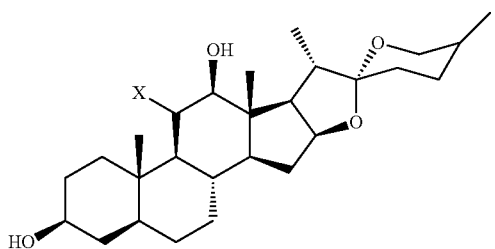

wherein X=O or is absent (X=H,H), or a pharmaceutically acceptable salt, prodrug, derivative or metabolite thereof. In other embodiments, the antagonist is OR-885, OR-345, OR-13571, OR-2161, OR-133171 or a pharmaceutically acceptable salt, prodrug, derivative or metabolite thereof.

The present invention also provides a method of screening for agonists or antagonists to RORα, RORγ or RORβ, comprising contacting a compound with a labeled, expressed ROR LBD and a labeled peptide that includes residues 710-720 (RTVLQLLLGNP; SEQ ID NO: 2) of human RIP140; and measuring the proximity of the two labels, wherein binding of labeled peptide identifies the compound as an agonist and displacement of labeled peptide identifies the compound as an antagonist. In one embodiment, the proximity of the two labels is measured using radioactive or fluorescent probes. In another embodiment, the ROR LBD is labeled with glutathione-S-transferase (GST), and the peptide is labeled with biotin. In another embodiment, wherein the peptide has the sequence ERRT-VLQLLLGNSNK (SEQ ID NO: 3), wherein biotin is linked to the N-terminus of the peptide by an aminohexanoic acid linker.

The present invention also provides a method of increasing the number of T cells reactive to a specific antigen, comprising administering an RORγ agonist in conjunction with, or subsequent to, administration of the antigen.

The present invention also provides a method of increasing the immunogenicity of an immunogenic composition in an individual in need thereof, comprising administering an immunogenicity-increasing amount of an RORγ agonist in conjunction with, or subsequent to, the immunogenic composition. In one embodiment, the immunogenic composition is a vaccine composition. In another embodiment, the vaccine composition is an attenuated live vaccine or a non-replicating and/or subunit vaccine, wherein the vaccine induces memory $T_H$-17 cells specific for said vaccine. In one embodiment, the vaccine is a tumor vaccine, viral vaccine, bacterial vaccine or parasitic vaccine. In one embodiment, the viral vaccine is a DNA viral vaccine, an RNA viral vaccine or a retroviral viral vaccine.

The present invention also provides a method of increasing mucosal immunity to a preselected antigen, comprising administering to a subject a mucosal immunity-increasing amount of an RORγ agonist in conjunction with, or subsequent, to the antigen. In one embodiment, the antigen is a bacterial antigen, viral antigen or tumor antigen.

The present invention also provides a method of enhancing induction, expression and/or release of a pro-inflammatory cytokine, a pro-inflammatory cytokine receptor, a pro-inflammatory chemokine or a pro-inflammatory chemokine receptor in cells capable of expressing said cytokine, cytokine receptor, chemokine or chemokine receptor, comprising administering an RORγ agonist to the cells. In one embodiment, the RORγ agonist is a small organic molecule, protein, peptide, nucleic acid, carbohydrate or antibody. In another embodiment, the pro-inflammatory cytokine is IL-17 or IL-22. In one embodiment, the cells are contacted in vitro, ex vivo or in vivo.

The present invention also provides a method of inducing $T_H$-17 cell differentiation and/or transcription of IL-17 and/or IL-22 in a population of T cells that may include $T_H$-17 cells, comprising contacting the cells with an effective amount of an RORγ agonist. In one embodiment, the cells are contacted in vitro, ex vivo or in vivo.

The present invention also provides a method of inducing $T_H$-17 cell differentiation in an individual in need thereof, comprising administering an effective $T_H$-17 cell differentiation-inducing amount of an RORγ agonist to the individual The present invention also provides a method of inhibiting $T_H$-17 cell differentiation and/or release of IL-17 and/or IL-22, comprising administering an effective amount of an RORγ antagonist to a population of T cells that may include $T_H$-17 cells. In one embodiment, the antagonist is a small organic molecule, protein, peptide, nucleic acid, carbohydrate or antibody. In another embodiment, the T cell is a CD4+ T cell, a CD8+ T-cell or a TCRγδ+ T cell. In one embodiment, the antagonist is administered in vitro, ex vivo or in vivo.

BRIEF DESCRIPTION OF THE DRAWINGS

(FIG. 4A) OR-942 (hyodeoxycholic acid methyl ester) was identified as an agonist in the transcriptional assay. When OR-942 was tested alone, GAL4-RORγ transcriptional activity was only modestly elevated in CHO cells. In the presence of the antagonist T0901317, however, RORγ displays lowered basal activity and OR-942 activates RORγ transcriptional activity by approximately 8-fold.

(FIG. 4B) The agonist activity of OR-942 was confirmed in a biochemical assay based on coregulatory peptide recruitment. OR-942 induces an interaction between partially purified RORγ LBD, expressed as a fusion protein with glutathione-S-transferase (GST-RORγ), and a 15-mer peptide (ERRTVLQLLLGNPTK; SEQ ID NO: 4), or peptide K, derived from the human coregulator protein RIP140 (Lee, Elwood et al. 2002). The peptide is biotinylated at the amino-terminal. The interaction of peptide K and GST-RORγ was followed by fluorescence resonance energy transfer (FRET). The two components of the assay were labeled with an anti-GST antibody coupled to allophycocyanin (APC) and streptavidin-R-phycoerythrin (SA-RPE). FRET units were calculated as the fractional increase (×100) of the APC/RPE fluorescence ratio over the value obtained in the presence of a mutated form of the K peptide (Kmut, ERRTVLQLVVGNPTK; SEQ ID NO: 5), also biotinylated at the N-terminal amino acid residue, that substitutes two of the leucine residues required for coactivator peptide binding (Darimont, Wagner et al. 1998; Li, Lambert et al. 2003) with valine.

FIGS. 8A-D. An RORγ agonist (OR-12872) reverses antagonist (OR-1050) effects on regulation of $T_H$-17 cell differentiation. The methods follow FIG. 7. Each treatment was performed in duplicate, and a representative scatterplot for each treatment is shown. FIG. 8A: control; FIG. 8B: 3 μm OR-1050; FIG. 8C: 3 μm OR-12872; FIG. 8D: 3 μm OR-1050+3 μm OR-12872.

FIG. 9A-D. OR-885 inhibits $T_H$-17 differentiation and OR-12872 reverses its antagonistic effect. The methods follow FIGS. 7 and 8. Each treatment was performed in duplicate, and a representative scatterplot for each treatment is shown. FIG. 9A: control; FIG. 9B: 3 μm OR-885; FIG. 8C: 1 μm OR-112872; FIG. 8D: 3 μm OR-885+1 μm OR-12872.

FIGS. 11A-C. RORγ antagonist inhibits severity, weight loss, onset, Th-17 frequency and inflammation in EAE models. (FIGS. 11A-C) C57BL/6 mice were immunized with 150 μg $MOG_{35-55}$ at day 0 to induce EAE and were dosed daily with corn oil (vehicle) or OR-1050 (50 mg/kg, 2× per day) by oral gavage starting at day −1. At Day 26, the spinal cord was removed for analysis of inflammation (FIG. 11C).

FIGS. 11D-F SJL/J mice were immunized with 75 μg $PLP_{139-151}$ (Day 0). Osmotic pumps delivering vehicle or OR-1050 (~30 mg/kg) were inserted at Days 3 and 4. Day of onset (FIG. 11E) compares the first day when EAE severity is 1 or higher. The ratio of Th-17 cells ($CD4^+CD8^-IL17^+$) to total live cells was analyzed in a separate study (FIG. 11F) at day 9 after immunization with PLP where mice had been dosed daily with OR-1050 (100 mg/kg in HRC-6) since day −1. Statistics (panels A,B,D,F) were performed by Student's t-test. *, P<0.05; #, P<0.01 (mean±sem, n=7-10) or by the Mann-Whitney rank order test (FIGS. 11C, E, median values shown).

FIGS. 13A-F. IL-17 levels in lymph node cells from mice immunized with myelin-derived peptides respond to cognate peptide antigens, IL-23 and RORγ ligands. (FIG. 13A) SJL/J mice were immunized by complete Freund's adjuvant (CFA) only or by Proteolipid Protein residues 139-151 ($PLP_{139-151}$) emulsified in CFA. Lymph nodes were cultured for 3 days in with or without 40 μg/ml PLP in the presence or absence of OR-885. Culture media were analyzed by ELISA for IL-17. (FIGS. 13B-C) Lymph node cells from PLP-immunized SJL/J mice were cultured as before with the addition of 10 ng/ml IL-23 and 3 μM compounds. At the end of 1 day or 3 days in culture, Th-17 ($CD4^+CD8^-IL17^+$) cell frequency was measured by FACS (FIG. 13B) and compared to IL-17 levels in culture media (FIG. 13C). (FIG. 13D-F) Lymph node cells from $MOG_{35-55}$ immunized C57BL/6 mice were cultured for 3 days with 30 μg/ml MOG and/or 10 ng/ml IL-23. RORγ ligands were not added (FIG. 13D), or added at the beginning of the culture at a single concentration (FIG. 13E, 1 μM) or in multiple doses (FIG. 13F).

In FIG. 16A, PBMCs were exposed to 1 μg/ml Con A for 3 days and treated simultaneously with 3 μM OR-885 or DMSO carrier in the presence or absence of 3 μM OR-12872. In FIG. 16B, PBMCs were treated for 3 days in the presence 1 μg/mL Con A and 3 μM of the following compounds: OR-13571, OR-1050, or OR-12872 alone or in combination. In FIG. 16C, T cell blasts were treated with OR-1050, OR-13571, and OR-12872 in the presence of a phorbol ester for 18 hours to induce cytokine release.

(FIG. 17A) Arthritic scores in hind limb (max score=8) for vehicle-treated (n=15) or 100 mg/kg/day OR-1050-treated (n=12) animals. (FIG. 17B) Disease intensity (Mean±SEM) is the area under the curve (AUC) for hind limb clinical scores from day 24 to 48. AUC scores for the two groups were compared by the Mann-Whitney rank order test (one-tailed) to determine statistical significance.

DETAILED DESCRIPTION OF THE PREFERRED EMBODIMENT

Figure 1:
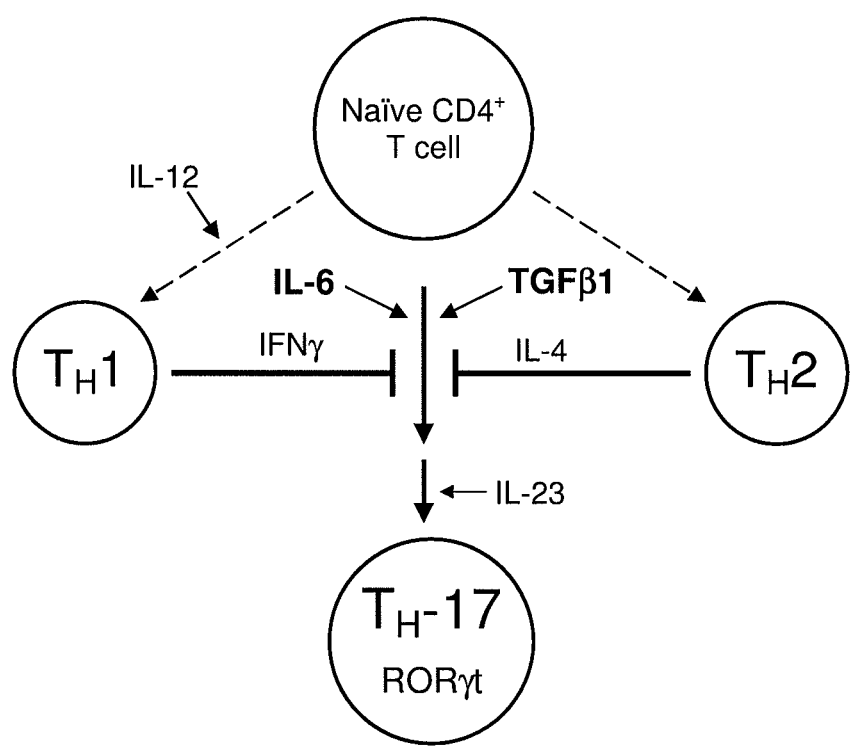
FIG. 1. Naive T cell differentiation in mouse. $T_H$-17 cell differentiation is independent of $T_H$1 and $T_H$2. IFNγ and IL-4, from $T_H$1 and $T_H$2, respectively, antagonize $T_H$-17 differentiation, while TGFβ and IL-6 stimulate $T_H$-17 differentiation. RORγt is required for $T_H$-17 cell formation, and its expression appears to take place early in differentiation (Ivanov, McKenzie et al. 2006). IL-23 appears to have a stimulatory effect on the differentiated $T_H$-17 cell.
Figure 2:
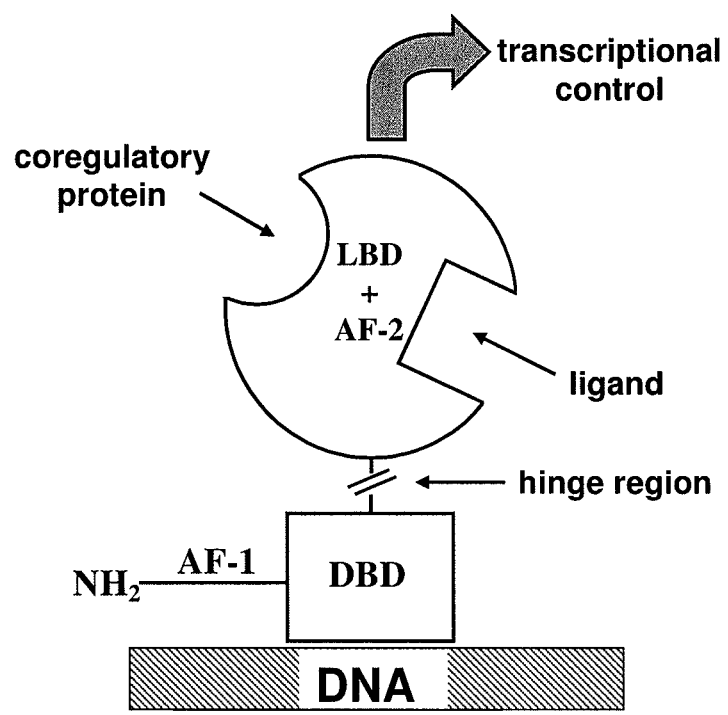
FIG. 2. Nuclear Receptor Structure. The activation function-1 (AF-1) domain induces gene transcription independently of ligand. The activation function-2 domain (AF-2) is a part of the LBD and is required for the ligand-dependent transcriptional effect.

The present invention includes the discovery that small molecule antagonists to retinoic acid related orphan receptor γ (RORγ) inhibit $T_H$-17 cell differentiation from naïve mouse T cells in cell culture, and inhibit the release of cytokines from mouse and human $T_H$-17 cells. These small molecule antagonists have unique and beneficial properties for treatment of inflammatory and autoimmune diseases, since they inhibit the release of several pro-inflammatory cytokines from $T_H$-17 cells, including IL-17 and IL-22. Conversely, a potent RORγ agonist can enhance $T_H$-17 cell formation and reverse the antagonist effect. These small molecule inhibitors can be used to treat a variety of inflammatory and autoimmune disorders including, but not limited to, arthritis, diabetes, multiple sclerosis, uveitis, rheumatoid arthritis, psoriasis, asthma, bronchitis, allergic rhinitis, chronic obstructive pulmonary disease, atherosclerosis, H. pylori infections, ulcers resulting from H. pylori infections and inflammatory bowel disease (IBD). IBD includes, but is not limited to, Crohn's disease, ulcerative colitis and sprue.

RORγ agonists and antagonists are fairly specific to $T_H$-17 cells and do not appear to have a primary effect on $T_H$1 cells. Several strategies that inhibit development or activity of $T_H$-17 cells for the treatment of MS and other autoimmune diseases can be envisioned, but these primarily involve treatment with macromolecules such as antibodies that block IL-23 or IL-17 (Bowman, Chackerian et al. 2006) or cytokines that inhibit $T_H$-17 cell function (Batten, Li et al. 2006; Stumhofer, Laurence et al. 2006). RORγ antagonists offer the first approach to specifically block $T_H$-17 development with small molecule drugs. An RORγ antagonist offers superior properties for human dosing and therapeutic use such as oral bioavailability. The following definitions are provided:

A receptor antagonist is a molecule that inhibits the normal physiological function of a receptor. Many drugs work by blocking the action of endogenous receptor agonists such as hormones and neurotransmitters. Antagonists that compete with an agonist for a receptor are competitive antagonists. Those that antagonize by other means are non-competitive antagonists.

A receptor agonist is a molecule that, in the nuclear receptor context, increases the transcriptional activity of a receptor or overcomes the activity of a competitive receptor antagonist.

A small molecule drug is an orally or intravenously bioavailable compound having a molecular weight less than about 600 daltons.

Related nuclear receptor. The human and mouse families of nuclear receptors comprise 48 members (Laudet 1999), and these have been arranged in both families (e.g., family 1, including both RORγ and LXRα) and subfamilies (e.g., NR1F) that include RORα, RORβ, and RORγ. For the purposes of this discussion, related nuclear receptors are those that belong to a single receptor subfamily, such as NR1F, and unrelated nuclear receptors may belong to the same family but to different subfamilies.

A confirmed hit at RORγ is a small molecule compound that regulates transcription through RORγ and also regulates the affinity of the RORγ LBD with an appropriate coregulatory peptide in a validated assay for the receptor.

Potency. A measure of compound concentration required to activate or inhibit a pharmacological endpoint. Potency is often estimated as $EC_{50}$ (effective concentration producing a 50% effect) or by similar measures known to those skilled in the art of pharmacology.

Rank order of potency is a method of comparing small molecule ligand pharmacology data from two separate assays. Compounds are ranked by $EC_{50}$ or other measure of potency in each of the two assays. The purpose of this ranking is to provide a method of comparing the results of two different assays for which absolute compound potencies may differ.

A transcriptional assay for a nuclear receptor measures regulation of gene expression of a target gene that contains a response element for that receptor in its promoter region. Promoter regions can be engineered to contain appropriate response elements and these in turn can be coupled to a variety of reporter genes. Such assays are widely used to characterize nuclear receptor function and utilize target genes, such as chloramphenicol acetyl transferase (CAT), luciferase (LUC), and beta-lactamase (BLA). The activity of these enzymes is readily assayed in cell extracts or whole cells. Nuclear receptor assays also take advantage of the fact that the ligand-binding domain (LBD) of the receptor can function independently of its DNA-binding domain (DBD). Chimeric receptors that contain a common DBD, for example the DBD of the yeast transcriptional factor GAL4 (Webster, Green et al. 1988), are fused to the LBDs of individual nuclear receptors. Multiple nuclear receptor LBDs, fused to the same DBD, may be screened against a common target gene that contains the response element for that DBD (Schultz, Tu et al. 2000). Chimeric receptors are co-transfected individually with the common target gene. Ligands effects are determined after incubation for a sufficient period of time according to changes in level of expression of the target gene.

A biochemical assay for a nuclear receptor is carried out in the presence of partially purified receptor LBD and, directly or indirectly, measures binding of ligand. Two methods are commonly used: (i) competitive displacement of known, labeled ligand and (ii) recruitment of coregulatory peptide. Coregulatory peptide recruitment takes advantage of the fact that the receptor LBD will usually bind short peptides derived from conserved sequences within the so-called coregulatory proteins in a manner that depends on the presence or absence of ligand (Bramlett, Yao et al. 2000; Lee, Elwood et al. 2002; Wu, Chin et al. 2002). Coregulatory proteins in turn are required for transcriptional regulation in response to ligand binding to the receptor (McKenna and O'Malley 2002). Both receptor LBD and peptide are tagged with molecular markers, and the degree of association of these markers determined in the presence or absence of ligand.

RORγ. The gene that encodes RORγ (RORc) undergoes alternative splicing to give rise to two splicing isoforms, RORγ and RORγt. The expression of RORγ is widespread, and mRNA for RORγ appears in liver, muscle, fat and many other tissues (Jetten, Kurebayashi et al. 2001). The RORγt splicing isoform is predicted to generate a protein that is truncated by 21 amino acids at the N-terminus of RORγ (He, Deftos et al. 1998). RORγt is expressed predominantly in thymocytes, lymph node precursors known as LTi cells, in $T_H$-17 cells, and in other T cells, including a subpopulation of $CD8^+$, $γδTCR^+$, and NKT cells (Ivanov, McKenzie et al. 2006; Ivanov and Littman. 2007). The RORγt isoform contains an LBD that is identical to RORγ. For the purpose of this application, the two receptors may be referred to collectively as RORγ.

RORγ Function. Nuclear receptors are thought to act primarily as nuclear transcription factors, by regulating gene expression. Some nuclear receptors have been shown to have acute, non-genomic effects that cannot be explained by gene transcription. Examples include the thyroid and estrogen receptors (Hiroi, Kim et al. 2006). Although a transcriptional assay is useful for identification of RORγ ligands, the ligand response of RORγ may include direct activation of other cell-signaling pathways, such as those mediated by kinases, phosphatases, or levels of intracellular messengers.

FITC—Flourescein isothiocyanate
APC—allophycocyanin
PE—phycoerythrin
LBD—ligand-binding domain
DBD—DNA-binding domain
FRET—Fluorescence resonance energy transfer The $T_H$-17 cell is recently-described subset of $CD4^+$ T helper cells that expresses IL-17 and IL-17F, as well as other cytokines, including pro-inflammatory cytokines such as IL-22 (Liang, Tan et al. 2006). The $T_H$-17 cell also expresses the autocrine cytokine, IL-21. Other T cells may also express RORγt and IL-17. The most prevalent type of IL-$17^+$ T cell in the gut is the $TCRαβ^+CD4^+$ $T_H$-17 cell (Ivanov, McKenzie et al. 2006), while the γδ T cell is the primary source of IL-17 in response to pulmonary infection (Lockhart, Green et al. 2006). In addition, $CD8^+$ T cells, γδ T cells and NKT cells also express RORγ. Thus, $T_H$-17 cells are a subset of IL-$17^+$ T cells. A significant fraction of the IL-17+ T cells appear to be RORγt$^+$ (Ivanov and Littman 2007).

Pharmaceutical composition refers to a mixture of RORγ antagonist or inhibitor, or a pharmaceutically acceptable salt, prodrug, derivative or metabolite thereof, with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

Carrier defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

Diluent defines chemical compounds diluted in water that will dissolve or suspend the compound of interest and preferably also stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

Physiologically acceptable defines a carrier or diluent that is suitable for in vivo administration.

Pharmaceutically acceptable salt refers to a salt form of an original compound formed by association of a counterion with that compound, wherein the counterion is generally nontoxic. Pharmaceutical salts can be obtained, for example, by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glutamine, tris(hydroxymethyl)methylamine, and salts with amino acids such as arginine, lysine, and the like.

Metabolite refers to a compound to which a RORγ antagonist or agonist is converted within the cells of a mammal. The pharmaceutical compositions of the present invention may include a metabolite of a RORγ antagonist instead of the RORγ antagonist. The scope of the methods of the present invention includes those instances where the RORγ antagonist is administered to the patient, yet the metabolite is the bioactive entity.

Prodrug refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

In a further aspect, the present invention relates to a method of treating a patient with a pharmaceutical composition as described herein.

The term "treating" or "treatment" does not necessarily mean total cure. Any alleviation of any undesired signs or symptoms of the disease to any extent or the slowing down of the progress of the disease can be considered treatment. Furthermore, treatment may include acts that may worsen the patient's overall feeling of well being or appearance. Treatment may also include lengthening the life of the patient, even if the symptoms are not alleviated, the disease conditions are not ameliorated, or the patient's overall feeling of well being is not improved.

RORγ Antagonists

The present invention provides compounds that selectively inhibit the transcriptional activity of the orphan nuclear receptor RORγ. These RORγ antagonists may be small organic molecules, proteins, peptides, nucleic acids, carbohydrates or antibodies. These compounds permit the properties of RORγ as a pharmacological target to be investigated in isolated cells and in animals. Further, the invention provides for novel methods of treating autoimmune disease and related conditions by inhibiting the function and/or activity of TH-17 cells, or by inhibiting the differentiation of TH-17 cells, or by inhibiting IL-17 and IL-22 release in a population of T cells that may include TH-17 cells (e.g., CD4+ T cells) and other RORγt+ IL-17+ T cells such as CD8+ T cells, NKT, or TCRγδ+ T cells, through suppression of the activity of RORγ. In examples shown herein, specific compounds that inhibit or activate transcription through the RORγ LBD, respectively RORγ antagonists or agonists, are described, and structurally distinct antagonists of RORγ transcription specifically inhibit the differentiation of CD4+ $T_H$-17 cells from naïve CD4+ T cells. Furthermore, the structurally distinct antagonists also inhibit the release of IL-17 from murine $T_H$-17 cells during differentiation or from memory IL-17+ T cells in lymph node cultures. In addition, the structurally diverse RORγ antagonists inhibit IL-17 release from human peripheral blood mononuclear cells (PBMCs).

The examples demonstrate that pharmacologically useful small molecules for cellular studies can be identified by receptor assays. To be useful, the molecules should be active in an assay of receptor-mediated transcription. Second, in addition to activity in a transcriptional assay, such molecules should be active in a second receptor assay that uses a mechanistically distinct readout, such as coactivator or coregulatory protein or peptide recruitment to receptor LBD as a function of ligand concentration (Heery, Kalkhoven et al. 1997; Lee, Elwood et al. 2002). The proximity of the RORγ LBD and the coregulatory peptide or macromolecule is measured by one of several well-established biophysical methods. Some of these methods, well known to practitioners of the art of studying protein-peptide interactions, include fluorescence resonance energy transfer (FRET), fluorescence polarization, time-resolved FRET (TR-FRET) with europium conjugates as donor, and Alpha Screen, in which laser-induced oxygen emission from a donor bead stimulates a fluorophore in an acceptor bead in close proximity (Iannone, Consler et al. 2001; Lee, Elwood et al. 2002; Xu, Stanley et al. 2002; Moore, Galicia et al. 2004; Li, Choi et al. 2005).

The biochemical assay excludes molecules that non-specifically regulate an RORγ reporter gene in culture. To allow definitive findings in cell experiments, a compound will ideally have an $EC_{50}$<1 μM and measurable cytotoxicity only at higher concentrations. Finally, such molecules should be selective for RORγ. If this is not the case, a secondary control should be available, for example, an agonist that demonstrates the reversibility of antagonist effect. Without these controls, there is the opportunity to confuse an effect of a non-specific candidate RORγ ligand on $T_H$-17 cells with an authentic activity of the small molecule mediated by interaction with the LBD of RORγ. The transcriptional and biochemical assays described herein can be used to determine the ability of any small molecule to act as an RORγ receptor antagonist or agonist.

The invention provides examples in which the validity of certain hits were further confirmed by demonstrating that a series of related compounds to the hit share a similar rank order of potency in both the transcriptional and biochemical assays over a wide range.

In view of the fact that RORγt is required for CD4+ $T_H$-17 cell formation in mice (Littman and Eberl 2006), we tested whether RORγ ligands specifically inhibit $T_H$-17 differentiation from naïve CD4+ T cells in culture (Mangan, Harrington et al. 2006; Veldhoen, Hocking et al. 2006). $T_H$-17 inhibition by small molecule modulation through RORγ was verified by several criteria. First, three separate structurally distinct RORγ antagonists (OR-1050, OR-885, and OR-13571, $EC_{50}$<1 μM in the transcriptional assay) had comparable activity in $T_H$-17 inhibition; second, antagonist effect could be reversed by a potent and specific agonist (OR-12872) to RORγ; and third, the RORγ ligand effect was specific for cell culture differentiation of $T_H$-17 but not $T_H$-1 cells.

Further, the invention provides for molecules with a reasonable margin of safety. We demonstrated that one of the RORγ ligands, OR-1050, can be dosed in mice such that it should cause a pharmacological effect through RORγ. We therefore examined the effect of the compound on function of the thymus, since the major pool of developing T lymphocytes, the double positive $CD4^+CD8^+$ (DP) T cells, expresses RORγt. Germline deletion of RORγ or RORγt leads to an increased rate of DP thymocyte apoptosis and a reduction in DP thymocyte number to about 30% of control (Kurebayashi, Ueda et al. 2000; Sun, Unutmaz et al. 2000; Eberl and Littman 2004). Therefore, a model study with OR-1050 was used to investigate possible effects on thymic function. The RORγ antagonist OR-1050 also activates the nuclear receptors LXRα and LXRβ, and therefore the bioavailability of OR-1050 could be demonstrated by induction of triglyceride accumulation in liver since this is a well-defined endpoint for LXR ligands (Schultz, Tu et al. 2000; Beyer, Schmidt et al. 2004). The $EC_{50}$ for OR-1050 at LXRα (1.5 μM) is higher than for RORγ (0.3 μM) in transcriptional assays, suggesting that RORγ would also be antagonized in the drug-treated animals. In a six day study, liver triglycerides were markedly elevated by daily exposure to 100 mg/kg OR-1050, but the compound had no effect on the frequency or total number of the major cell types of the thymus. This invention therefore provides for compounds that will have limited effects on the function of the thymus.

Further, OR-1050 slows the onset of EAE in C57BL/6 female mice injected with a myelin-derived peptide. The data are consistent with the prediction that an RORγ antagonist free of LXR activity will be effective in this model. In addition, OR-1050 is demonstrated to have modest bioavailability. The invention provides a method for selecting compounds that have negligible or reduced LXR potency while maintaining or improving RORγ potency. T0901317 does not elevate liver triglyceride levels in mice where the LXRα and LXRβ receptors have been deleted (Schultz, Tu et al. 2000). More specific RORγ antagonists are predicted to have beneficial effects in animal models of CIA, EAE, and IBD while limiting the undesirable consequences of LXR activation, such as liver triglyceride accumulation and elevated serum LDL (Schultz, Tu et al. 2000; Beyer, Schmidt et al. 2004; Groot, Pearce et al. 2005), or other undesirable consequences, either for safety or efficacy, of activation, inhibition, or interaction with other known pharmacological targets.

In addition, the invention provides for compounds that suppress IL-17 expression in activated human T cells. Elevated IL-17 levels in disease tissue are strongly suggested to signal pathogenic involvement of $T_H$-17 and other IL-17 positive cells.

The advantages of direct targeting of $T_H$-17 cells with a small molecule drug could be very significant compared to the biologics that are very likely under development (Bowman, Chackerian et al. 2006). In one embodiment, a drug from the RORγ antagonist class has good oral bioavailability. In another embodiment, the drug has a half-life of four hours or more, enabling once or twice-daily administration. Nuclear receptor ligands have commonly given rise to orally bioavailable drugs; OR-1050 is an example of an orally-bioavailable RORγ antagonist characterized in these studies. The advantage of an orally bioavailable drug is: (i) direct oral administration is feasible; (ii) unlike injectable biologics, which may have an extremely long half life, a small molecule drug with reasonable half-life can be withdrawn if necessary to limit side effects and (iii) small molecule drugs are readily manufactured. Such compounds may also be selected for clinical development by potency in animal models of EAE, CIA and IBD and by parallel in vivo studies of compound safety.

RORγ Agonists

RORγ agonists may be small organic molecules, proteins, peptides, nucleic acids, carbohydrates or antibodies. Particularly preferred are small organic molecules. The present invention also includes methods of increasing the number of T cells reactive to a specific antigen by administering an RORγ agonist in conjunction with, or subsequent to, administration of the antigen; and for enhancing the differentiation of $T_H$-17 cells by contacting a population of T cells that may include $T_H$-17 cells with an RORγ agonist. In one embodiment, agonists of RORγ are used to enhance or modulate an immune response. In another embodiment, an RORγ agonist is used to enhance the effectiveness of vaccine compositions. Vaccination remains the primary mechanism of inhibiting the spread of infectious agents. For newly discovered organisms, vaccination is the most highly favored option since drug therapy may require decades to provide clinical options. Although most healthy individuals respond to the foreign antigen presented by vaccination, there is a critical need to stimulate the immune response in the elderly, who are much less responsive to vaccination in the first place due to aging of their immune system. Furthermore, subunit vaccines, although easy to prepare since they are based on exogenously expressed proteins from the pathogen, are often not highly immunogenic. Thus, concomitant stimulation of the immune response will improve vaccine take. The vaccine compositions may be attenuated live vaccines, or non-replicating and/or subunit vaccines. In one embodiment, these vaccines induce memory $T_H$-17 cells specific for the vaccine. Types of vaccines include, but are not limited to, tumor vaccines, viral vaccines (DNA, RNA or retroviral), bacterial vaccines and parasitic vaccines.

RORγ agonists can also be used to increase mucosal immunity to a preselected antigen by administering a mucosal immunity-enhancing amount of an RORγ agonist in conjunction with, or subsequent to, the antigen. The antigen can be bacterial, viral or a tumor antigen.

An RORγ agonist can be used to increase the immunogenicity of an immunogenic composition (e.g., vaccine composition) by administering the RORγ agonist in conjunction with, or subsequent to, the immunogenic composition. RORγ agonists can also be used to enhance induction, expression and/or release of a pro-inflammatory cytokine (e.g., IL-6, IL-17, IL-22, IL-3, TNF-α), a pro-inflammatory cytokine receptor, a pro-inflammatory chemokine (e.g., CC chemokines, CXC chemokines, C chemokines, $CX_3C$ chemokines) or a pro-inflammatory chemokine receptor in cells capable of expressing the cytokine, cytokine receptor, chemokine or chemokine receptor, by administering the RORγ agonist to the cells. The administration may be in vitro, ex vivo or in vivo.

The RORγ agonists described herein also induce $T_H$-17 cell differentiation and/or transcription of IL-17 and/or IL-22 in a population of T cells that may include $T_H$-17 cells. The RORγ agonists may be administered in vitro, ex vivo or in vivo.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990. The pharmaceutical compositions may also be administered to other mammals, including dogs, cats, sheep, pigs, horses, cows, and the like.

Thus, the veterinary use of these pharmaceutical compositions is also within the scope of the present invention.

Suitable routes of administration may, for example, include oral, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the RORγ agonists/antagonists of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

For topical administration, the compounds may be formulated for administration to the epidermis as ointments, gels, creams, pastes, salves, gels, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally, including sublingually, which include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 6000 mg of each ingredient, preferably between 1 mg and 5000 mg, e.g. 25 to 5000 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2500 mg and the total daily dosage by parenteral administration will typically be in the range 0.1 to 400 mg. Suitably the compounds will be administered for a period of continuous therapy, for example for a week or more, or for months or years.

In one embodiment, the dose of the pharmaceutical composition comprising a RORγ agonist or antagonist or a pharmaceutically acceptable salt, prodrug, derivative or metabolite thereof, is from about 10 to about 50 mg per day.

In another embodiment, the RORγ antagonist is administered daily without resulting in weight loss or hypertriglyceridemia.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen that maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

The compositions described herein may also be used in the preparation of a medicament for treatment of any of the disorders described above.

Example 1

This example describes ligands to RORγ and confirms their receptor regulation properties in two mechanistically distinct receptor assays. Transcriptional assays for mouse and human RORγ (mRORγ and hRORγ) were implemented in cultured cells. A biochemical assay, using exogenously expressed mRORγ LBD, was established to measure ligand-mediated regulation of coregulatory peptide recruitment in vitro. The transcriptional assay measures the product of a reporter gene, such as an enzyme, whose expression is in turn regulated by the RORγ LBD. The biochemical assay responds to a ligand-dependent conformational change in the receptor LBD that changes receptor affinity for coregulatory peptide. The ligands to RORγ described here were predominantly identified in the transcriptional assay and confirmed in the biochemical assay.

This example also describes several additional tests that were commonly performed to confirm the authenticity of a hit to RORγ. These tests also verified the validity of the transcriptional and biochemical assays used. In all cases, the activity of a compound was also tested in transcriptional assays for the orphan nuclear receptors RORα, RORβ, and SF-1 to demonstrate specificity and to rule out a non-specific effect on the assay system as an explanation for the apparent activity. In some cases, close analogs of a confirmed hit were obtained by synthesis or purchase from a commercial source. The series of compounds related to the confirmed hit was then tested in the biochemical and transcriptional assays. The rank order of the potency of the compounds was then compared. If closely similar for the two assays, the findings demonstrated that minor chemical modifications had equivalent effects on compound interaction with the RORγ LBD in each assay. The data imply in turn that the compounds are binding to the same binding pocket. Even though absolute EC$_{50}$ values may differ in a rank order comparison, the observation that relative values are similar provides strong confirmation of the conclusion that the identified compounds act directly through RORγ and not by a secondary mechanism that is assay but not receptor-specific. This results presented in this example demonstrate that the transcriptional and biochemical assays provide an internally consistent method of characterizing RORγ ligand potency and that more potent compounds can be identified using this assay technology by a program of additional screening or directed medicinal chemistry synthesis.

Methods

Transcriptional Assay. Gal4-mRORγ was generated by inserting the LBD of mouse RORγ (Ile-251-Lys-516) into the EcoRI-HindIII site of pFA-CMV. The vector pFA-CMV (Stratagene, La Jolla, Calif.) contains the yeast Gal4 DNA binding domain (amino acids 1-148) upstream of the multiple cloning site where the Ecoki and HindIII restriction enzyme sites are found. The fragment of mRORγ was a PCR product using the template of pM-mRORγ (Medvedev, Yan et al. 1996). The complete Gal4-mRORγ nucleotide sequence is shown below:

```
(Gal4 DBD)
                                                (SEQ ID NO: 7)
ATGAAGCTACTGTCTTCTATCGAACAAGCATGCGATATTTGCCGACTT

AAAAAGCTCAAGTGCTCCAAAGAAAAACCGAAGTGCGCCAAGTGTCTG

AAGAACAACTGGGAGTGTCGCTACTCTCCCAAAACCAAAAGGTCTCCG

CTGACTAGGGCACATCTGACAGAAGTGGAATCAAGGCTAGAAAGACTG

GAACAGCTATTTCTACTGATTTTTCCTCGAGAAGACCTTGACATGATT

TTGAAAATGGATTCTTTACAGGATATAAAAGCATTGTTAACAGGATTA

TTTGTACAAGATAATGTGAATAAAGATGCCGTCACAGATAGATTGGCT

TCAGTGGAGACTGATATGCCTCTAACATTGAGACAGCATAGAATAAGT

GCGACATCATCATCGGAAGAGAGTAGTAACAAAGGTCAAAGACAGTTG

ACTGTATCGCCG (linker)
                                                (SEQ ID NO: 8)
GGATCCGCCCGGGCTGGAATTCGC (mRORγ LBD)
                                                (SEQ ID NO: 9)
ATTCCCAGTTTCTGCAGTGCCCCAGAGGTACCATATGCCTCTCTGAC

AGACATAGAGTACCTGGTACAGAATGTCTGCAAGTCCTTCCGAGAGA

CATGCCAGCTGCGACTGGAGGACCTTCTACGGCAGCGCACCAACCTC

TTTTCACGGGAGGAGGTGACCAGCTACCAGAGGAAGTCAATGTGGGA

GATGTGGGAGCGCTGTGCCCACCACCTCACTGAGGCCATTCAGTATG

TGGTGGAGTTTGCCAAGCGGCTTTCAGGCTTCATGGAGCTCTGCCAG

AATGACCAGATCATACTACTGACAGCAGGAGCAATGGAAGTCGTCCT

AGTCAGAATGTGCAGGGCCTACAATGCCAACAACCACACAGTCTTTT

TTGAAGGCAAATACGGTGGTGTGGAGCTGTTTCGAGCCTTGGGCTGC

AGCGAGCTCATCAGCTCCATATTTGACTTTTCCCACTTCCTCAGCGC

CCTGTGTTTTTCTGAGGATGAGATTGCCCTCTACACGGCCCTGGTTC

TCATCAATGCCAACCGTCCTGGGCTCCAAGAGAAGAGGAGAGTGGAA

CATCTGCAATACAATTTGGAACTGGCTTTCCATCATCATCTCTGCAA

GACTCATCGACAAGGCCTCCTAGCCAAGCTGCCACCCAAAGGAAAAC

TCCGGAGCCTGTGCAGCCAACATGTGGAAAAGCTGCAGATCTTCCAG

CACCTCCACCCCATCGTGGTCCAAGCCGCCTTCCCNCCACTCTATAA

GGAACTCTTCAGCACTGATGTTGAATCCCCTGAGGGGCTGTCAAAGT

GA
```

The complete Gal4-mRORγ protein sequence is shown below:

(Gal4 DBD)
(SEQ ID NO: 10)
MKLLSSIEQACDICRLKKLKCSKEKPKCAKCLKNNWECRYSPKTK

RSPLTRAHLTEVESRLERLEQLFLLIFPREDLDMILKMDSLQDIK

ALLTGLFVQDNVNKDAVTDRLASVETDMPLTLRQHRISATSSSEE

SSNKGQRQLTVSP (linker)
(SEQ ID NO: 11)
GSARAGIR (mRORγ LBD)
(SEQ ID NO: 12)
IPSFCSAPEVPYASLTDIEYLVQNVCKSFRETCQLRLEDLLRQRT

NLFSREEVTSYQRKSMWEMWERCAHHLTEAIQYVVEFAKRLSGFM

ELCQNDQIILLTAGAMEVVLVRMCRAYNANNHTVFFEGKYGGVEL

FRALGCSELISSIFDFSHFLSALCFSEDEIALYTALVLINANRPG

LQEKRRVEHLQYNLELAFHHHLCKTHRQGLLAKLPPKGKLRSLCS

QHVEKLQIFQHLHPIVVQAAFXPLYKELFSTDVESPEGLSK

Gal4-hRORγ was generated by inserting the ligand-binding domain of human RORγ LBD (Ser-253-Lys-518) into pFA-CMV by BamHI-KpnI sites. The vector pFA-CMV (Stratagene, La Jolla, Calif.) contains the yeast Gal4 DNA binding domain (amino acids 1-148) at N-terminal of the multiple cloning sites. The fragment of hRORγ LBD was a PCR product using the template of a commercial clone from Invitrogen (Clone ID: 5186655; Vector: pCMV-SPORT6). The complete Gal4-hRORγ nucleotide sequence is shown below:

(Gal4 DBD)
(SEQ ID NO: 7)
ATGAAGCTACTGTCTTCTATCGAACAAGCATGCGATATTTGCCGAC

TTAAAAAGCTCAAGTGCTCCAAAGAAAAACCGAAGTGCGCCAAGTG

TCTGAAGAACAACTGGGAGTGTCGCTACTCTCCCAAAACCAAAAGG

TCTCCGCTGACTAGGGCACATCTGACAGAAGTGGAATCAAGGCTAG

AAAGACTGGAACAGCTATTTCTACTGATTTTTCCTCGAGAAGACCT

TGACATGATTTTGAAAATGGATTCTTTACAGGATATAAAAGCATTG

TTAACAGGATTATTTGTACAAGATAATGTGAATAAAGATGCCGTCA

CAGATAGATTGGCTTCAGTGGAGACTGATATGCCTCTAACATTGAG

ACAGCATAGAATAAGTGCGACATCATCATCGGAAGAGAGTAGTAAC

AAAGGTCAAAGACAGTTGACTGTATCGCCG (linker)
(SEQ ID NO: 13)
GGATCC (hRORγ LBD)
(SEQ ID NO: 14)
AGCCCCAGTTTCCGCAGCACACCGGAGGCACCCTATGCCTCCCTGA

CAGAGATAGAGCACCTGGTGCAGAGCGTCTGCAAGTCCTACAGGGA

GACATGCCAGCTGCGGCTGGAGGACCTGCTGCGGCAGCGCTCCAAC

ATCTTCTCCCGGGAGGAAGTGACTGGCTACCAGAGGAAGTCCATGT

GGGAGATGTGGGAACGGTGTGCCCACCACCTCACCGAGGCCATTCA

GTACGTGGTGGAGTTCGCCAAGAGGCTCTCAGGCTTTATGGAGCTC

TGCCAGAATGACCAGATTGTGCTTCTCAAAGCAGGAGCAATGGAAG

TGGTGCTGGTTAGGATGTGCCGGGCCTACAATGCTGACAACCGCAC

GGTCTTTTTTGAAGGCAAATACGGTGGCATGGAGCTGTTCCGAGCC

TTGGGCTGCAGCGAGCTCATCAGCTCCATCTTTGACTTCTCCCACT

CCCTAAGTGCCTTGCACTTTTCCGAGGATGAGATTGCCCTCTACAC

AGCCCTTGTTCTCATCAATGCCCATCGGCCAGGGCTCCAAGAGAAA

AGGAAAGTAGAACAGCTGCAGTACAATCTGGAGCTGGCCTTTCATC

ATCATCTCTGCAAGACTCATCGCCAAAGCATCCTGGCAAAGCTGCC

ACCCAAGGGGAAGCTTCGGAGCCTGTGTAGCCAGCATGTGGAAAGG

CTGCAGATCTTCCAGCACCTCCACCCCATCGTGGTCCAAGCCGCTT

TCCCTCCACTCTACAAGGAGCTCTTCAGCACTGAAACCGAGTCACC

TGTGGGGCTGTCCAAGTGA

The complete Gal4-hRORγ protein sequence is shown below:

(Gal4 DBD)
(SEQ ID NO: 10)
MKLLSSIEQACDICRLKKLKCSKEKPKCAKCLKNNWECRYSPK

TKRSPLTRAHLTEVESRLERLEQLFLLIFPREDLDMILKMDSL

QDIKALLTGLFVQDNVNKDAVTDRLASVETDMPLTLRQHRISA

TSSSEESSNKGQRQLTVSP (linker)
(SEQ ID NO: 15)
GS (hRORγ LBD)
(SEQ ID NO: 16)
SPSFRSTPEAPYASLTEIEHLVQSVCKSYRETCQLRLEDLLR

QRSNIFSREEVTGYQRKSMWEMWERCAHHLTEAIQYVVEFAK

RLSGFMELCQNDQIVLLKAGAMEVVLVRMCRAYNADNRTVFF

EGKYGGMELFRALGCSELISSIFDFSHSLSALHFSEDEIALY

TALVLINAHRPGLQEKRKVEQLQYNLELAFHHHLCKTHRQSI

LAKLPPKGKLRSLCSQHVERLQIFQHLHPIVVQAAFPPLYKE

LFSTETESPVGLSK

Four other orphan nuclear receptors were similarly cloned as Gal4-LBD hybrids in pFA-CMV by PCR as follows for initial screening studies: human SF-1 (NR5A1, aa 198-462) at BamHI and XbaI restriction enzymes sites; mRORα (NR1F1, aa 266-523) at XmaI-HindIII restriction enzymes sites; human RORβ (NR1F2, aa 201-459) at EcoRI and KpnI restriction enzyme sites; and mouse LRH-1 (NR5A2, aa 311-561) at EcoRI and HindIII restriction enzyme sites.

A firefly luciferase reporter gene for Gal4 DBD hybrid receptors, such as Gal4-RORγ, contains five copies of the Gal4 17-mer response element in its promoter and the coding sequence for firefly luciferase (pG5-luc, Promega). CHO (Chinese Hamster Ovary) cells were cultured in Ham's F12 medium supplemented with 10% fetal calf serum (Gemini Biologicals), 10 μg/ml penicillin and streptomycin, and were maintained in a humidified 37° C. incubator (Thermo Electron, Steri-Cycle) with 5% $CO_2$. 24 hours before transfection, cells were plated in T175 flasks (5×10⁶ cells/flask) or T75 flasks (1.7×10⁶ cells/flask). Transient transfection of CHO cells was performed using TransIT-CHO reagents (Minis, Madison, Wis.) with a mixing ratio of 2:6:1 between plasmid DNA (in μg), TransIT-CHO (in pl) and CHO-mojo (in μl). As an example, 9 μg pG5-luc, 8.75 μg pcDNA3 and 0.25 μg receptor plasmid were transfected into each T175 flask.

Four hours after transfection, cells were dislodged with trypsin and seeded into a 384-well plate at 8,000 cells/well using a Titertek Multidrop 384. Edge effects within the 384-well plate were minimized by leaving plates at room temperature for 30 min so that cells plated evenly within each well (Lundholt, Scudder et al. 2003). Plates are maintained at 37° C. in a humidified atmosphere with 7% $CO_2$ overnight. Four (4) hours after cell seeding, compounds dissolved in DMSO at 10 mM were added to cells at final concentrations of 20 micromolar (μM) to 20 nanomolar (nM) in 0.2% DMSO in triplicate plates. Approximately 40 hours later, cytotoxicity in the assay well was characterized by addition of the dye resazurin (O'Brien, Wilson et al. 2000) to a final concentration of 3 μM. After incubation for 2 hours at 37 degrees centigrade, the conversion of resazurin to resorufin was measured by fluorescence (excitation at 570 nm and emission at 615 nm). Living cells catalyze dye conversion while cells that lack metabolic activity do not. Percent viability was determined as 2 hour fluorescence, minus background at t=0 hours, normalized to DMSO controls. For detection of luciferase activity, media was removed from plates after the measurement of resazurin conversion, and SteadyLite luciferase reagent (Perkin-Elmer) was added (30 μl/well). Luminescence is detected with a Victor 2-V plate reader (Perkin-Elmer) and normalized to luciferase activity of DMSO control wells alone.

Compounds Described. The following test compounds were obtained commercially: T0901317 (Cayman Chemicals); rockogenin or OR-885 (Steraloids, Newport, R.I.); 5α, 20α, 22α, 25D-Spirostan-3β, 12β-diol-11-one or OR-345 (Steraloids); hyodeoxycholic acid methyl ester or OR-942 and hyodeoxycolic acid or OR-412 (Steraloids); 11-oxo ursolic acid acetate or OR-13571 (Microsource, Gaylordsville, Conn.) and AG-205/33159060 (Specs, Delft, The Netherlands) or OR-2161; OR-133008 (Specs AG-690/40752395); OR-133097 (Specs AG-690/40698971); OR-133099 (Specs AG-690/40699006); OR-133167 (Specs AG-690/40752726); and OR-133171 (Specs AG-690/40752859).

Compounds Synthesized.

The following describes synthesis of a representative antagonist (e.g., OR-1050) and a representative agonist (e.g., OR-12872) to RORγ. All starting materials were commercially available. Related antagonists and agonists, where not purchased commercially, were synthesized by analogous methods.

Abbreviations: $Ac_2O$—acetic anhydride; $NEt_3$—triethylamine; THF—tetrahydrofuran; DMAP—4-Dimethylaminopyridine; EDCl—(3-dimethylaminopropyl)-3-ethyl-carbodiimide hydrochloride; TBSCl—tert-butyl-chloro-dimethyl-silane; DMF—dimethylformamide; TBAF—Tetra-n-butylammonium fluoride.

Synthetic Scheme for OR-1050 where R=Para-nitrophenyl:

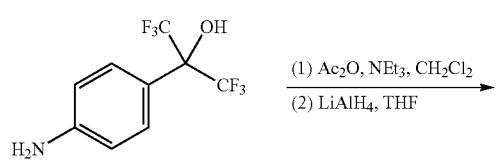

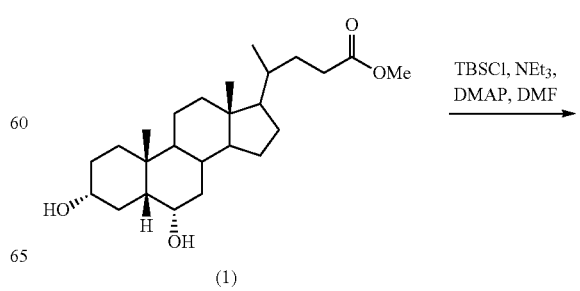

2-(4-Ethylamino-phenyl)-1,1,1,3,3,3-hexafluoro-propan-2-ol

To a solution of 3.0 gm of 2-(4-Amino-phenyl)-1,1,1,3,3,3-hexafluoro-propan-2-ol (Matrix Scientific, Columbia, S.C.) in 30 ml of methylene chloride was added 2.4 ml of triethyl amine, 1.2 ml of acetic anhydride, and 100 mg of dimethylaminopyridine. The mixture was allowed to stir at room temperature for 16 hrs. An additional 2.4 ml of triethyl amine and 1.2 ml of acetic anhydride was added and the mixture was stirred for an additional 6 hrs. The solution was evaporated and purified by column chromatography (1:1 Ethyl Acetate:Hexane) to give 3.1 gm of material that was used in the next step. To this material dissolved in 30 ml of tetrahydrofuran cooled to 0 degrees C. was added 1.6 gm of lithium aluminum hydride. This solution was stirred for 16 hrs and quenched with 1 N sodium hydroxide. This was then extracted with ethyl acetate and dried over anhydrous sodium sulfate. Chromatography gave 2.188 gm of the named product. 1H NMR was consistent with the structure.

N-Ethyl-4-nitro-N-[4-(2,2,2-trifluoro-1-hydroxy-1-trifluoromethyl-ethyl)-phenyl]-benzenesulfonamide (OR-1050)

To a solution of 104 mg 2-(4-Ethylamino-phenyl)-1,1,1,3,3,3-hexafluoro-propan-2-ol in 3 ml of pyridine was added 104 mg 4-Nitro-benzenesulfonyl chloride and 10 mg of dimethylaminopyridine. The mixture was stirred for 16 hrs and then concentrated in vacuo. After chromatography (1:3 Ethyl Acetate:Hexane), 129 mg of the named product was obtained. 1H NMR was consistent with the structure.

Synthetic Scheme for OR-12872

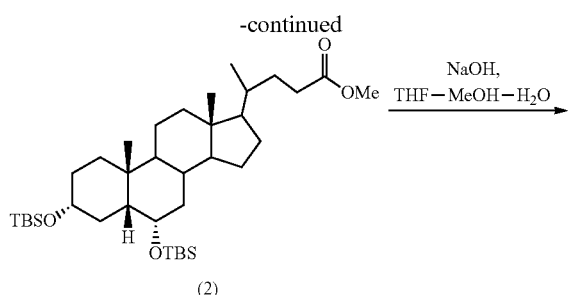

(2)

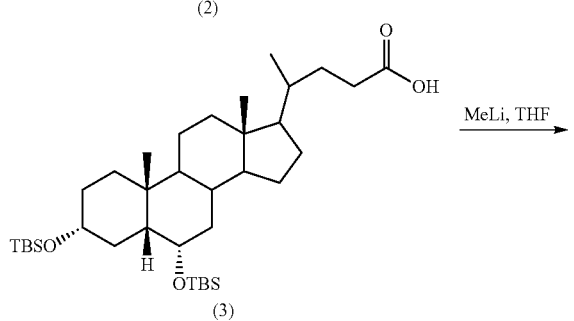

(3)

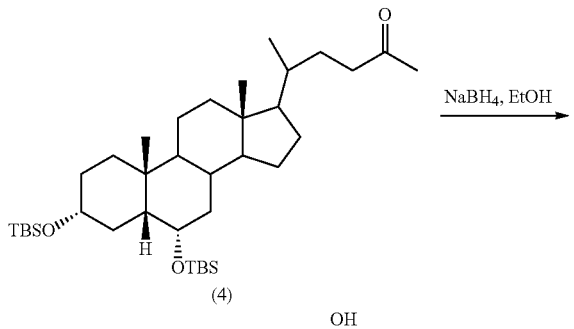

(4)

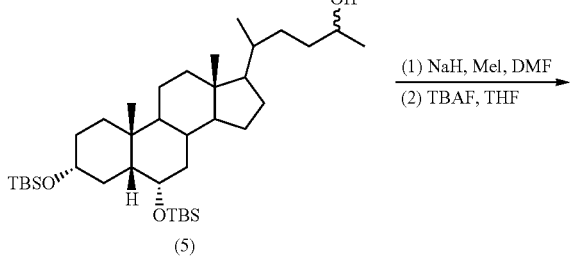

(5)

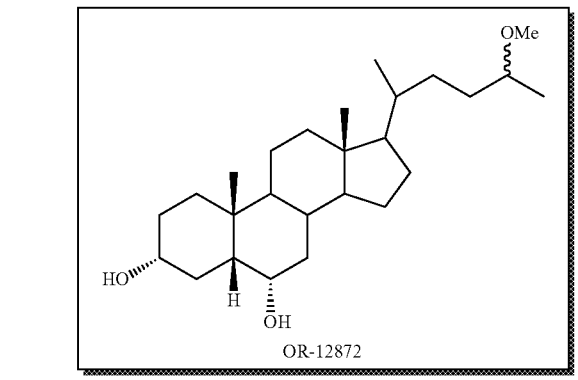

OR-12872

4R-[3R,6R-Bis-(tert-butyl-dimethyl-silanyloxy)-10R,13R-dimethyl-5R-8S-9S-14S-hexadecahydro-cyclopenta[a]phenanthren-17R-yl]-pentanoic acid methyl ester (2)

To a solution of 8.974 gm of hyodeoxycholic acid methyl ester (4R-(3R,6R-Dihydroxy-10R,13R-dimethyl-5R-8S-9S-14S-hexadecahydro-cyclopenta[a]phenanthren-17R-yl)-pentanoic acid methyl ester) (1) (Steraloids, Newport, R.I.) in 60 ml of dimethyl formamide was added 12 ml of triethylamine, 8.3 gm of tert-Butyl-chloro-dimethyl-silane and 270 mg of dimethyl-aminopyridine. The mixture was stirred at room temperature for 16 hrs and concentrated in vacuo. After chromatography (1:9 Ethyl Acetate:Hexane), 13.748 gm of the named product (2) was obtained. 1H NMR was consistent with the structure.

4R-[3R,6R-Bis-(tert-butyl-dimethyl-silanyloxy)-10R,13R-dimethyl-5R-8S-9S-14S hexadecahydro-cyclopenta[a]phenanthren-17R-yl]-pentanoic acid (3)

To a solution of 4-[3,6-Bis-(tert-butyl-dimethyl-silanyloxy)-10,13-dimethyl-hexadecahydro-cyclopenta[a]phenanthren-17-yl]-pentanoic acid methyl ester (9.41 gm) in 15 ml of tetrahydrofuran, 10 ml of methanol and 10 ml of water was added 620 mg of sodium hydroxide. The mixture was then stirred at room temperature for 16 hrs and concentrated in vacuo. After acidification the residue was extracted with ethyl acetate, dried over anhydrous sodium sulfate, filtered and concentrated in vacuo. Chromatography (1:3 Ethyl Acetate:Hexane) gave 8.6 gm of the title compound (3). 1H NMR was consistent with the structure.

5R-[3R,6R-Bis-(tert-butyl-dimethyl-silanyloxy)-10R,13R-dimethyl-5R-8S-9S-14S-hexadecahydro-cyclopenta[a]phenanthren-17R-yl]-hexan-2-one (4)

To a solution of 4-[3,6-Bis-(tert-butyl-dimethyl-silanyloxy)-10,13-dimethyl-hexadecahydro-cyclopenta[a]phenanthren-17-yl]-pentanoic acid (3.419 gm) in 30 ml of tetrahydrofuran at 0 degrees C. was added 7.6 ml of a 1.6 M solution of methyl lithium. The mixture was stirred at 0 degrees C. for 30 min and quenched with 20 ml water followed by 20 ml of 1N hydrochloric acid. The mixture was extracted with ethyl acetate, dried over anhydrous sodium sulfate and concentrated in vacuo. Chromatography (1:9 Ethyl Acetate:Hexane) gave 0.985 gm of the title compound (4). 1H NMR was consistent with the structure.

5R-[3R,6R-Bis-(tert-butyl-dimethyl-silanyloxy)-10R,13R-dimethyl-5R-8S-9S-14S-hexadecahydro-cyclopenta[a]phenanthren-17R-yl]-hexan-2-ol (5)

To a solution of 516 mg of 5-[3,6-Bis-(tert-butyl-dimethyl-silanyloxy)-10,13-dimethyl-hexadecahydro-cyclopenta[a]phenanthren-17-yl]-hexan-2-one in 10 ml of ethanol was added 250 mg of sodium borohydride. The mixture was stirred for 1 hr and concentrated in vacuo, 20 ml of water was added followed by 30 ml of ethyl acetate and 10 ml of 1N hydrochloric acid. The mixture was extracted with ethyl acetate, dried over anhydrous sodium sulfate and concentrated in vacuo. Chromatography (1:9 Ethyl Acetate: Hexane) gave 512 mg of the title compound (5). 1H NMR was consistent with the structure.

17R-(4-Methoxy-1R-methyl-pentyl)-10R,13R-dimethyl-5R-8S-9S-14S-hexadecahydro-cyclopenta[a]phenanthrene-3R,6R-diol (OR-12872)

To a solution of 262 mg of (5) in 6 ml of dimethyl formamide was added 110 ml of methyl iodide followed by 29 mg of a 60% oil dispersion of sodium hydride. The mixture was stirred for 16 hr and concentrated in vacuo. The mixture was extracted with ethyl acetate, dried over anhydrous sodium sulfate and concentrated in vacuo. Chromatography (1:9 Ethyl Acetate:Hexane) gave 257 mg of an intermediate that was dissolved in 10 ml of tetrahydrofuran and 2.4 ml of a 1M tetrahydrofuran solution of tetrabutylammonium fluoride. The mixture was then stirred at room temperature for 16 hrs and then at 60 C. for 2 hrs. After concentration in vacuo and chromatography (1:9 Ethyl Acetate:Hexane), 154 mg of the title compound (OR-12872) was produced. 1H NMR was consistent with the structure.

Compound Nomenclature. Compounds have the following IUPAC names: OR-1048, 4-Bromo-N-ethyl-N-[4-(2,2,2-trifluoro-1-hydroxy-1-trifluoromethyl-ethyl)-phenyl]-benzenesulfonamide; OR-1052, N-Ethyl-4-methyl-N-[4-(2,2,2-trifluoro-1-hydroxy-1-trifluoromethyl-ethyl)-phenyl]-benzenesulfonamide; OR-1050, N-Ethyl-4-nitro-N-[4-(2,2,2-trifluoro-1-hydroxy-1-trifluoromethyl-ethyl)-phenyl]-benzenesulfonamide; OR-1047, 4-Butyl-N-ethyl-N-[4-(2,2,2-trifluoro-1-hydroxy-1-trifluoromethyl-ethyl)-phenyl]-benzenesulfonamide; OR-1031, N-Ethyl-N-[4-(2,2,2-trifluoro-1-hydroxy-1-trifluoromethyl-ethyl)-phenyl]-benzenesulfonamide; T0901317, N-(2,2,2-Trifluoro-ethyl)-N-[4-(2,2,2-trifluoro-1-hydroxy-1-trifluoromethyl-ethyl)-phenyl]-benzenesulfonamide; OR-1030, N-Ethyl-N-[4-(2,2,2-trifluoro-1-methoxy-1-trifluoromethyl-ethyl)-phenyl]-benzenesulfonamide; OR-1046, {Benzenesulfonyl-[4-(2,2,2-trifluoro-1-hydroxy-1-trifluoromethyl-ethyl)-phenyl]-amino}-acetic acid.

OR-12872, 17-(4-Methoxy-1-methyl-pentyl)-10,13-dimethyl-hexadecahydro-cyclopenta[a]phenanthrene-3,6-diol; OR-12866, 17-(4-Methoxy-1,4-dimethyl-pentyl)-10,13-dimethyl-hexadecahydro-cyclopenta[a]phenanthrene-3,6-diol; OR-942, 4-(3,6-Dihydroxy-10,13-dimethyl-hexadecahydro-cyclopenta[a]phenanthren-17-yl)-pentanoic acid methyl ester; OR-12863, 17-(4-Hydroxy-1-methyl-butyl)-10,13-dimethyl-hexadecahydro-cyclopenta[a]phenanthrene-3,6-diol; OR-12870, 5-(3,6-Dihydroxy-10,13-dimethyl-hexadecahydro-cyclopenta[a]phenanthren-17-yl)-hexan-2-one; OR-12868, 4-(3,6-Dihydroxy-10,13-dimethyl-hexadecahydro-cyclopenta[a]phenanthren-17-yl)-pentanoic acid dimethylamide; OR-12864, 17-(4-Methoxy-1-methyl-butyl)-10,13-dimethyl-hexadecahydro-cyclopenta[a]phenanthrene-3,6-diol; OR-12865, 17-(4-Hydroxy-1,4-dimethyl-pentyl)-10,13-dimethyl-hexadecahydro-cyclopenta[a]phenanthrene-3,6-diol; OR-12871, 17-(4-Hydroxy-1-methyl-pentyl)-10,13-dimethyl-hexadecahydro-cyclopenta[a]phenanthrene-3,6-diol; OR-412, 4-(3,6-Dihydroxy-hexadecahydro-cyclopenta[a]phenanthren-17-yl)-pentanoic acid; OR-12867, 4-(3,6-Dihydroxy-hexadecahydro-cyclopenta[a]phenanthren-17-yl)-pentanoic acid methylamide; OR-12869, 4-(3,6-Dihydroxy-hexadecahydro-cyclopenta[a]phenanthren-17-yl)-1-piperidin-1-yl-pentan-1-one;

OR-13571 (11-oxo-ursolic acid acetate), 10-Acetoxy-1,2,6a,6b,9,9,12a-heptamethyl-13-oxo-1,3,4,5,6,6a,6b,7,8,8a,9,10,11,12,12a,12b,13,14b-octadecahydro-2H-picene-4a-carboxylic acid.

The following descriptions are available for two of the natural compounds tested: OR-885 (CAS registry number, 16653-52-4, Rockogenin, 5a, 20α, 22α, 25D-SPIROSTAN-3β, 12β-DIOL, Steraloids catalogue number S0300-000) and OR-345 (5α, 20α, 22α, 25D-SPIROSTAN-3β, 12β-DIOL-11-ONE, Steraloids catalogue number S0400-000).

OR-2161 is N-(4,6-Di-piperidin-1-yl-[1,3,5]triazin-2-yl)-N'-(2-methoxy-3-nitro-benzylidene)-hydrazine (Specs catalog number AG-205/33159060); OR-133008 is 2-{5-[(4-Chloro-phenylamino)-methyl]-4-ethyl-4H-[1,2,4]triazol-3-yl sulfanyl}-N-naphthalen-1-yl-acetamide (Specs AG-690/40752395); OR-133097 is 2-{5-[(3-Chloro-phenylamino)-methyl]-4-ethyl-4H-[1,2,4]triazol-3-ylsulfanyl}-N-naphthalen-1-yl-acetamide (Specs AG-690/40698971); OR-133099 is 2-{4-Ethyl-5-[(3-trifluoromethyl-phenylamino)-methyl]-4H-[1,2,4]triazol-3-ylsulfanyl}-N-naphthalen-1-yl-acetamide (Specs AG-690/40699006); OR-133167 is 2-{5-[(3-Chloro-phenylamino)-methyl]-4-methyl-4H-[1,2,4]triazol-3-ylsulfanyl}-N-naphthalen-1-yl-acetamide (Specs AG-690/40752726); OR-133171 is 2-{5-[(3-Chloro-4-methyl-phenylamino)-methyl]-4-ethyl-4H-[1,2,4]triazol-3-ylsulfanyl}-N-naphthalen-1-yl-acetamide (Specs AG-690/40752859).

Biochemical Assay. GST-RORγ was generated by subcloning the RORγ-LBD into pET-41a, a vector which expresses GST fusion proteins in bacteria. A biochemical assay developed with GST-RORγ purified from bacteria had a poor response to ligand. The receptor was expressed in a baculovirus expression vector (Luckow and Summers 1989) in insect S19 cells. Expression in S19 cells, as an alternative to bacterial expression, was also successfully used to generate RORα LBD in a form suitable for protein crystallization (Kallen, Schlaeppi et al. 2002).

The cloning steps for GST-RORγ were as follows. The mRORγ LBD was excised from Gal4-mRORγ (see above for cloning steps) at BamHI and HindIII sites of Sequence 1 and cloned into the corresponding sites of pET-41a(+) (EMD Biosciences, San Diego, Calif.). A GST-mRORγ fragment was then excised from pET-41a(+) at XbaI and XhoI sites and cloned into a pcDNA3.1vector (Invitrogen, Carlsbad, Calif.) restricted at NheI and XhoI sites. Plasmid GST-mRORγ-pcDNA3.1 was used as a PCR template to generate a GST-mRORγ fragment that was later cloned into pENTR/D-TOPO vector (Invitrogen, Carlsbad, Calif.) by standard cloning techniques recommended by the manufacturer of the vector. The nucleotide sequence of GST-mRORγ is shown below:

```
(GST)
                                        (SEQ ID NO: 17)
ATGTCCCCTATACTAGGTTATTGGAAAATTAAGGGCCTTGTG

CAACCCACTCGACTTCTTTTGGAATATCTTGAAGAAAAATAT

GAAGAGCATTTGTATGAGCGCGATGAAGGTGATAAATGGCGA

AACAAAAAGTTTGAATTGGGTTTGGAGTTTCCCAATCTTCCT

TATTATATTGATGGTGATGTTAAATTAACACAGTCTATGGCC

ATCATACGTTATATAGCTGACAAGCACAACATGTTGGGTGGT

TGTCCAAAAGAGCGTGCAGAGATTTCAATGCTTGAAGGAGCG

GTTTTGGATATTAGATACGGTGTTTCGAGAATTGCATATAGT

AAAGACTTTGAAACTCTCAAAGTTGATTTTCTTAGCAAGCTA

CCTGAAATGCTGAAAATGTTCGAAGATCGTTTATGTCATAAA

ACATATTTAAATGGTGATCATGTAACCCATCCTGACTTCATG

TTGTATGACGCTCTTGATGTTGTTTTATACATGGACCCAATG

TGCCTGGATGCGTTCCCAAAATTAGTTTGTTTTAAAAAACGT

ATTGAAGCTATCCCACAAATTGATAAGTACTTGAAATCCAGC

AAGTATATAGCATGGCCTTTGCAGGGCTGGCAAGCCACGTTT

GGTGGTGGCGACCATCCTCCAAAATCGGAT
```

-continued (linker)
(SEQ ID NO: 18)
GGTTCAACTAGTGGTTCTGGTCATCACCATCACCATCACTCC

GCGGGTCTGGTGCCACGCGGTAGTACTGCAATTGGTATGAAA

GAAACCGCTGCTGCTAAATTCGAACGCCAGCACCTGGACAGC

CCAGATCTGGGTACCGGTGGTGGCTCCGGTGATGACGACGAC

AAGAGTCCCATGGGATATCGGGGATCCGCCCGGGCTGGAATT

CGC (mRORγ LBD)
(SEQ ID NO: 9)
ATTCCCAGTTTCTGCAGTGCCCCAGAGGTACCATATGCCTCT

CTGACAGACATAGAGTACCTGGTACAGAATGTCTGCAAGTCC

TTCCGAGAGACATGCCAGCTGCGACTGGAGGACCTTCTACGG

CAGCGCACCAACCTCTTTTCACGGGAGGAGGTGACCAGCTAC

CAGAGGAAGTCAATGTGGGAGATGTGGGAGCGCTGTGCCCAC

CACCTCACTGAGGCCATTCAGTATGTGGTGGAGTTTGCCAAG

CGGCTTTCAGGCTTCATGGAGCTCTGCCAGAATGACCAGATC

ATACTACTGACAGCAGGAGCAATGGAAGTCGTCCTAGTCAGA

ATGTGCAGGGCCTACAATGCCAACAACCACACAGTCTTTTTT

GAAGGCAAATACGGTGGTGTGGAGCTGTTTCGAGCCTTGGGC

TGCAGCGAGCTCATCAGCTCCATATTTGACTTTTCCCACTTC

CTCAGCGCCCTGTGTTTTTCTGAGGATGAGATTGCCCTCTAC

ACGGCCCTGGTTCTCATCAATGCCAACCGTCCTGGGCTCCAA

GAGAAGAGGAGAGTGGAACATCTGCAATACAATTTGGAACTG

GCTTTCCATCATCATCTCTGCAAGACTCATCGACAAGGCCTC

CTAGCCAAGCTGCCACCCAAAGGAAAACTCCGGAGCCTGTGC

AGCCAACATGTGGAAAAGCTGCAGATCTTCCAGCACCTCCAC

CCCATCGTGGTCCAAGCCGCCTTCCCNCCACTCTATAAGGAA

CTCTTCAGCACTGATGTTGAATCCCCTGAGGGGCTGTCAAAG

TGA

The protein sequence of GST-mRORγ is shown below:

(Gal4 DBD)
(SEQ ID NO: 10)
MKLLSSIEQACDICRLKKLKCSKEKPKCAKCLKNNWECRYSPK

TKRSPLTRAHLTEVESRLERLEQLFLLIFPREDLDMILKMDSL

QDIKALLTGLFVQDNVNKDAVTDRLASVETDMPLTLRQHRISA

TSSSEESSNKGQRQLTVSP (linker)
(SEQ ID NO: 11)
GSARAGIR (mRORγ LBD)
(SEQ ID NO: 12)
IPSFCSAPEVPYASLTDIEYLVQNVCKSFRETCQLRLEDLLRQ

RTNLFSREEVTSYQRKSMWEMWERCAHHLTEAIQYVVEFAKRL

-continued
SGFMELCQNDQIILLTAGAMEVVLVRMCRAYNANNHTVFFEGK

YGGVELFRALGCSELISSIFDFSHFLSALCFSEDEIALYTALV

LINANRPGLQEKRRVEHLQYNLELAFHHHLCKTHRQGLLAKLP

PKGKLRSLCSQHVEKLQIFQHLHPIVVQAAFXPLYKELFSTDV

ESPEGLSK

For baculoviral expression of RORγ, the cDNA fragment of GST-RORγ-LBD, was subcloned from pET-41a into the pENTR/D-TOPO vector using a commercially-available kit (BaculoDirect, Invitrogen). Briefly, GST-RORγ carried by pENTR/D-TOPO was transfected into mono-layer Sf9 cells ($8\times10^5$/well in 6-well plates) by Cellfectin (Invitrogen). Sf9 cells were incubated at 27° C. in a non-humidified incubator for 72 hours. Cell media was collected as P1 viral stock and used to further infect Sf9 cells to generate P2 and P3 virus. Significant signs of infection were observed during generation of P3 virus. A plaque assay was performed to determine the titer of P3 virus and to isolate single plaques. P4 virus was generated from a single plaque and propagated on a larger scale.

Adherent SF9 cells were infected with baculovirus carrying GST-RORγ and were cultured for 72 hours. Sf9 cell were then subject to a brief sonication in a lysis buffer (20 mM phosphate, pH 6.8, 50 mM KCl, 50 mM NaCl, 0.5 mM EDTA, 50% glycerol, 0.001% NP-40 and 1 mM DTT) and centrifuged at 3000 rpm for 15 minutes. GST-RORγ protein represents an estimated 20-30% of total soluble protein in the cytosolic supernatant as determined by SDS-PAGE and immunoblot with anti-GST antibody (Sigma). Some protein remained in an insoluble fraction after centrifugation. We found that addition of RORγ ligands (preferably 5 μM T0901317) in the culture media increased the fraction of GST-RORγ in the cytosolic fraction. Cleared cell lysate was stored at −70° C. and is directly utilized in the coregulatory peptide recruitment assay.

To carry out the biochemical assay, receptor, peptides, and fluorescently-labeled probes to GST and biotin were incubated under these conditions: purified biotinylated peptide K (0.2 μM), 80 nM anti-GST coupled to allophycocyanin (APC), 25 nM streptavidin-R-phycoerythrin (SA-RPE), that specifically binds the biotinylated peptide, 20 mM sodium phosphate, pH 6.8, 50 mM KCl, 50 mM NaCl, 0.5 mM EDTA, 5% glycerol, 0.001% NP-40, and 1 mM DTT were incubated with the Sf9 cell lysate diluted in the range of 1:10 to 1:50, following methods from the literature (Coward, Lee et al. 2001; Drake, Zhang et al. 2002; Lee, Elwood et al. 2002), and incubated at room temperature for 2 hours. The labeled probes anti-GST-APC and SA-RPE were purchased from Prozyme (San Leandro, Calif.). Compounds were added directly from a DMSO solution to a final concentration of 1-2% DMSO. Fluorescence was measured on a Wallac Victor 2 V plate reader equipped with a 670/40 nm filter (Omega Optical, Brattleboro, Vt.) for APC emission (Channel A) and a 600/25 bandpass filter for monitoring the RPE emission (Channel B). The FRET signal is calculated as: (the difference between the ratio of Channel B/Channel A in the presence of an active peptide (such as peptide K) and the Channel A/Channel B ratio in the presence of the corresponding inactive peptide (peptide Kmut))×100 or in the complete absence of peptide.

Results

Members of the RORα, RORβ, and RORγ family of orphan nuclear receptors are generally recognized as having a high basal activity in cell culture systems (Jetten, Kurebayashi et al. 2001). The transcriptional activity of Gal4-mRORγ in CHO cells and in the choriocarcinoma cell line JEG-3 was >20-fold higher than a mutated form of Gal4-mRORγ (E502Q or E/Q). The E/Q mutation inactivates a highly conserved residue of the helix 12 region of the LBD that is required for recruitment of transcriptional coactivators in most well-characterized nuclear receptors (Li, Lambert et al. 2003), and is predicted to abrogate transcription from the RORγ LBD. An assay for detecting RORγ ligands was developed in CHO cells, and about 100,000 individual small molecule compounds from various commercial sources tested in this assay in several formats (e.g., in 96 or 384-well plates, or following 24-hour or 40-hour incubation with test compounds). Two classes of RORγ antagonists are shown below. Structure 1 represents a genus of non-steroidal antagonists in which R1=H, C1-C6 Alkyl, F, Cl, Br, I, NO2; R2=C1-C4 Alkyl; and X=OH. Structure 3 represents a genus of steroidal antagonists in which X=O or is absent (X=H,H). Any antagonist encompassed by these generic structures is within the scope of the present invention. The ability of any such compound, or any other compound, to act as an RORγ antagonist may be easily determined using the assays described herein. Structure 2 represents a genus of steroidal agonists in which X=C(E)(F)(G); wherein E and F are independently selected from H, lower alkyl or E and F taken together form a carbonyl group; G is selected from OH, O-lower alkyl or N(lower alkyl)$_2$. Any agonist encompassed by these generic structures is within the scope of the present invention. The ability of any such compound, or any other compound, to act as an RORγ agonist may be easily determined using the assays described herein.

Figure 3:
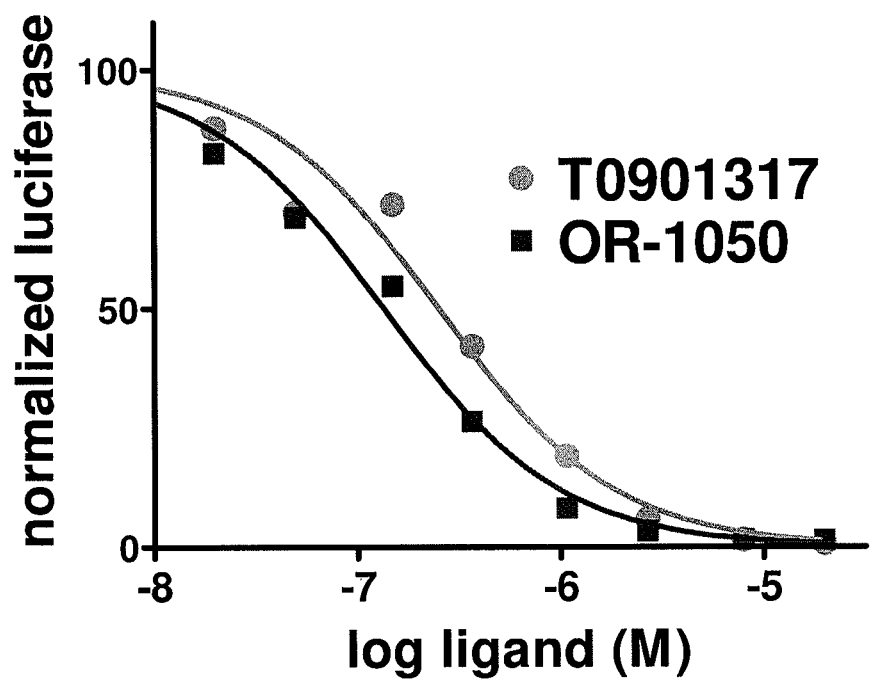
FIG. 3. Dose response of RORγ antagonists in a Chinese Hamster Ovary (CHO) cell assay of transcription. CHO cells were transfected with an expression plasmid encoding a fusion of the DNA-binding domain (DBD) of the yeast transcriptional factor Gal4 with the ligand-binding domain of mouse RORγ (Gal4-mRORγ). A luciferase reporter containing a 5×Gal4 response element at its promoter region was cotransfected with the receptor chimera. T0901317 (Schultz, Tu et al. 2000) and OR-1050 are added in DMSO and each point is the median of triplicate values, normalized to a DMSO-only control.

FIG. 3 shows that two compounds, T0901317 and OR-1050 (Table 1), both inhibit the high basal transcriptional activity of RORγ. In separate studies, we determined that the two compounds had no effects on the transcription of RORα, RORβ or SF-1 as GAL4 hybrids in the same format as the GAL4-RORγ assay. Further, T0901317<10 μM was not cytotoxic to CHO cells while OR-1050 was not cytotoxic at 50 μM. All antagonists and agonists identified in this example were similarly specific for RORγ in the transcriptional assay and were non-cytotoxic to CHO cells at 20 μM or, if not, were non-cytotoxic at a concentration 10-fold greater than the EC$_{50}$ in the transcriptional assay.

Figure 4A:
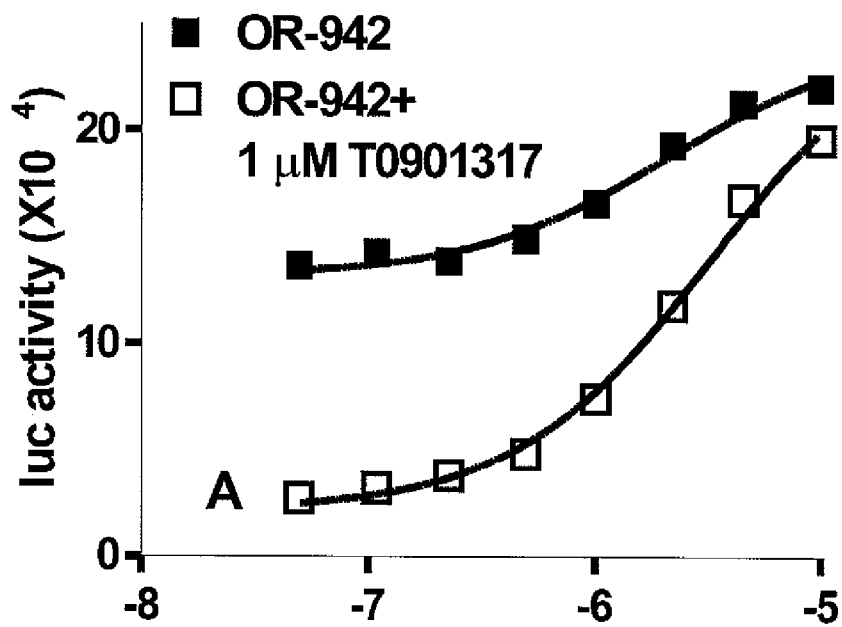
FIGS. 4A-B. Identification and characterization of RORγ agonists. To lower the transcriptional basal activity of RORγ in CHO cells and increase the dynamic range for RORγ activation by agonists, one micromolar of the RORγ antagonist T0901317 (Cayman Chemical, Ann Arbor Mich.) was added to the cell-based assay described in FIG. 3.

Because the basal transactivation activity of GST-RORγ is high, other compounds that bind RORγ and have only a modest effect on transcription when tested alone in cell culture may be overlooked. Some of these compounds could be classified as RORγ agonists. These may activate, rather than repress, RORγ-mediated processes in cells or animals. Accordingly, a screening assay for RORγ agonists was carried out in which one of the RORγ antagonists identified, T0901317, was added to suppress the basal transcriptional activity of GAL4-RORγ. FIG. 4A demonstrates a method for the identification of RORγ agonists. Compounds that only modestly elevated transcription in the absence of T0901317 (for example, the steroidal antagonist OR-942, see Table 2), but induced a much greater elevation in the presence of 1-3 μM T0901317, determined as the ratio between wells containing OR-942 and those lacking OR-942, were further investigated in dose response assays (FIG. 4A).

To further confirm the properties of RORγ agonists and antagonists, a biochemical assay for RORγ was developed. This assay can be used to screen for agonists or antagonists of RORα, RORγ or RORβ. This assay is based on contacting a compound with a labeled, expressed ROR LBD and a peptide that includes residues 710-720 (RTVLQLLLGNP; SEQ ID NO: 2) of human RIP140, and measuring the proximity of the two labels, wherein binding of the labeled peptide identifies the compound as an antagonist and displacement of the labeled peptide identifies the compound as an agonist.

Figure 4B:
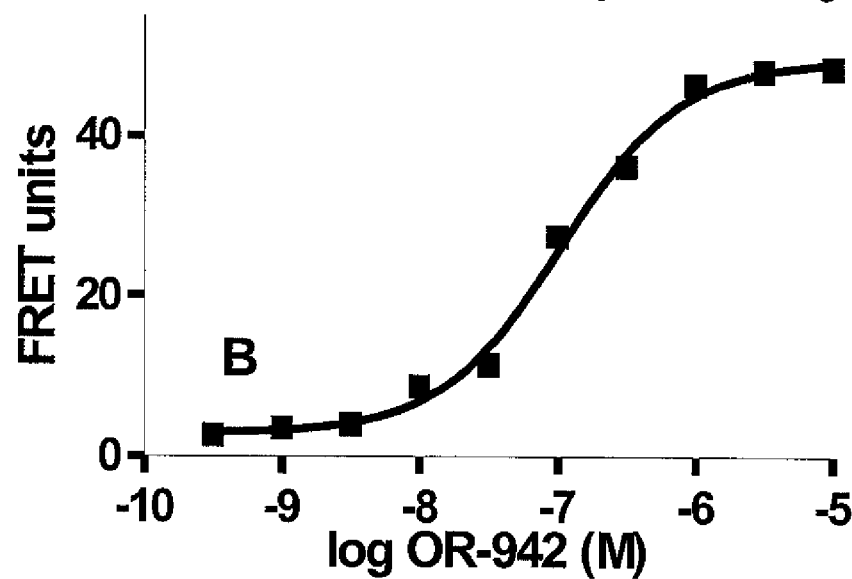
Figure 5:
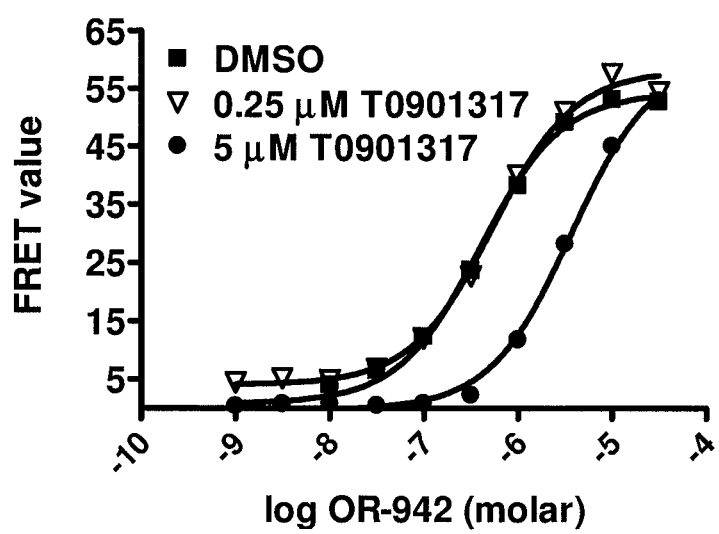
FIG. 5. The RORγ antagonist T0901317 has the properties of a competitive antagonist to OR-942. A dose response of the RORγ agonist OR-942 was carried out in the biochemical assay with GST-RORγ and peptide K. The effect of the antagonist T0901317 is to shift the estimated $EC_{50}$ of OR-942 from 0.4 μM to 4 μM, consistent with competition for a single binding site on RORγ. Each point is the median of triplicate values.

In FIG. 4B, the addition of OR-942 causes the recruitment of peptide K (ERRTVLQLLLGNPTK; SEQ ID NO: 4), a 15-mer identical to amino acid residues 708-722 of transcriptional coregulatory protein human RIP140 (Iannone, Consler et al. 2001), to the RORγ LBD and increases the FRET signal. In the presence of OR-942, T0901317 depresses the FRET signal. Further, T0901317 causes a rightward shift in the dose-response curve for OR-942 (FIG. 5) as would be expected if both compounds compete for the same binding site.

A modified coregulatory peptide was identified for the biochemical assay, peptide K1 (ERRTVLQLLLGNSNK; SEQ ID NO: 3). In addition to its modified sequence, the peptide K1 reagent is attached to biotin by a six carbon linker that may facilitate better accessibility of biotin with streptavidin in the peptide/receptor complex. K1 interacts with GST-mRORγ in the absence of agonist, and therefore we also used the biochemical assay in this format in some of these experiments. In K1, the N-terminal biotin is linked to the first amino acid via 6-aminohexanoic acid (AHC), which is introduced by using Fmoc-6-aminohexanoic acid (CAS NO: 88574-06-5) during peptide synthesis. In peptide K, the N-terminal biotin is directly linked to the first amino acid without any linker.

Figure 6:
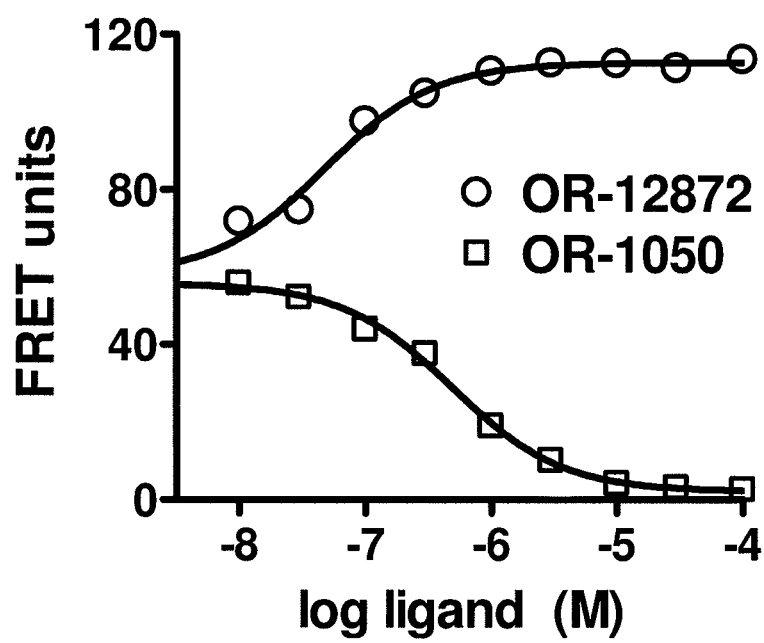
FIG. 6. Simultaneous characterization of an RORγ agonist and antagonist in the biochemical assay for RORγ. The activities of OR-1050 and OR-12872 were compared in a coregulatory peptide recruitment assay that uses peptide biotinylated K1 (from RIP140 of rat) instead of peptide K (from RIP140 of human). The sequence of peptide K1 is ERRTVLQLLLGNSNK (SEQ ID NO: 3). The mutated form of the K1 peptide (K1mut, ERRTVLQLVVGNSNK; SEQ ID NO: 6) was used as a control. The biotin was separated from the K1 and K1mut N-terminus by an aminohexanoic acid linker. The combination of GST-RORγ and peptide K1 has a significant FRET value in the absence of added ligand, and this enables characterization of both agonist and antagonist in the same assay format. Values are the average of duplicate measurements.

As shown in FIG. 6, this assay could be used to characterize both an agonist (OR-12872) and an antagonist (OR-1050) independently under the same assay conditions. The methods illustrated in FIG. 5 and FIG. 6 may also be modified to allow high throughput screening of RORγ agonists and antagonists with the coregulatory peptide recruitment assay.

A number of analogs of T0901317 and OR-1050 were synthesized and compared in the transcriptional and biochemical assays for RORγ (Table 1). These findings showed that the rank order of potency of the series of related molecules was similar in the two assays. Further, several analogs of OR-942 were also synthesized, including OR-12872, an agonist with potency less than 100 nM in the biochemical assay (Table 2). The rank order of potency of these compounds was also similar in the transcriptional and biochemical assays. In one embodiment, the RORγ antagonist is not T0901317.

TABLE 1

The biochemical assay was carried out in the presence of mRORγ and peptide K1.

(Structure 1)

| Non-steroidal analogues of T0901317 (see Structure 1) | | | Assay EC$_{50}$ in micromolar at mRORγ | |
|---|---|---|---|---|
| | X | R1 | R2 | Transcriptional | Biochemical |
| OR-1048 | OH | Br | Me | 0.12 | 0.42 |
| OR-1052 | OH | Me | Me | 0.21 | 0.89 |

TABLE 1-continued

| | | | | | |
|---|---|---|---|---|---|
| OR-1050 | OH | NO2 | Me | 0.26 | 0.9 |
| T0901317 | OH | H | CF3 | 0.54 | 1.2 |
| OR-1031 | OH | H | Me | 1.4 | 3.5 |
| OR-1047 | OH | nBu | Me | 3.6 | 5.8 |
| OR-1030 | OMe | H | H | >20 | >100 |
| OR-1046 | OH | H | CO2H | >20 | >100 |

TABLE 2

(Structure 2)

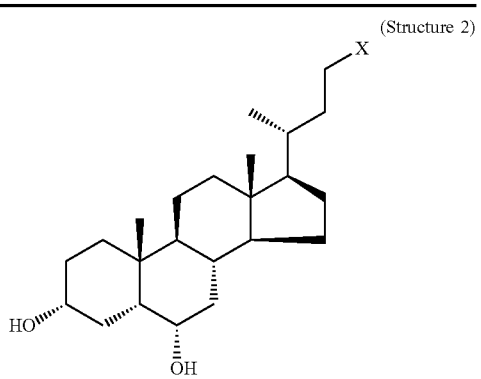

| Analogues of OR-942 (see Structure 2) | | EC50 in micromolar at mRORγ | |
|---|---|---|---|
| | X | Transcriptional | Biochemical |
| OR-12872 | CH(Me)OMe | 0.44 | 0.052 |
| OR-12866 | C(Me)2OMe | 0.56 | 0.14 |
| OR-942 | CO2Me | 1.5 | 0.12 |
| OR-12863 | CH2OH | 4.1 | 0.67 |
| OR-12870 | C(=O)Me | 4.1 | ND |
| OR-12868 | C(=O)NMe2 | 5.2 | 0.56 |
| OR-12864 | CH2OMe | 6 | 0.23 |
| OR-12865 | C(Me)2OH | 8.3 | 0.21 |
| OR-12871 | CH(Me)OH | 8.3 | 0.25 |
| OR-412 | CO2H | >20 | >100 |

TABLE 2-continued

| | | | |
|---|---|---|---|
| OR-12867 | C(=O)NHMe | >20 | ND |
| OR-12869 | C(=O)N(c-C5H10) | >20 | ND |

Derivatives of hyodeoxycholic acid methyl ester (OR-942) were evaluated in the transcriptional assay for RORγ and in the biochemical assay using biotinylated peptide K as the coregulatory peptide.
In the transcriptional assay, antagonist OR-376 (1.5 μM) was added to reduce the basal transcriptional activity or RORγ thus to increase the dynamic range of the agonist effect. $EC_{50}$ values were estimated by fitting the data to a sigmoidal curve (GraphPad, Prism, San Diego, CA).
In the biochemical assay, the compounds induce association between the RORγ LBD and peptide K.
The $EC_{50}$ of the biochemical assay was determined by the concentration of compound required to elevate the baseline by 50% of estimated maximum FRET signal for the individual compound after fitting data to a sigmoidal dose response curve.

In addition, several other RORγ antagonists were identified, including the related terpenes OR-345 and OR-885 (rockogenin) in Table 3. The natural compound OR-13571 (11-oxo ursolic acid acetate), is illustrated in Tables 4A and 4B. Further, the structurally-distinct synthetic compound OR-2161 was also examined in RORγ assays.

TABLE 3

(Structure 3)

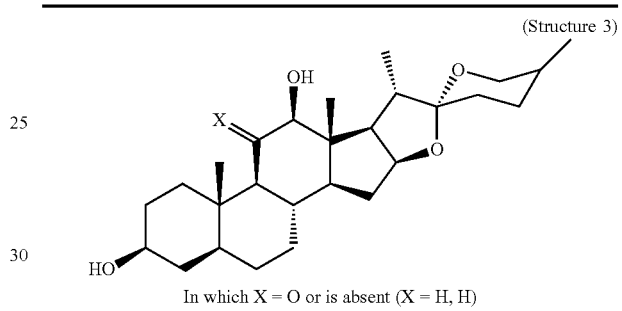

In which X = O or is absent (X = H, H)

| Steroidal Antagonists | | Assay $EC_{50}$ in micromolar | |
|---|---|---|---|
| | X | transcriptional | biochemical |
| OR-885 | H,H | 0.2 | 2.5 |
| OR-345 | O | 5 | 12.7 |

The biochemical assay was carried out in the presence of peptide K and 1 μM OR-942 to elevate the assay baseline.
The $EC_{50}$ of the biochemical assay was determined by the concentration of compound required to inhibit the OR-942 baseline by 50% after fitting data to a sigmoidal dose response curve.

TABLE 4A

RORγ antagonists.

| Compound ID | Structure | $EC_{50}$ Transcriptional | $EC_{50}$ Biochemical |
|---|---|---|---|
| OR-13571 | 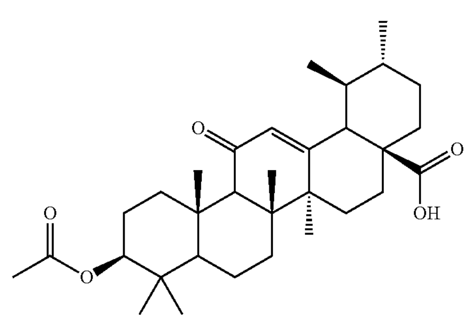 | 0.27 | 1.2 |

TABLE 4A-continued

RORγ antagonists.

| Compound ID | Structure | EC$_{50}$ Transcriptional | EC$_{50}$ Biochemical |
| --- | --- | --- | --- |
| OR-2161 | 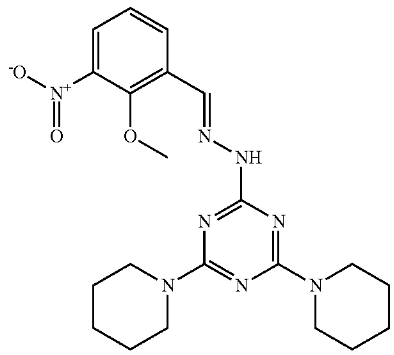 | 0.33 | 4.5 |
| OR-133008 | 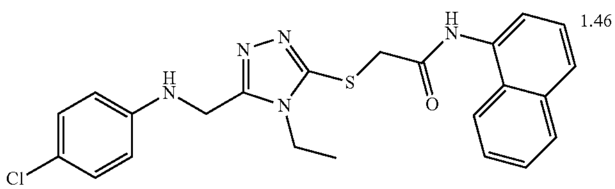 | 1.46 | 1.61 |
| OR-133097 | 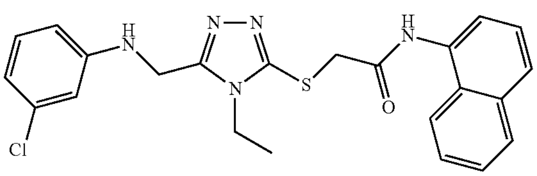 [SMILES: CCn1c(CNc2cccc(Cl)c2)nnc1SCC(=O)Nc1cccc2ccccc12] | 1.44 | 1.34 |
| OR-133099 | 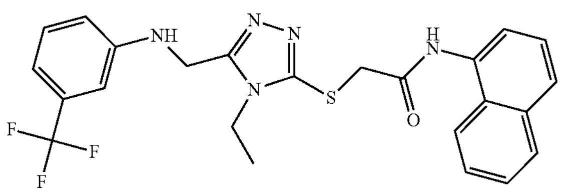 [SMILES: CCn1c(CNc2cccc(C(F)(F)F)c2)nnc1SCC(=O)Nc1cccc2ccccc12] | 1.04 | 1.33 |
| OR-133167 | 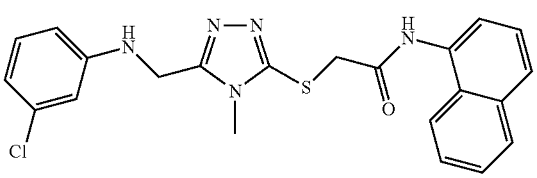 [SMILES: Cn1c(CNc2cccc(Cl)c2)nnc1SCC(=O)Nc1cccc2ccccc12] | 3.3 | 3.4 |
| OR-133171 | 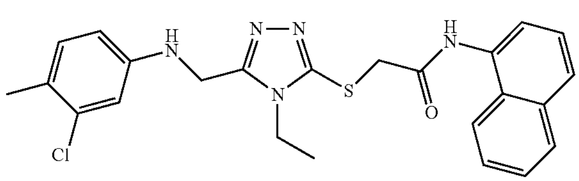 [SMILES: CCn1c(CNc2ccc(C)c(Cl)c2)nnc1SCC(=O)Nc1cccc2ccccc12] | 0.49 | 0.44 |

Biochemical assays were carried out in the presence of peptide K1.
No agonist was present.
OR-13571 is 11-oxo ursolic acid acetate.
Values are medians of two or more assays.

TABLE 4B

OR-52 and analogues of OR-52.

Structure 4

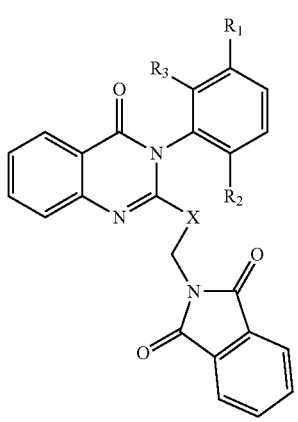

| Compounds (see Structure 4) | | | | Assay EC$_{50}$ in micromolar | |
|---|---|---|---|---|---|
| | X | R1 | R2 | R3 | Transcriptional | Biochemical |
| OR-52 | CH2CH2 | CF3 | H | H | 5.8 | 3.5 |
| OR-32286 | CH2 | CF3 | H | H | >20 | >100 |
| OR-32268 | CH2CH2 | CH3 | H | H | 13.5 | 8.9 |
| OR-32281 | CH2CH2 | Cl | Cl | H | 3.7 | 5.8 |
| OR-32288 | CH2CH2 | CH3 | H | CH3 | >20 | 52.2 |

Biochemical assays were carried out in the presence of peptide K1.
No agonist was present.

Further, many of the compounds listed above were evaluated in a transcriptional assay for hRORγ. As shown in Table 4C, the EC$_{50}$ values were comparable for most compounds tested, except for OR-885, which was significantly less potent at hRORγ, and the analogs of OR-133008, which also were more potent at mRORγ than at hRORγ.

TABLE 4C

Potency of RORγ antagonists in a transcriptional assay of human RORγ.

| Compound | EC$_{50}$ (μM) |
|---|---|
| OR-885 | 5.1 |
| T0901317 | 1.1 |
| OR-1050 | 0.4 |
| OR-2161 | 1.0 |
| OR-13571 | 0.2 |
| OR-133008 | 6.8 |
| OR-133097 | 5.0 |
| OR-133099 | 2.4 |
| OR-133167 | 9.4 |
| OR-133171 | 1.7 |

These findings demonstrate that a range of ligands to RORγ may be identified by receptor screening. The example also illustrates that a series of agonists and a series of antagonists, each covering a wide range of potencies, will have consistent rank order of potencies in two mechanistically separate assays for the same target (e.g. mRORγ). Collectively, these findings strongly imply binding of these ligands to the RORγ LBD. The most potent compounds, both agonists and antagonists, are also useful for characterization of RORγ-mediated effects in target cells

Example 2

It is not unusual for a single compound to interact with receptors from different subfamilies within the nuclear receptor superfamily (Laudet 1999). Nuclear receptor cross-reactivity is sufficiently common that it must be accounted for in a program of ligand design and characterization. An example of such a crossreactive ligand is TTNPB, which binds the retinoic acid receptors (RARα, RARβ, and RARγ) from the NR1B subfamily and the farnesoid X-receptor FXR (Zavacki, Lehmann et al. 1997) in subfamily NR1H. Other examples are the estrogen receptor (NR3A) ligands diethylstilbestrol (DES), tamoxifen (TAM), and 4-hydroxytamoxifen (4-OHT) which bind the estrogen-related receptor ERRγ (NR3B3) (Coward, Lee et al. 2001). Therefore, transcriptional assays were developed to characterize RORγ ligands at several of the other major nuclear receptors.

Methods

Table 5 lists details of construction of Gal4 hybrids with the following nuclear receptor LBDs. The positive control compounds for transcriptional assays (Table 6) are dexamethasone, dihydrotestosterone, 1,25 (OH)$_2$ Vitamin D$_3$, progesterone, chenodeoxycholic acid (CDCA), TTNPB ((E)-4-[2-(5,6,7,8-tetrahydro-5,5,8,8-tetramethyl-2-naphthalenyl)-1-propenyl]benzoic acid), 9-cis retinoic acid, 17β-estradiol, and bezafibrate (from Sigma, St. Louis, Mo.) and T0901317, rosiglitazone and WY14643 from Cayman Chemicals. The transcriptional assays were carried out as in Example 1.

TABLE 5

The following nuclear receptor LBDs were cloned in pFA-CMV for expression as Gal4 hybrids. Receptors are described by common names found in the literature, by a Unified Receptor Nomenclature system (Laudet 1999), and by species of origin (h = human or m = mouse) and a trivial name or abbreviation. The range of amino acids included in the LBD is shown along with the cloning site in pFA-CMV. The amino acid range corresponds, in most cases, to the most common splicing isoform of the receptor. The final amino acid corresponds in each case to the C-terminal residue. Receptors were subcloned into pFA-CMV by PCR using primers containing the restriction enzyme sites shown. The methods are well known to those skilled in the art and constructs similar to these have been widely reported in the scientific literature.

| Common Name of Receptor | Unified Receptor Nomenclature | Species & trivial name | Amino Acid range | cloning sites in pFACMV |
|---|---|---|---|---|
| glucocorticoid receptor | NR3C1 | mGR | 524-793 | BamHI, KpnI |
| androgen receptor | NR3C4 | hAR | 646-919 | BamHI, XbaI |
| Vitamin D receptor | NR1I1 | hVDR | 90-427 | BamHI, HindIII |
| Liver X receptor alpha | NR1H3 | mLXRα | 172-455 | BamHI, XbaI |
| progesterone receptor | NR3C3 | hPR | 687-933 | XbaI, KpnI |
| PPAR-gamma | NR1C3 | hPPARγ | 175-477 | XbaI, KpnI |
| farnesoid X receptor | NR1H4 | hFXR | 192-473 | BamHI, XbaI |
| retinoic acid receptor alpha | NR1B1 | hRARα | 156-462 | BamHI, HindIII |
| retinoid X receptor alpha | NR2B1 | hRXRα | 203-462 | EcoRI, HindIII |
| PPAR-alpha | NR1C1 | hPPARα | 166-468 | BamHI, HindIII |
| PPAR-delta | NR1C2 | hPPARδ | 138-441 | BamHI, HindIII |
| Estrogen receptor-alpha | NR3A1 | hERα | 249-595 | BamHI, KpnI |

TABLE 6

Crossreactive receptor assays for RORγ ligands.

| | Standard | Standard Ligands | | RORγ Ligands | | | | | | |
|---|---|---|---|---|---|---|---|---|---|---|
| | Ligand | Efficacy | Potency | T0901317 | OR-1050 | OR-885 | OR-13571 | OR-12872 | OR-2161 | OR-133008 |
| mGR | Dexamethasone | 35X | ++++ | − | − | − | − | − | − | − |
| hAR | dihydro-testosterone | 8X | ++++ | − | − | − | − | − | − | − |
| hVDR | 1,25 Vitamin D3 | 68X | ++++ | − | − | − | − | − | − | − |
| mLXRα | T0901317 | 120X | ++ | ++ | + | − | − | − | − | − |
| hPR | Progesterone | 6X | ++++ | − | − | − | − | − | − | − |
| hPPARγ | Rosiglitazone | 50X | +++ | − | − | − | − | − | − | − |
| hFXR | CDCA | 5X | ++ | + | − | − | − | − | − | − |
| hRARα | TTNPB | 18X | ++++ | − | − | − | − | − | − | − |
| hERα | 17β-estradiol | 40X | ++++ | − | − | − | − | − | − | − |
| hRXRα | 9-cis-retinoic acid | 180X | +++ | − | − | − | − | − | − | − |
| hPPARα | WY14643 | 6X | * | − | − | − | − | − | − | − |
| hPPARδ | Bezafibrate | 10X | * | − | − | − | − | − | − | − |

Potency indicates EC50 values in μM:
++++ (EC50 < 0.01),
+++ (0.01-0.1),
++ (0.1-1),
+ (1-10) and
− (>10).
*$EC_{50}$ values of standard ligands for PPARα and PPARδ are >>20 μM. Efficacy = activity of standard ligand at 20 μM. The RORγ ligands show no significant activity at 20 μM in assays for PPARα and PPARδ.

Results

Among the RORγ ligands identified in studies described in Example 1, one of the compounds, T0901317, was previously shown to activate LXRα and LXRβ (Schultz, Tu et al. 2000). A transcriptional assay for LXRα, using a Gal4-LXRα hybrid, was implemented in order to compare RORγ ligand potencies. In addition to LXRα, transcriptional assays for a number of other major nuclear receptors were developed. In Table 6, several of the RORγ ligands described in Example 1 were characterized against these receptors. Confirming published data on T0901317 (Schultz, Tu et al. 2000; Houck, Borchert et al. 2004), we found that T0901317 activates LXR and FXR (Table 6). At the same time, a number of other RORγ antagonists, such as OR-12872, OR-885, OR-13571, OR-133008, and OR-2161 were shown to be selective for RORγ within this receptor family.

TABLE 7

Comparative pharmacology of RORγ antagonists at RORγ and LXRα. Compound structures are presented in Table 1, and RORγ pharmacology is taken from Table 1. Activity in the LXRα transcriptional assay is the estimated maximum elevation of luciferase activity, based on a sigmoidal dose response curve, with respect to T0901317.

| RORγ antagonists | Assay $EC_{50}$ in micromolar at mRORγ | | Transcriptional Assay of LXRα | |
|---|---|---|---|---|
| | Transcriptional | Biochemical | activity | $EC_{50}$ |
| OR-1048 | 0.12 | 0.42 | >80% | 0.57 |
| OR-1052 | 0.21 | 0.89 | >80% | 0.81 |
| OR-1050 | 0.26 | 0.9 | >80% | 1.5 |
| T0901317 | 0.54 | 1.2 | 100% | 0.14 |
| OR-1031 | 1.4 | 3.5 | >80% | 1.4 |
| OR-1047 | 3.6 | 5.8 | <5% | >20 |
| OR-1030 | >20 | >100 | <5% | >100 |
| OR-1046 | >20 | >100 | <5% | >100 |

In Table 7, several analogs of T0901317 were compared in transcriptional assays for RORγ and LXRα. The binding pockets of LXRα and LXRβ are very similar in structure and have closely similar affinities to a range of ligands (Svensson, Ostberg et al. 2003). Hence, the LXRα assay is assumed to be representative of both receptors. A number of derivatives of T0901317 were synthesized. As can be seen in Table 7, compounds with a wide range of specificity were identified, including several that are more specific for RORγ than LXRα, including OR-1048, OR-1050, OR-1052 and OR-1047.

The importance of this example is two-fold. First, selective RORγ ligands can be identified that lack obvious cross-reactivity with other nuclear receptors. Secondly, the SAR of compounds in the T0901317 series differ between RORγ and LXRα, suggesting that ligands can be designed from this series that retain RORγ potency and have better separation between the two targets.

In one embodiment, the RORγ antagonist is at least 20-fold more potent as an RORγ antagonist than as an LXR agonist. In other embodiments, the RORγ antagonist is at least about 30-fold, 40-fold, 50-fold, 75-fold, 100-fold, 150-fold, 200-fold, 250-fold, 300-fold, 400-fold, 500-fold, 600-fold, 700-fold, 800-fold, 900-fold, or 1,000-fold more potent as an RORγ antagonist than as an LXR agonist.

Ligands to LXR have anti-inflammatory effects that may make them active in animal models of autoimmune disease (Zelcer and Tontonoz 2006). Recently, T0901317 was shown to inhibit the development of murine EAE (Hindinger, Hinton et al. 2006). It is not known what proportion of the therapeutic effect of T0901317 in the mouse model of EAE is due to RORγ antagonism as opposed to LXR activation. However, strong genetic and pharmacological data demonstrate that activation of LXR causes hypertriglyceridema and triglyceride accumulation in liver. Specifically, in mice lacking the LXRα and LXRβ receptors, T0901317 has no effect on liver triglyceridemia (Schultz, Tu et al. 2000). Other LXR ligands have been tested in cynomolgus monkey and hamster (Groot, Pearce et al. 2005), and these ligands were shown to elevate serum triglycerides and serum LDL. The importance of this example is that it provides methodology to eliminate various forms of LXR-mediated hyperlipidemic activity from the T0901317 and OR-1050 series of compounds while retaining the ability to inhibit $T_H$-17 differentiation.

Example 3

The differentiation of purified naïve murine CD4+ splenic T cells into $T_H$-17 cells in cell culture is simulated by a combination of the cytokines TGFβ and IL-6 or inhibited by the cytokine IFN-γ (Mangan, Harrington et al. 2006; Veldhoen, Hocking et al. 2006). This is not the only differentiation pathway available to naïve CD4+ T cells (FIG. 1). For example, IL-12 stimulates the differentiation of $T_H$1 cells in the same system. The effects of continuous treatment with RORγ agonists and antagonists on $T_H$1 and $T_H$-17 differentiation were investigated. This example demonstrates that small molecule ligands to RORγ regulate $T_H$-17 T cell differentiation. In these experiments, a $T_H$-17 cell was identified by cell surface staining for CD4 and intracellular staining with a labeled antibody to IL-17. In particular, we observe that antagonists to RORγ inhibit $T_H$-17 cell differentiation but have no consistent effect on the differentiation of murine $T_H$1 cells (that are CD4+IFNγ+ but do not express IL-17). The inhibitory effect on $T_H$-17 cells has been observed with four different antagonists that are each structurally distinct (that is, they are not analogs of one another). Further, supporting the conclusion that inhibition of RORγ activity in naïve CD4+ T cells by an RORγ antagonist will inhibit $T_H$-17 differentiation, we show that an agonist to RORγ reverses antagonist inhibition of $T_H$-17 cell differentiation and independently enhances $T_H$-17 cell formation. These results indicate that the RORγ ligands described in the example act specifically through the RORγ LBD in the differentiating $T_H$-17 cell.

Methods

Antibodies and Cytokines. The following reagents were selected for characterization of mouse lymphocytes. FITC anti-IFNγ (XMG1.2), PE anti-CD62L (MEL-14), APC anti-CD4 (RM4-5), FITC anti-CD4 (RM4-5), PE anti-CD8 (53-6.7), APC anti-CD25 (PC61), biotinylated anti-CD25 (PC61.5), Cy5.5 anti-CD44 PE-(IM7) were from eBioscience (San Diego, Calif.). PE anti-IL-17 (TC11-18H10.1) was from BD Biosciences (San Diego, Calif.). TGF-β and IL-6 were from Sigma. IL-12 was from PeproTech (Rocky Hill, N.J.).

Purification of Naïve (CD4+CD62L+CD25−) CD4 Cells. Spleens of 5-7 week old outbred ICR(CD-1, Harlan Labs) mice were gently minced with two 18-gauge needles in PBS buffer supplemented with 2.5 mM $MgCl_2$, 0.5 mM $CaCl_2$ and 25 ug/ml DNAse I. A single cell suspension of splenocytes was triturated with a 5-ml pipet and passed through a 40 μm nylon mesh filter. Splenocytes were spun down at 300×g for five minutes and resuspended in buffer containing PBS, 2% heat-inactivated FCS and 2 mM EDTA. Naïve T cells were purified from splenocytes using a CD4+CD62L+ magnetic bead T cell Isolation Kit from Miltenyi Biotec (Auburn, Calif.) in two steps. First, CD4− cells were removed by negative selection with biotinylated antibodies to CD8a, CD45R, CD11b, CD49b, and Ter119 (supplied by the manufacturer) and to CD25 (biotinylated PC61), added at the time of isolation. The flow through, predominantly CD4+ cells, was directly labeled with anti-CD62L microbeads and enriched on a magnetic column to about 93% purity, as determined by staining for CD4, CD62L, and CD25.

Stimulation and Culture of $T_H$-17 Cells. Purified CD4+CD62L+ T cells were plated in 24-well plates with 2-4×10⁵ cells in 700 ul volume of RPMI 1640 media containing 10% heat-inactivated FCS, 100 IU penicillin, 100 μg/ml streptomycin, 1×non-essential amino acids, 1 mM pyruvate, 2 mM glutamine, and 50 μM β-mercaptoethanol (Veldhoen, Hocking et al. 2006). T cells were stimulated with exogenous cytokines and anti-CD3/anti-CD28 conjugated Dynabeads (Dynal Biotech, Oslo) at a 1:1 ratio of beads to cells. Exogenous cytokines used were: 4 ng/ml TGF-β, 20 ng/ml of IL-6, or 10 ng/ml IL-12. RORγ agonist and antagonist ligands, dissolved in DMSO, were added directly to cell cultures, to a final concentration of 0.01%. Cytokines and RORγ ligands were added immediately after cell plating.

Cell Staining and Flow Cytometry. To determine intracellular cytokine production, exogenous cytokines were removed by centrifugation and cultures treated with 500 ng/ml phorbol 12,13 dibutyrate (PdBu), 500 ng/ml ionomycin, and 1 μg/ml brefeldin A for 4-6 hours to stimulate cytokine production while preventing secretion as described (Veldhoen, Hocking et al. 2006) and washed again. Cells were then fixed, permeabilized and stained for intracellular cytokines using commercial reagents (eBioscience, San Diego). Cells were also stained for the cell surface markers CD4 and CD8. Flow cytometry analysis was performed on a FACSCalibur (Becton Dickinson) and the data were analyzed using FlowJo Software (Tree Star, Inc).

ELISA for IL-17. ELISA kits for mouse IL-17 and human IL-17 were from eBioscience (San Diego, Calif.). ELISA assays were performed following the manufacturer's protocol. Certain samples were diluted 20-fold to avoid maximization of enzymatic signals. For mouse IL-22 ELISA, antibodies and standards were from Antigenix America (Huntington Station, N.Y.) and accessory components were from eBioscience. The IL-22 assay protocol was similar to that of the IL-17 assays.

Results

Mouse $T_H$-17 cells can be induced to differentiate from naïve CD4+ T cells in the presence of TGFβ and IL-6 (Veldhoen, Hocking et al. 2006). At the same time, $T_H$1 differentiation is suppressed. Critical steps in this protocol are: (i) purification of naïve CD4+ cells to remove potentially inhibitory activated T cells, such as $T_H$1 cells, or T regulatory (Treg) cells, (ii) activation of T cells by cross-linking CD3 and CD28, and (iii) incubation with TGFβ and IL-6 to induce $T_H$-17 differentiation. Protocols for $T_H$-17 differentiation have been reported by several laboratories (Bettelli, Carrier et al. 2006; Mangan, Harrington et al. 2006; Veldhoen, Hocking et al. 2006). The percentage of differentiated cells is determined by intracellular staining for IL-17 and IFN-γ, markers of $T_H$-17 and $T_H$1 cells respectively (Park, Li et al. 2005). A $T_H$-17 differentiation assay provides a cell-based model to demonstrate RORγ antagonist function. We predicted that OR-1050, OR-885, OR-13571, and OR-2161 should inhibit $T_H$-17 differentiation and/or IL-17 release and that this inhibitory effect could be reversed by the potent RORγ agonist OR-12872.

Naïve CD4+ T cells were isolated from splenocytes of 5-8 wk old CD-1 mice and CD4+CD62L+ cells with approximately 93% purity selected with magnetic beads. We estimated that the population of Tregs (Itoh, Takahashi et al. 1999) in the purified cells, as estimated by the percentage of CD25+CD44+ cells, was about 1-1.5% as compared to 5% in total splenocytes. IL-12 treatment of the naïve T cells stimulates $T_H$1 differentiation as shown by the high percentage of IFNγ positive cells, while the combination of TGFβ1 and IL-6 induced the formation of 4% IL-17-producing cells (Table 8). As reported, the $T_H$1 (IFNγ+) and $T_H$-17 (IL-17+) phenotypes were mutually exclusive (see also FIG. 8).

Further, both IL-6 and TGFβ were required to fully induce the $T_H$-17 phenotype as reported in the scientific literature (Bettelli, Carrier et al. 2006; Mangan, Harrington et al. 2006; Veldhoen, Hocking et al. 2006). Finally, we observed that the IL-17+ cells were >97% CD4+.

TABLE 8

IL-17- or IFNγ-producing cells are differentiated from naïve CD4 cells in the presence of exogenous cytokines. Cells are stained for IL-17 or IFN-γ and quantitated by FACS analysis. Data are shown as mean ± SD of the percentage of IL-17 or IFNγ-producing cells in total cell populations after 5 days in culture. Less than 0.02% of total cells appear to express both cytokines.

|  | IL-17 (%) | IFNγ (%) |
|---|---|---|
| No cytokine | 0.21 ± 0.00 | 2.50 ± 0.40 |
| IL-12 (10 ng/ml) | 0.09 ± 0.01 | 39.6 ± 2.44 |
| TGFβ1 (4 ng/ml) | 0.21 ± 0.02 | 0.32 ± 0.05 |
| IL-6 (20 ng/ml) | 1.20 ± 0.04 | 3.42 ± 0.08 |
| TGFβ1 + IL-6 | 4.53 ± 0.18 | 2.14 ± 0.18 |

Figure 7:
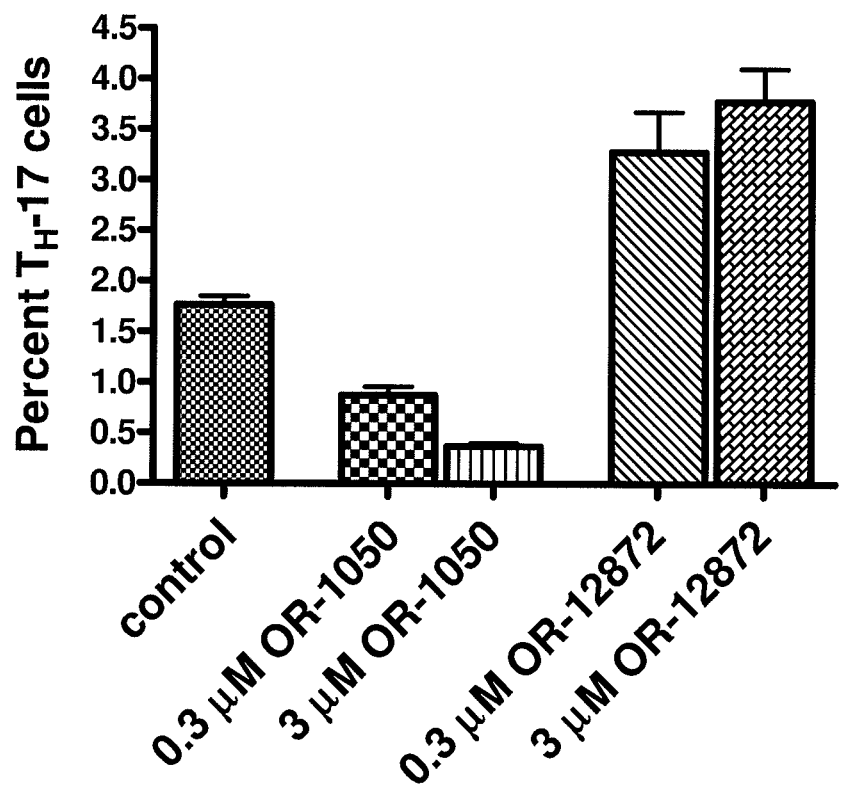
FIG. 7. Regulation of $T_H$-17 cell differentiation by RORγ ligands. Naïve $CD4^+CD62L^+$ T cells were incubated for five days in the presence of IL-6 and TGFβ and 0.01% DMSO. On day 5, a high level of intracellular cytokine expression is induced by combination of treatment with a phorbol ester, ionomycin, and brefeldin A, and $T_H$-17 and $T_H$1 cells identified by intracellular staining with antibodies to IL-17 and IFN-γ, respectively. The percentage of IL-17 positive cells, or $T_H$-17 cells, was calculated as a fraction of total live cells. OR-1050 decreases the proportion of $IL-17^+$ cells while OR-12872 increases the fraction of $IL-17^+$ cells. Each treatment was performed in duplicate (mean±SD, n=2)

For pharmacology studies, we added either agonist or antagonist to RORγ at the initiation of naïve CD4+ T cell cultures described above. We found that OR-1050 significantly inhibited $T_H$-17 cell differentiation in a dose-dependent manner while the potent agonist OR-12872 was stimulatory (see FIG. 7).

Figures 8C, 8D:
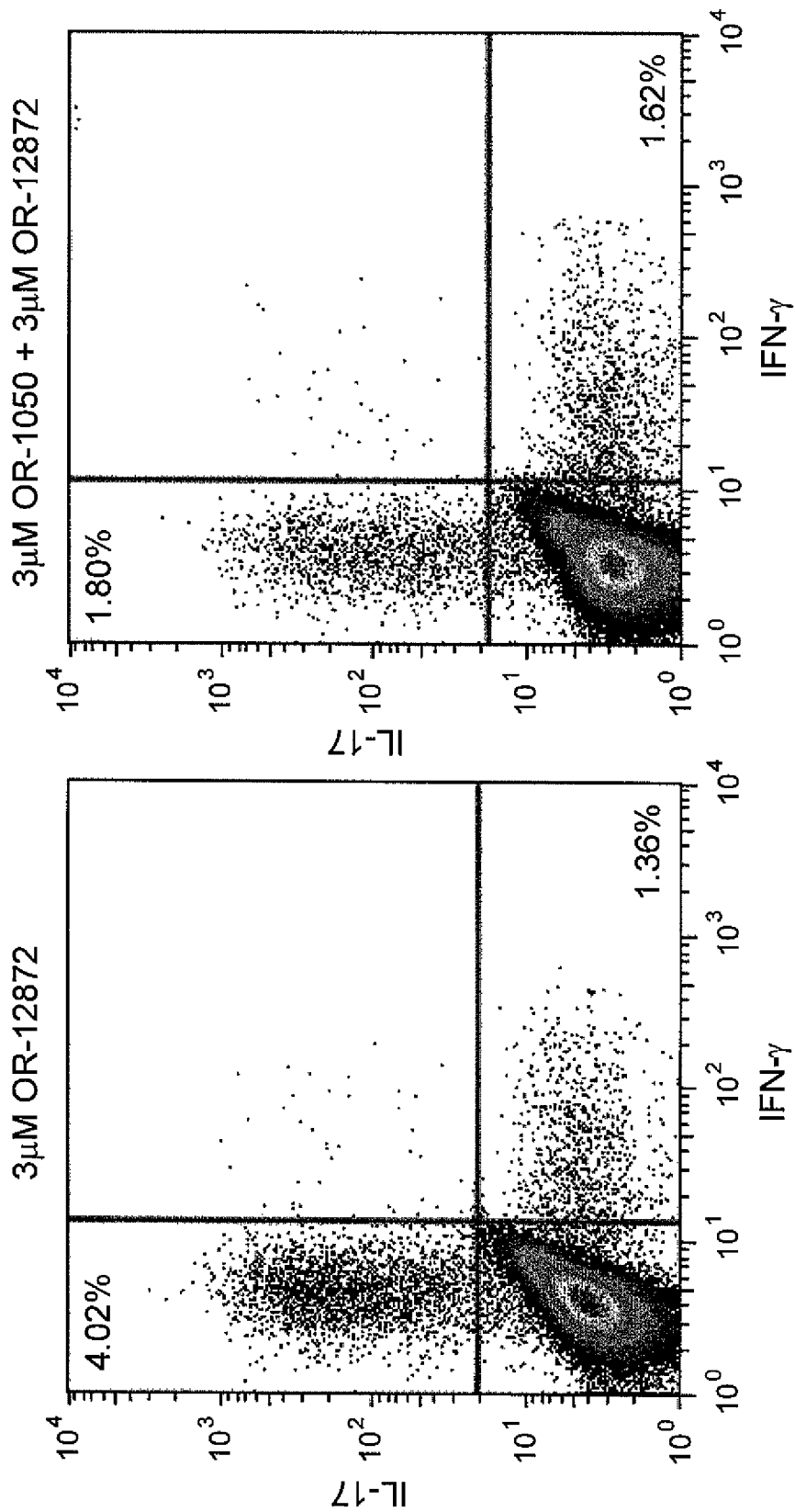

As expected from receptor pharmacology studies, OR-12872 was able to reverse the effect of OR-1050, consistent with the conclusion that both compounds act through the same target, i.e., RORγ (FIG. 8). In this experiment, the agonist OR-12872 alone elevated $T_H$-17 frequency by 60%, but in the presence of OR-1050 the agonist caused a 400% percent increase from the lower baseline produced by OR-1050, precisely the behavior expected if agonist and antagonist bind the same target. The figure represents individual observations, and the average of duplicate observations is presented in Table 9. Neither 3 μM OR-1050 nor 3 μM OR-12872 had an effect on the frequency of $T_H$1 cell differentiation in the presence of IL-12. The findings show that OR-1050 is unlikely to block $T_H$-17 cell formation through a non-specific cytotoxic effect for two reasons: it does not inhibit $T_H$1 differentiation and the blockage of $T_H$-17 differentiation is reversible by an RORγ agonist.

TABLE 9

Naïve CD4+ T cells were induced to differentiate with 4 ng/ml TGFβ and 20 ng/ml IL-6 ($T_H$-17 protocol) or 10 ng/ml IL-12 (Th-1 protocol). After addition of compound, the final DMSO concentration in the culture wells was 0.01%. Cytokine positive cells were determined as in the methods for this example. Duplicate cell cultures were counted and averaged.

|  | Cell Frequency (%) | | |
|---|---|---|---|
|  | $T_H$-17 Protocol | | Th-1 Protocol |
| Compound | IL-17+ | IFN-γ+ | IFN-γ+ |
| DMSO | 2.32% | 1.60% | 36.3% |
| 3 μM OR-1050 | 0.44% | 1.42% | 37.4% |
| 3 μM OR-12872 | 3.91% | 1.37% | 41.4% |
| OR-1050 + OR-12872 | 1.79% | 1.47% | 36.6% |

To provide additional confirmation that $T_H$-17 cell differentiation can be pharmacologically-regulated through inhibition of RORγ function, we tested the effects of the antagonist OR-885 and its reversal by OR-12872. FIG. 9 demonstrates that OR-885 blocks the differentiation of $T_H$-17 cells and that this effect is reversed by OR-12872. The results of this experiment are summarized in Table 10. It appears that there may be a small secondary effect of ligand on Th-1 cell levels. Overall, however, the RORγ ligands did not have a consistent effect on Th-1 cell frequency in these studies.

TABLE 10

Naïve CD4+ T cells were induced to differentiate with 4 ng/ml TGFβ and 20 ng/ml IL-6 ($T_H$-17 protocol) or 10 ng/ml IL-12 (Th-1 protocol). After addition of compound, the final DMSO concentration in the culture wells was 0.01%. Cytokine positive cells were determined as in the methods for this example. Duplicate cell cultures were counted.

|  | Cell Frequency (%) | | |
|---|---|---|---|
|  | $T_H$-17 Protocol | | Th-1 Protocol |
| Compound | IL-17+ | IFN-γ+ | IFN-γ+ |
| DMSO vehicle | 2.46% | 0.71% | 29.7% |
| 3 μM OR-885 | 0.52% | 1.45% | 34.2% |
| 1 μM OR-12872 | 3.96% | 0.65% | 30.8% |
| OR-885 + OR-12872 | 1.33% | 1.11% | 36.2% |

Finally, OR-13571 exerted a similar effect on $T_H$-17 differentiation as OR-885 and OR-1050. The effect of 3 μM OR-1050 was compared to that of 3 μM OR-13571 in Table 11.

TABLE 11

Studies were performed as in Table 9.

|  | Cell Frequency (%) Th-17 Differentiation | |
|---|---|---|
| Compound | IL-17+ | IFN-γ+ |
| DMSO vehicle | 3.81% | 1.03% |
| 3 μM OR-1050 | 1.47% | 1.09% |
| 3 μM OR-13571 | 1.42% | 0.93% |

The data show that OR-13571 also inhibits $T_H$-17 differentiation at a concentration of 3 μM. In summary, this example provides very strong pharmacological evidence that regulation of RORγ activity by small molecule ligands can control cell fate. Antagonists with 3 distinct structures were shown to have a similar effect on $T_H$-17 differentiation and two of these were reversed by a specific RORγ agonist, OR-12872. It is probable that the RORγ ligands will regulate $T_H$-17 function in other settings described in the literature, including by measurement of IL-17 release into surrounding medium and by culture of cells from lymph nodes of animals treated with antigen that provokes autoimmune disease (Murphy, Langrish et al. 2003; Langrish, Chen et al. 2005; Mangan, Harrington et al. 2006). This hypothesis is addressed in Example 6.

Figure 10:
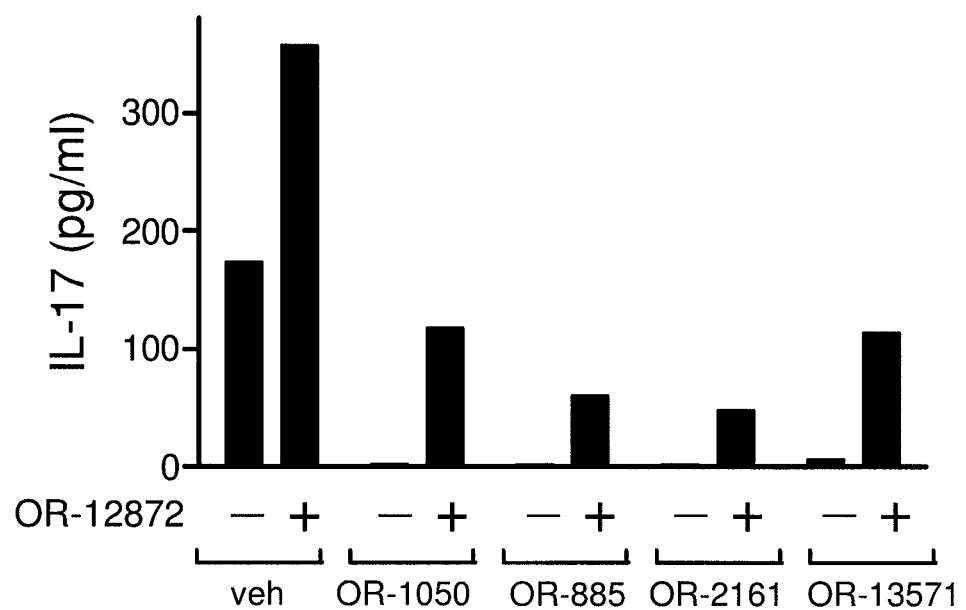
FIG. 10. IL-17 release into culture medium was measured four days after induction of $T_H$-17 differentiation in $CD4^+$ naïve murine T cells, following the methods of FIG. 7. Each antagonist (OR-885, OR-1050, OR-13571, and OR-2161) was incubated in the cultures at 3 μM, in the presence or absence of OR-12872, also at 3 μM. On day 4, culture supernatants were saved and IL-17 measured by ELISA.

We also investigated whether the concomitant release of IL-17 that is expected to take place with $T_H$-17 differentiation is pharmacologically regulated by RORγ ligands. RORγ antagonists at 3 μM were added as naïve CD4+ T cells were induced to differentiate into $T_H$-17 cells, in the presence or absence of OR-12872. In this study, all four RORγ antagonists tested block IL-17 release (FIG. 10). Significantly, the presence of OR-12872, the RORγ agonist, reverses the effect of each of the antagonists, indicating that the compounds are acting in an RORγ-specific manner. We hypothesize that the very marked reduction in IL-17 levels involved simultaneous inhibition of $T_H$-17 differentiation, as shown above, and suppression of IL-17 release.

Example 4

This example provides data suggesting that pharmacological repression of RORγ will not necessarily inhibit thymic function in vivo. The induction of liver triglycerides by OR-1050 in C57BL/6 mice following oral dosing was investigated. In addition, the effect of compound treatment in the same animals on the number and distribution of the major thymocyte populations was analyzed. The objective was to show evidence of bioavailability through elevation of liver triglycerides (through LXR), and at the same time to characterize the effect of OR-1050-mediated antagonism of RORγ on thymic function.

Methods

Following six days of twice-a-day dosing with corn oil vehicle or 50 mg/kg OR-1050 in corn oil, mice were sacrificed and the thymus and liver removed and weighed. A small piece of the liver (~200 mg) was weighed and extracted to determine triglyceride content. Glycerol was liberated from liver triglycerides by hydrolysis in base. The liver fragment was incubated overnight at 55° C. in 0.35 mls of ethanolic KOH (2 parts EtOH: 1 part 30% KOH) in a closed tube. A solution of 50% ethanol in water was added to bring the volume of each tube to 1.0 ml. The solution was cleared of debris by centrifugation, and the resulting supernatant increased to 1.2 ml with further addition of 50% ethanol. Aqueous 1 M $MgCl_2$ (215 μl) was added to 200 μl of the supernatant, and the mixture was cleared by centrifugation again after standing 10 min on ice. Glycerol levels were measured with the Sigma Free Glycerol Reagent (Sigma-Aldrich, St. Louis, Mo.) according to the manufacturer's instructions. The triglyceride concentration (in milligrams per gram of liver wet weight) was determined by assuming average molecular weight of 1000 daltons for each molecule of triglyceride.

In addition, the total number and the fraction of the major thymocyte subpopulations including $CD4^+CD8^+$ (DP), $CD4^+CD8^-$ ($SP4^+$) and $CD4^-CD8^+$ ($SP8^+$) were measured by cell surface staining followed by FACS analysis. The thymus was dissected, weighed, and gently pressed against a wire screen (200 mesh USA standard test sieve, Newark Wire Cloth Company) with plunger of a 5 ml plastic syringe. The volume of cells was adjusted to 8 mls. Debris from the thymus was allowed to settle, and a 200 μl aliquot of cells was incubated with fluorescent antibodies to CD4 and CD8 for 15 minutes at room temperature. The cells were fixed in 4% formalin in PBS and stored at 4° C. for 48 hours. Before analytical flow cytometry was carried out (FACS Calibur, Becton Dickinson), Caltag counting beads (from Invitrogen) were added to allow absolute quantitation of cell number. Thymus subpopulations were determined after gating for live cells. As a positive control for thymic involution, two animals were also treated once with 10 mg/kg dexamethasone two days before sacrifice. Dexamethasone reproducibly induces rapid apoptosis of DP thymocytes and reduction of thymic mass (Chmielewski, Drupt et al. 2000; Zubkova, Mostowski et al. 2005).

Results

Table 12 shows that liver triglyceride content (in mg of triglyceride/gram liver) is markedly elevated by OR-1050 as reported for other LXR agonists (Schultz, Tu et al. 2000; Beyer, Schmidt et al. 2004). In contrast, the number and fraction of major thymocyte subpopulations was not significantly affected. As expected, dexamethasone caused a virtually total depletion of DP thymocytes.

As shown above, OR-1050 is approximately 5-fold more potent in repression of RORγ transcription than it is in induction of LXR transcription. Thus it is likely that RORγ activity in mice treated as above was significantly repressed. This example demonstrates that pharmacological dosing of an RORγ antagonist does not necessarily cause thymic atrophy or loss of thymocytes following an intermediate period of dosing.

TABLE 12

Effects of OR-1050 on liver triglycerides and thymocyte distribution. C57BL/6 mice were treated by vehicle only (corn oil) or OR-1050 (100 mg/kg) for 7 days, or by dexamethasone (Dex, 12.5 mg/kg) once 2 days before necropsy. Corn oil and OR-1050 (50 mg/kg) were dosed twice per day by gavage. Liver triglycerides are reported as mg triglyceride/gram liver wet weight. One animal from the OR-1050 group had a very low frequency of DP thymocytes (<1% of control) and was excluded from this analysis.

|  | Group size | Liver triglycerides (mg/g) | Thymus weight (μg) | Total cells per spleen ($\times 10^{-6}$) | | | Frequency of DP (% of total cells) |
|---|---|---|---|---|---|---|---|
|  |  |  |  | DP | SP4 | SP8 |  |
| Vehicle | 6 | 34.7 ± 5.7 | 71.3 ± 12.0 | 58.7 ± 24.7 | 6.3 ± 1.7 | 2.0 ± 0.4 | 52.6 ± 8.4 |
| Dex | 2 | 35.3 ± 8.2 | 49.7 ± 1.2 | 1.0 ± 0.4 | 3.9 ± 0.1 | 1.2 ± 0.1 | 4.2 ± 2.9 |
| OR-1050 | 5 | 119.5 ± 18.8 | 76.1 ± 5.8 | 61.5 ± 10.0 | 8.1 ± 1.6 | 2.5 ± 0.5 | 56.7 ± 3.1 |

Example 5

This example provides a demonstration that an RORγ antagonist may inhibit the development of EAE in a mouse model.

Figure 11G:
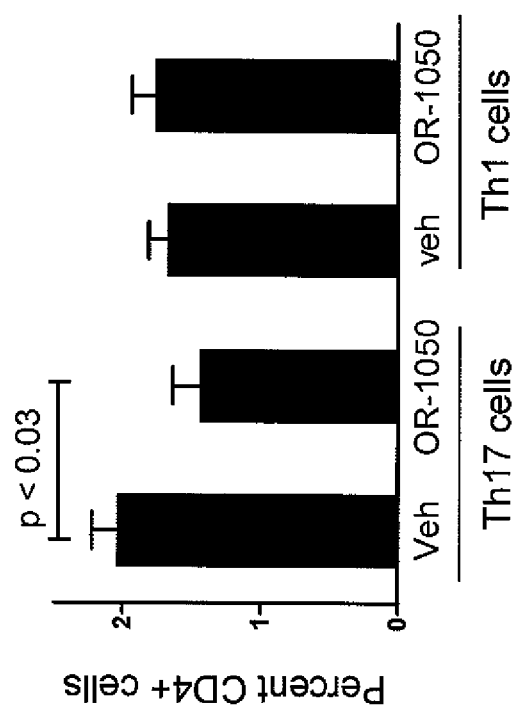
FIG. 11G shows the effect of OR-1050 on splenic $T_H$-17 cells in C57BL/6 mice (29% inhibition, p<0.05, n=8-10) with no change in $T_H$1 cells. C57BL/6 female mice were immunized with 150 μg $MOG_{33-55}$ on study day 0. Mice were treated with either OR-1050 at 100 mg/kg or with vehicle (HRC-6) by oral gavage for 9 days starting day 0, Splenocytes were collected at Day 9 and stained for $T_H$-17 ($CD4^+CD8^-IL17^+$) and $T_H$1 ($CD4^+CD8^-IFN\gamma^+$) cells. Statistics were performed by Student's t-test.

Methods 8-10 week old, female C57BL/6 mice or SJL/J mice were purchased from Harlan laboratories (Harlan, Indianapolis, Ind.) and housed in a specific pathogen free (SPF) animal facility for one week before the start of the studies. Mice were immunized with peptide antigens intradermally at the dorsal flanks on day 0. Peptide antigens are either 150 μg $MOG_{35-55}$ (MEVGWYRSPFSRVVHLYRNGK (SEQ ID NO: 19), AnaSpec, San Jose, Calif.) per C57BL/6 mouse or 75 μg $PLP_{139-151}$ (HSLGKWLGHPDKF (SEQ ID NO: 20), Bio-Synthesis, Lewisville, Tex.) per SJL/J mouse. Peptides were dissolved in PBS and emulsified with an equal volume of Complete Freund's Adjuvant (CFA) containing 4 mg/ml of H37RA *M. tuberculosis* (Chondrex, Redmond, Wash.). To ensure induction of reliable EAE, 200 ng of pertussis toxin (List Biologicals, Campbell, Calif.) was given by via intravenous injection (i.v.) at day 0 and 2 (Cua, Sherlock et al. 2003; Zhang, Gran et al. 2003). Animals were treated with drug beginning one day before peptide injection. Animals were randomized into groups for treatment by weight, so that the average weight of each group was similar. The groups were not segregated by cage. Instead, members of all groups were represented in every cage in order to minimize environmental effects on the outcome of the study. In the C57BL/6 study, OR-1050 was suspended in corn oil by sonication at 6 mg/mL or 20 mg/mL and animals were dosed twice daily by gavage with 2.5 mls/kg body weight of corn oil for each dose. In one SJL/J study (FIG. 11D & E), OR-1050 was dissolved in dimethylformamide at 200 mg/ml, further diluted into three parts of HRC-6, loaded into an osmotic pump (Alzet 2002) and implanted in the interscapular region under anesthesia 2-3 days after peptide immunization. The estimated daily does was 30 mg/kg in this study. In another SJL/J study (see FIG. 11F), mice were treated once daily by gavage with 100 mg/kg OR-1050 solubilized in the synthetic vehicle HRC-6.

Clinical symptoms are scored by a visual inspection of behavior, along the following scale (Papenfuss, Rogers et al. 2004): 1) Limp tail or waddling gait; 2) waddling gait with tail limpness; 3) partial hind limb paralysis; 4) complete hind limb paralysis; 5) moribund state, leading to death by EAE. At severity level 4 or 5 the animals were sacrificed to prevent further suffering. Animals were weighed daily during the treatment period as a secondary measure of the disease course. As a comparative measure for drug treatment, the median day of onset was compared between groups. Statistical analysis was by the Kruskal-Wallis test, a non-parametric test for comparison of multiple groups. On study day 27, remaining animals were euthanized, and brain and spinal cord fixed, embedded in paraffin, and H&E sections analyzed for inflammatory infiltration. For the studies of inflammation, several sections of spinal cord (7 to 8) were characterized by an experienced veterinary pathologist in a blinded fashion. Inflammation in each section was evaluated visually using a semi-quantitative scale based on the overall severity of the sample (e.g., Severity: 0, not present; 1, slight; 2, mild, 3, moderate; 4, severe).

Results

Figure 12A:
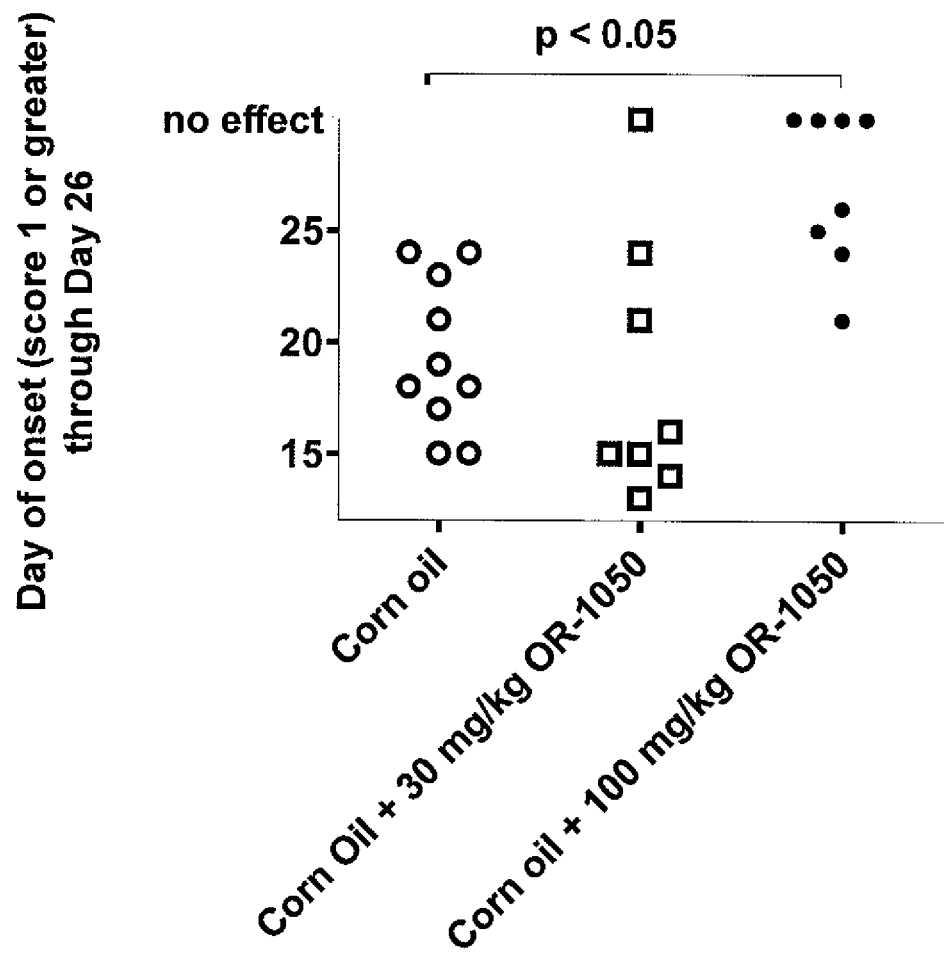
FIG. 12A. OR-1050 inhibits the onset of paralysis in a murine model of EAE. This is a separate statistical analysis of data presented in FIG. 11A. C57BL/6 mice were immunized with $MOG_{35-55}$, an immunogenic peptide derived from myelin oligodendrocyte glycoprotein, to trigger symptoms of EAE. Mice were treated with corn oil vehicle or OR-1050 (15 mg/kg or 50 mg/kg) twice per day by gavage starting one day before injection of $MOG_{35-55}$ and continuing for 25 days after injection. The day on which a visual, clinical score first reached 1 or greater was recorded for each mouse, and observations were carried out until day 26. By a rank order non-parametric test for multiple groups (Kruskal-Wallis, with Dunn's Multiple Comparison Test for significance), the onset of EAE (determined as a severity score of 1 or greater) in mice treated with 100 mg/kg OR-1050 per day is significantly ($p<0.05$) delayed compared to the vehicle control. A similar finding was obtained by analysis of day of onset determined by severity score of 2 or greater.

C57BL/6 mice were treated with OR-1050 by oral gavage twice a day for a total dose of 30 mg/kg or 100 mg/kg for 25 days. Mice were injected with a peptide that induces autoimmune disease in this mouse strain one day after the start of dosing. The progress of the disease in the vehicle and high dose groups is illustrated in FIG. 11A and FIG. 11B, where exposure to OR-1050 both inhibits progress of the disease and weight loss doe to the onset of symptoms. FIG. 11C shows that inflammatory infiltration in the spinal cord was reduced by treatment with OR-1050 in these animals. The onset of disease in the three groups as a function of number of days since peptide immunization is presented in FIG. 12. The median day of onset of symptoms (clinical score 1 or greater) was day 18 for the corn oil vehicle control, day 16 for the 30 mg/kg group, and day 26 for the 100 mg/kg treated group (FIG. 12A). The median day of onset for untreated animals was day 15 (not shown). The difference in day of onset between the vehicle and the 100 mg/kg treated animals was statistically significant (p<0.05). This example shows that an RORγ antagonist is able to delay the onset of EAE. The surviving animals at day 27 showed a difference in the severity of inflammation in spinal cord between vehicle and high dose treated animals. The statistical significance was based on a rank order test (p<0.07, Mann-Whitney).

In a second EAE mouse study, SJL/J mice were immunized with PLP139-151 and OR-1050 was dosed by osmotic pump to achieve more stable compound delivery starting at day 4. OR-1050 also reduced paralytic severity (FIG. 11D) and onset (FIG. 11E). In each of these studies, there was a significant difference in severity or weight on several days, as indicated in the graphs (FIG. 8A, B&D). Using a more rigorous statistical analysis, we calculated the area under the severity curve for each of the mice in FIG. 11D, and compared the mean values±sem for vehicle (14.5±1.6) and treated (5.3±2.7) groups. The differences were significant (p<0.01) based on the Mann-Whitney rank order test (GraphPad Prism, San Diego). Furthermore, as shown in FIG. 11E, the day of onset was significantly delayed in the treated SJL/J mice.

Since OR-1050 inhibits $T_H$-17 cells in ex vivo culture, we also investigated whether $T_H$-17 cell frequency was affected in OR-1050-treated animals. SJL/J female mice (n=9/group) were treated with 100 mg/kg OR-1050 in HRC-6 beginning two days before immunization with PLP (as described above) and continuing until 8 days after immunization. Animals were sacrificed on day 9, and $T_H$-17 cells analyzed from pooled axillary, brachial, and inguinal lymph nodes from each animal. We found a 35% reduction in $T_H$-17 frequency in lymph nodes of SJL/J mice (FIG. 11F) as a fraction of the total $CD4^+$ cell population. The change in $T_H$-17 frequency with OR-1050 treatment was statistically significant.

In a second study on C57BL/6 mice (FIG. 11G), we observed a similar effect on splenic $T_H$-17 cells in C57BL/6 mice (29% inhibition, p<0.05, n=8-10) with no change in $T_H1$ cells. C57BL/6 female mice were immunized with 150 µg $MOG_{33-55}$ on study day 0. Mice were treated with either OR-1050 at 100 mg/kg or with vehicle (HRC-6) by oral gavage for 9 days starting day O, Splenocytes were collected at Day 9 and stained for $T_H$-17 ($CD4^+CD8^-IL17^+$) and $T_H1$ ($CD4^+CD8^-IFN\gamma^+$) cells. Statistics were performed by Student's t-test. Collectively, the data suggest that OR-1050 inhibits the expansion of $T_H$-17 cells in response to peptide antigen.

Figure 12B:
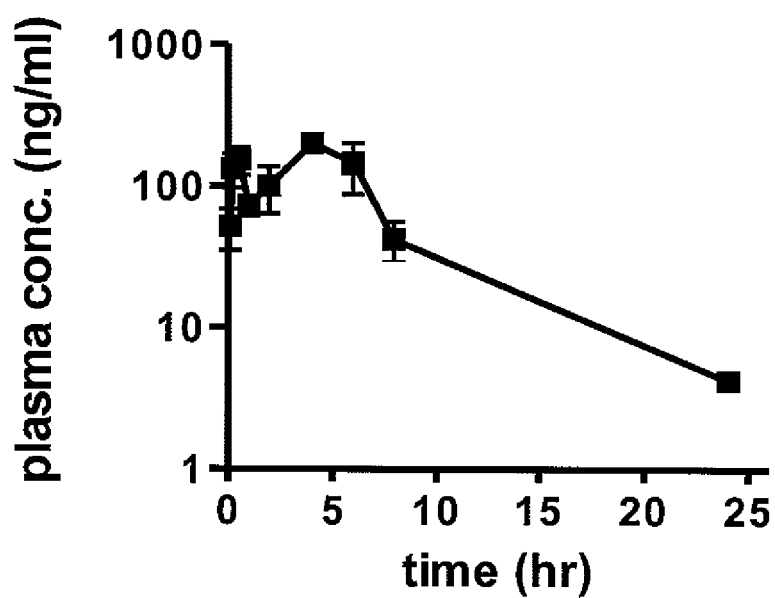
FIG. 12B. Bioavailability of OR-1050. OR-1050 was dosed in CD-1 mice at 5 mg/ml in HRC-6, a proprietary formulation that is commercially available from Pharmatek (San Diego, Calif.). Blood samples from triplicate animals were tested for levels of OR-1050 at multiple time points.

In a separate study related to these findings, we demonstrated that OR-1050 is orally bioavailable (FIG. 12B). Pharmacokinetics of OR-1050 in CD-1 mice was analyzed at independent bioanalytical laboratory. Male CD-1 mice were treated via oral gavage with OR-1050 at 5 mg/kg in HRC-6. Blood was collected via retro-orbital puncture in tubes containing sodium heparin anticoagulant at 0, 5, 15, and 30 min, and at 1, 2, 4, 6, 8 and 24 hr after oral administration. The concentration of OR-1050 in plasma was determined using an HPLC/MS/MS method. The peak concentration of OR-1050 (~100 ng/ml) suggests that a higher dosage (50 mg/kg) will give blood levels, 1 µg/ml or ~2 µM, that is higher than the $EC_{50}$ for OR-1050 in transcriptional assays in in vivo pharmacological studies.

Example 6

That RORγ antagonists inhibit the differentiation of $T_H$-17 is consistent with the phenotype of the RORγ$^{-/-}$ mouse, which lacks $T_H$-17 cells and where naive $CD4^+$ T cells resist differentiate to $T_H$-17 in the presence of IL-6 and TGFβ (Ivanov, McKenzie et al. 2006). The question of whether the reactivation of memory $T_H$-17 cells can be blocked by RORγ ligands is not addressed by the RORγ$^{-/-}$ mouse phenotype, since memory $T_H$-17 cells are unable to differentiate from naïve $CD4^+$ T cells. To address the issue, we cultured lymph node cells from mice previously immunized with the myelin-derived peptides $PLP_{139-151}$, $MOG_{35-55}$, or complete Freund's adjuvant (CFA) alone. Memory T cells are known to proliferate in response to cognate peptide in these cultures, and our controls showed that stimulation of $T_H$-17 proliferation and IL-17 release were dependent on prior immunization with peptide, consistent with a memory T cell response (FIG. 13A). Thus, LN cultures from CFA-immunized mice were insensitive to PLP in 3 day culture, whereas LN cultures from mice immunized with PLP (emulsified in CFA) showed a ~10-fold increase in IL-17 release and a concomitant two-fold elevation in the frequency of $T_H$-17 cells in response to peptide (not shown). These data show that IL-17 induction is closely linked to the peptide-dependent increase in $T_H$-17 cells and therefore provides a convenient method of characterizing compound effects on Th-17 cells. Furthermore, OR-885 inhibited the PLP-stimulated release of IL-17. The correlation between Th-17 cell number and IL-17 release in the presence of agonist and antagonist was further confirmed (FIGS. 13B and 13C), and the antagonist OR-885 was shown to block both the induction of $T_H$-17 cells (as a percentage of total live cells) and IL-17 release.

Figure 14:
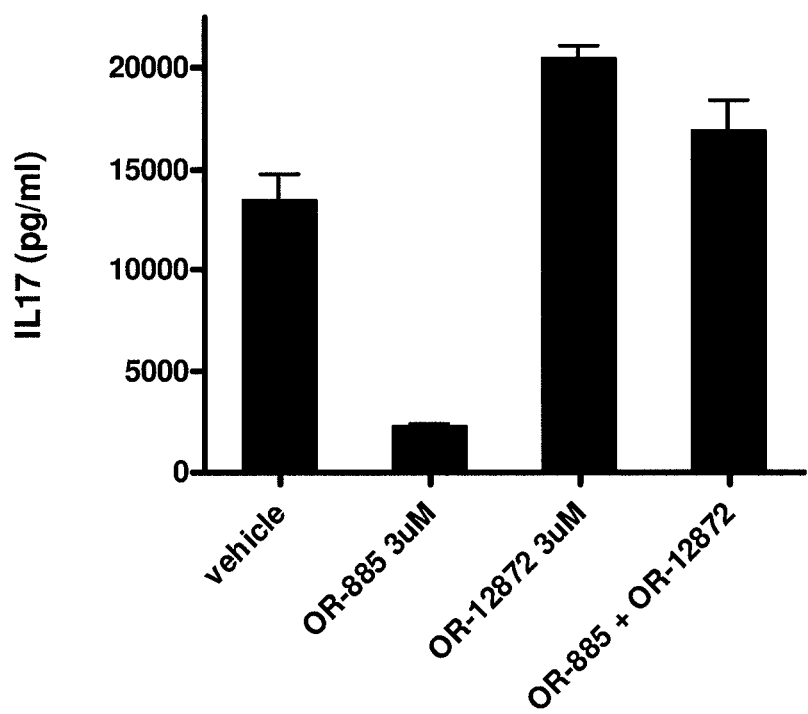
FIG. 14. Inhibition of IL-17 release in mouse lymph node cultures by the RORγ antagonist OR-885 can be reversed by the RORγ agonist OR-12872. The lymph node cells were culture in the presence of 10 ng/mL IL-23 and 40 μg/mL PLP for three days under identical conditions to FIG. 13 and IL-17 in the culture supernatant was measured by ELISA.

Overall, cultured lymph node cells that are stimulated with IL-23 and peptide antigens provide a model system to examine IL-17 production ex vivo (FIG. 13D). We analyzed a variety of RORγ ligands for their ability to regulate IL-17 (FIG. 13E). Four different classes of RORγ antagonists tested all inhibit IL-17 release, while the agonist is able to activate IL-17. A dose-response assay suggested that the antagonist OR-885 inhibits IL-17 production with an $EC_{50}$ value of approximately 0.2 μM (FIG. 13F). Each point is the average of duplicate measurements of IL-17 release in a single well. This potency is consistent with that measured in the CHO cell transcription assay. To further confirm that the activity of compounds was RORγ-dependent in this system, we showed that the agonist OR-12872 reverses the suppressive effects of OR-885 on IL-17 release in lymph node cultures (FIG. 14).

Figure 15B:
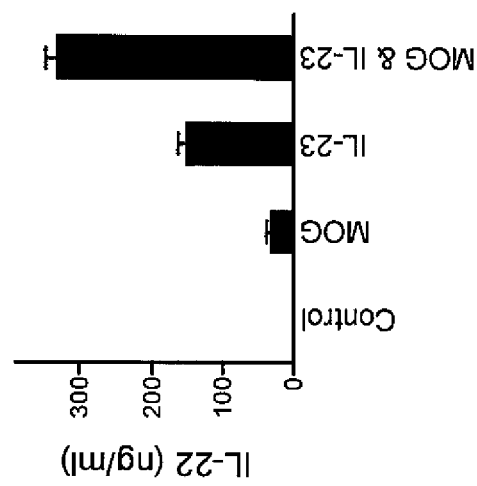
FIGS. 15A-B. IL-22 release in lymph node cultures is regulated by RORγ ligands. Lymph node cells from MOG-immunized C57BL/6 mice were cultured for 3 days with 30 μg/ml MOG, 10 mg/ml IL-23 (FIG. 15A) and 3 μM compounds (FIG. 15B). Culture media were analyzed by IL-22 ELISA.
Figure 15A:
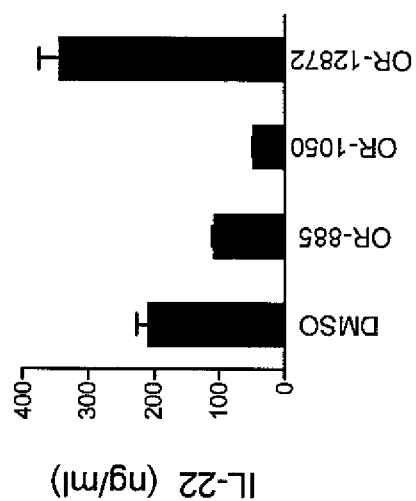

The proinflammatory cytokine IL-22 is also expressed in Th-17 cells. We characterized IL-22 release from lymph node cell cultures and found that like IL-17, IL-22 release is induced by both peptide antigen and IL-23, and that the effect of both was more than additive. In addition, IL-22 seems to have 30-50 fold higher levels than IL-17. IL-22 production is also inhibited by the RORγ antagonists OR-885 and OR-1050 and enhanced by the agonist OR-12872 at a concentration of 3 μM each in LN cultures, similar to findings with the IL-17 assays. This is illustrated in FIG. 15.

Figure 16A:
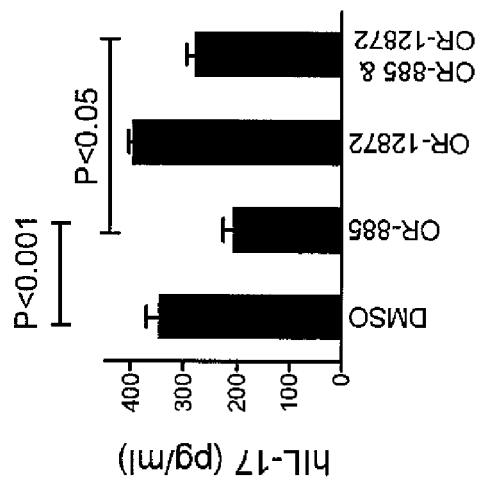
FIGS. 16A-C. Human IL-17 release from activated human T cells is inhibited by RORγ antagonist and is partially reversible in the presence of OR-12872, an RORγ agonist.
Figure 16B:
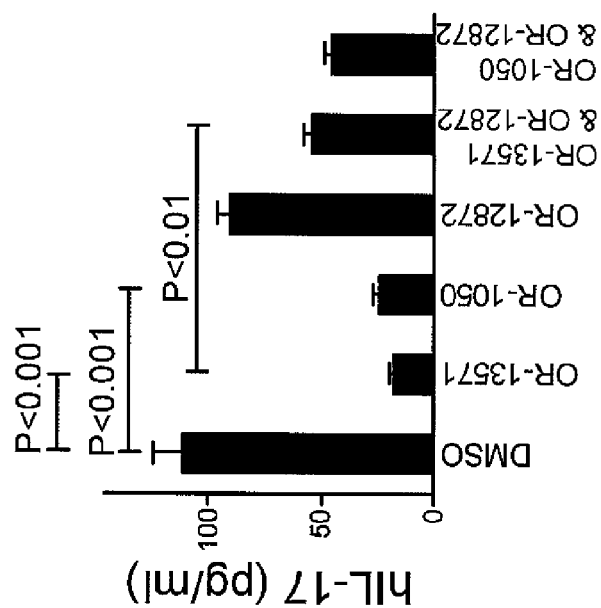

Regulation of Human IL-17 Release in Cultured PBMCs. We also investigated whether human IL-17 is subject to regulation by RORγ ligands. It has proven difficult to differentiate Th-17 cells from naïve human T cells under the same conditions as mouse (Zheng, Danilenko et al. 2007), although there are now several very recent reports that this can be done (Acosta-Rodriguez, Napolitani et al. 2007; Annunziato, Cosmi et al. 2007; Wilson, Boniface et al. 2007). Since mitogenic stimuli such as ConA or PMA will stimulate IL-17 expression in memory T cells in human PBMC (Yao, Painter et al. 1995; Shin, Benbernou et al. 1999), we used this protocol for an initial investigation of IL-17 regulation by RORγ ligands. Frozen human peripheral blood mononuclear cells (PBMCs from Stem Cell Technologies, Vancouver) were thawed and cultured for 3 days with 1 μg/ml Con A and 3 μM compounds in lymphocyte culture medium (RPMI 1640 media containing 10% heat-inactivated FCS, 100 IU penicillin, 100 μg/ml streptomycin, 1×non-essential amino acids, 1 mM pyruvate, 2 mM glutamine, and 50 μM β-mercaptoethanol). Culture media were analyzed by hIL-17 ELISA (mean±sem, n=4; ANOVA with Bonferroni post test). In FIG. 16A, the effects of 3 μM OR-885 and 3 μM OR-12872 on IL-17 release from PBMCs were compared. The effect of OR-885 was partially reversible by OR-12872. FIG. 16B shows that stimulated IL-17 release into culture medium by ConA is inhibited by OR-13571 and OR-1050. The possibility that inhibition mediated by these two compounds is due to cytotoxicity was addressed by co-treatment with the RORγ agonist OR-12872. OR-12872 alone does not significantly alter IL-17 release but it does partly reverse the effects of OR-1050 and OR-13571, suggesting that both compounds act specifically through RORγ.

Figure 16C:
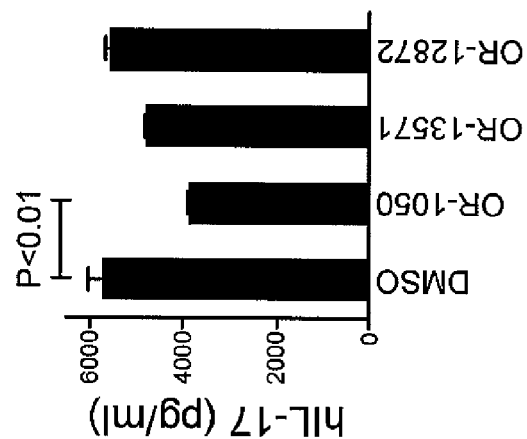

In a separate study, T-cell blasts were generated from human PBMC according to methods previously described (Hoeve, Savage et al. 2006). Frozen T-cell blasts were thawed and cultured for 18 hours in a 24-well plate with 1×10⁶ cells per well in 700 μL of lymphocyte culture medium. Phorbol 12,13-dibutyrate (500 ng/ml), ionomycin (500 ng/ml) and compounds (3 μM) were added at the beginning of the culture. Culture media were collected and analyzed for hIL-17 level by ELISA. The results of treatment with OR-1050 and OR-13571 are shown in FIG. 16C.

Example 7

Methods. 8 to 10-week old male DBA/1 (DBA/1OlaHsd, Harlan Laboratories) mice are housed in a specific pathogen free (SPF) animal facility. Arthritis is induced by two injections of collagen subcutaneously in the base of the tail. The initial injection (on day 0) uses bovine type II collagen (2 mg/ml from Chondrex, Redmond, Wash.) emulsified in equal volume of CFA containing 4 mg/ml of *M. tuberculosis* (Chondrex). The CII booster injection on Day 29 is emulsified in incomplete Freund's adjuvant (IFA). Each animal receives 0.1 ml of emulsion by subcutaneous/intradermal injection in the tail 2 to 3 cm from the body of the mouse. The booster injection site is in the vicinity of but different from the initial injection site and closer to the body of the animal. OR-1050 was formulated in HRC-6 as above. On weekdays, the animals received two doses (a.m. and p.m.) of HRC-6 or 50 mg/kg OR-1050 p.o. (2.5 mls/kg). On weekends, a single dose of 100 mg/kg was administered (5 mls/kg).

Figure 17B:
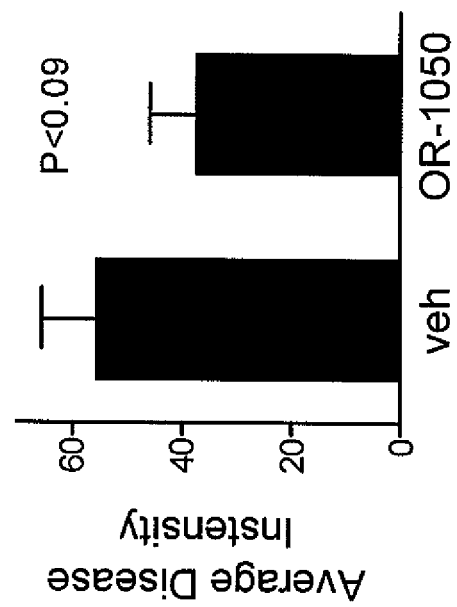
FIGS. 17A-B. RORγ antagonist regulation of CIA in DBA/1 mice. Mice were immunized with bovine type II collagen (CII) at days 0 and 29.

The mice were observed daily for clinical symptoms of CIA based on the following qualitative scale. Each paw was examined individually and scored. Grade 0, normal; grade 1, mild but definite redness and swelling of the ankle or wrist, or apparent redness and swelling limited to individual digits, regardless of the number of affected digits; grade 2, moderate redness and swelling of ankle or wrist; grade 3, severe redness and swelling of the entire paw including digits; grade 4, maximally inflamed limb with involvement of multiple joints. To estimate cumulative disease severity for each animal, an area under the curve score was calculated for each animal by totaling the sum of the daily hind paw measurements betweens days 24 and 48. Because of the difficult of adequately distinguishing multiple gradations of change in the front paws, scoring of the hind paw only was used in FIG. 17.

Figure 17A:
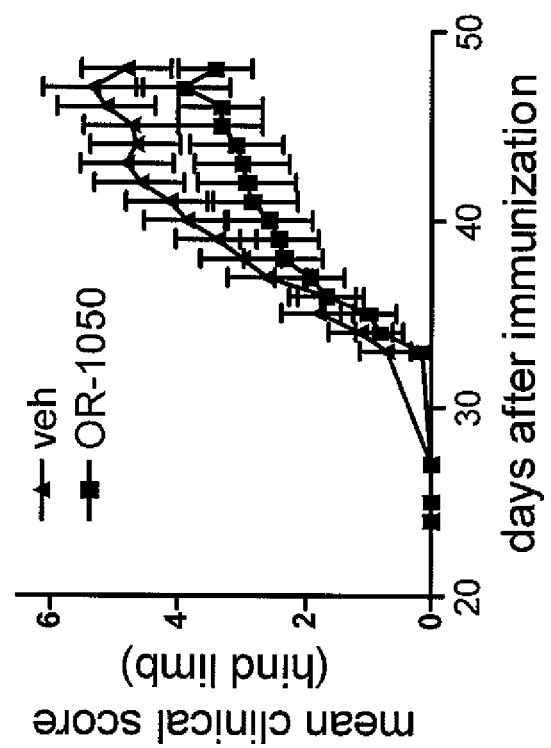

Results. We investigated the effect of the RORγ antagonist OR-1050 on the course of collagen-induced arthritis in mouse, where $T_H$-17 cells are clearly involved (Courtenay, Dallman et al. 1980; Sato, Suematsu et al. 2006). Animals were treated with OR-1050 (p.o.) starting three days before immunization with collagen type II. The disease phenotype is first clearly visible about one week after the second injection of CII (at day 29), and the disease course is partly suppressed in the OR-1050-treated animals when compared to vehicle controls (FIG. 17A). Based on the difference in overall disease severity determined in the hind limbs of the animals (FIG. 17B), the response shows a trend ($p<0.09$) towards a statistically significant effect.

Example 8

The present invention provides for the discovery of novel small molecule antagonists to RORγ that are useful in the treatment of autoimmune disease and other conditions involving the inhibition of $T_H$-17 cell activity. The steps required to identify a clinical candidate can be outlined briefly. (1) Novel compounds derived from diverse screening libraries, or by directed chemical synthesis from known hits, are tested for activity in transcriptional and biochemical assays for RORγ. (2) Hits from this primary screening are then characterized for specificity against a panel of other nuclear receptors as described above. (3) Candidate lead compounds for more extensive animal studies are selected from these hits on the basis of potency and selectivity. A candidate lead is expected to inhibit murine $T_H$-17 cell formation in culture. The candidate lead molecules are tested for other desirable properties such as bioavailability and metabolic stability that enable therapeutic use of the compound in animal models of disease. (4) One or more lead RORγ antagonists are tested in animal models of EAE, CIA and IBD which are known to respond to other agents that inhibit $T_H$-17 function. If active in one or more of these models, the compounds are tested for general immunotoxicity, effects on thymic function and overall immune response, and on general aspects of toxicity such as liver triglyceride content and serum lipids known to be affected by ligands to several nuclear receptors. (5) Such leads are further examined for properties that would prevent use in humans. These include potential for drug-drug interactions and general toxicity in rodents and at least one other higher species. If problems in the areas of drug-drug interactions or toxicity are identified, compounds may be further modified by synthetic methods, rescreened, and reevaluated to reduce these side effects. Other features that may be optimized at this stage are bioavailability, chemical stability, and ease of manufacture. (6) One or more candidate clinical compounds are selected for safety studies leading to Investigative New Drug status granted by the FDA. This step enables human clinical trials that will provide evidence for safety and therapeutic utility. The execution of steps two and beyond is well understood by practitioners of the art of drug discovery. The validation of RORγ antagonist effects in $T_H$-17 cells provides the scientific rationale for undertaking drug development.

As another example, the invention envisages modification of hit or lead molecules to generate lead candidates. Examples of hits useful for further medicinal synthetic work are OR-1050 or OR-133171 described above. Analogs of these affect potency at RORγ in a logical manner. Significantly, a representative member of the OR-133171 series was shown to have no measurable transcriptional activity at LXRα. More potent compounds may be modified by parallel synthetic modification of the core scaffolds of these two compounds in pharmacological assays. These assays may identify compounds that increase potency. Other assays for metabolic stability and bioavailability may be introduced in order to identify a useful lead compound. The invention also provides for the discovery of alternative compound series to those indicated above, in case these fail to provide molecules with characteristics suitable for commercial development, by screening additional small molecule drug-like compound libraries.

A drug from the RORγ antagonist class will ideally have good oral bioavailability and a half-life of four hours or more, enabling once or twice-daily administration. Nuclear receptor ligands have commonly given rise to orally bioavailable drugs; OR-1050 is an example of an orally-bioavailable RORγ antagonist characterized in these studies. The advantages of an orally bioavailable drug are: (i) direct oral administration is feasible; (ii) unlike injectable biologics, which may have an extremely long half life, a small molecule drug with reasonable half-life can be withdrawn if necessary to limit side effects and (iii) small molecule drugs are readily manufactured. Such compounds may also be selected for clinical development by potency in animal models of EAE, CIA and IBD and by parallel in vivo studies of compound safety. Examples of useful models for investigation of RORγ antagonist effects on EAE, in addition to the C57BL/6 mouse immunized with the $MOG_{35-55}$ peptide, are female SJL/J mice induced with the myelin proteolipid peptide ($PLP_{139-151}$) (Papenfuss, Rogers et al. 2004) and the Lewis rat (Bolton, O'Neill et al. 1997). EAE may also be induced by adoptive transfer of cultured, antigen-specific $T_H$-17 cells from previously immunized mice (Langrish, Chen et al. 2005). CIA is induced by injection of type 2 collagen (Courtenay, Dallman et al. 1980) and this model is recognized to be IL-23 and $T_H$-17 cell dependent (Murphy, Langrish et al. 2003; Lubberts, Koenders et al. 2004). Mouse models of IBD are now recognized to have a significant involvement of $T_H$-17 cells (Yen, Cheung et al. 2006; Zhang, Zheng et al. 2006; Elson, Cong et al. 2007). Certain genetic models such as the $IL-10^{-/-}$ mouse (Yen, Cheung et al. 2006) have physiological relevance for understanding disease and have been shown to require IL-23 for disease induction, but the disease course itself is prolonged and highly variable in these animals, rendering them unfavorable for pharmacological studies of reasonable duration. On the other hand, transfer of T cell populations with a reduced component of T regulatory cells to immunodeficient mice will cause disease within about 10 weeks (Powrie and Uhlig 2004), a time frame suitable for pharmacological testing. Disease causation in the T cell transfer model is also dependent on IL-23 (Yen, Cheung et al. 2006). Older mouse IBD models that induce damage to the intestinal lining, such as by treatment with dextran sodium sulfate (DSS) in drinking water (Spahn, Herbst et al. 2002), are acceptable disease models and may also include a significant contribution by $T_H$-17 cells.

While the invention has been described with reference to specific examples, this description is not meant to limit the kind of small molecule drug that may be used as part of practicing this invention.

LITERATURE CITED

Acosta-Rodriguez, E. V., G. Napolitani, et al. (2007). "Interleukins 1beta and 6 but not transforming growth factor-beta are essential for the differentiation of interleukin 17-producing human T helper cells." *Nat. Immunol.*

Acosta-Rodriguez, E. V., L. Rivino, et al. (2007). "Surface phenotype and antigenic specificity of human interleukin 17-producing T helper memory cells." *Nat Immunol* 8: 639.

Aggarwal, S., N. Ghilardi, et al. (2003). "Interleukin-23 promotes a distinct CD4 T cell activation state characterized by the production of Interleukin-17." *J. Biol. Chem.* 278(3): 1910-1914.

Annunziato, F., L. Cosmi, et al. (2007). "Phenotypic and functional features of human Th17 cells." *J Exp Med* 204(8): 1849-61.

Batten, M., J. Li, et al. (2006). "Interleukin 27 limits autoimmune encephalomyelitis by suppressing the development of interleukin 17-producing T cells." *Nat Immunol* 7(9): 929-936.

Becher, B., B. G. Durell, et al. (2002). "Experimental autoimmune encephalitis and inflammation in the absence of interleukin-12." *J Clin Invest* 110(4): 493-7.

Becker-Andre, M., I. Wiesenberg, et al. (1994). "Pineal gland hormone melatonin binds and activates an orphan of the nuclear receptor superfamily." *J Biol Chem* 269(46): 28531-4.

Becker-Andre, M., I. Wiesenberg, et al. (1997). "Additions and Corrections to Pineal gland hormone melatonin binds and activates an orphan of the nuclear receptor superfamily." *J. Biol. Chem.* 272(26): 16707.

Bettelli, E., Y. Carrier, et al. (2006). "Reciprocal developmental pathways for the generation of pathogenic effector TH17 and regulatory T cells." *Nature* 441(7090): 235-8.

Beyer, T. P., R. J. Schmidt, et al. (2004). "Coadministration of a liver X receptor agonist and a peroxisome proliferator activator receptor-alpha agonist in Mice: effects of nuclear receptor interplay on high-density lipoprotein and triglyceride metabolism in vivo." *J Pharmacol Exp Ther* 309(3): 861-8.

Bolton, C., J. K. O'Neill, et al. (1997). "Regulation of chronic relapsing experimental allergic encephalomyelitis by endogenous and exogenous glucocorticoids." *Int Arch Allergy Immunol* 114(1): 74-80.

Bowman, E. P., A. A. Chackerian, et al. (2006). "Rationale and safety of anti-interleukin-23 and anti-interleukin-17A therapy." *Curr. Opin. Infect. Dis.* 19: 245-252.

Bramlett, K. S., S. Yao, et al. (2000). "Correlation of farnesoid X receptor coactivator recruitment and cholesterol 7alpha-hydroxylase gene repression by bile acids." *Mol Genet Metab* 71(4): 609-15.

Chintalacharuvu, S. R., G. E. Sandusky, et al. (2007). "Liver X receptor is a therapeutic target in collagen-induced arthritis." *Arthritis Rheum* 56(4): 1365-7.

Chmielewski, V., F. Drupt, et al. (2000). "Dexamethasone-induced apoptosis of mouse thymocytes: prevention by native 7alpha-hydroxysteroids." *Immunol Cell Biol* 78(3): 238-46.

Courtenay, J. S., M. J. Dallman, et al. (1980). "Immunisation against heterologous type II collagen induces arthritis in mice." *Nature* 283(5748): 666-8.

Coward, P., D. Lee, et al. (2001). "4-Hydroxytamoxifen binds to and deactivates the estrogen-related receptor gamma." *Proc Natl Acad Sci USA* 98(15): 8880-8884.

Cua, D. J., J. Sherlock, et al. (2003). "Interleukin-23 rather than interleukin-12 is the critical cytokine for autoimmune inflammation of the brain." *Nature* 421(6924): 744-8.

Darimont, B. D., R. L. Wagner, et al. (1998). "Structure and specificity of nuclear receptor-coactivator interactions." *Genes & Dev.* 12: 3343-3356.

Dhib-Jalbut, S. (2002). "Mechanisms of action of interferons and glatiramer acetate in multiple sclerosis." *Neurology* 58(8 Suppl 4): S3-9.

Drake, K. A., J. H. Zhang, et al. (2002). "Development of a homogeneous, fluorescence resonance energy transfer-based in vitro recruitment assay for peroxisome proliferator-activated receptor delta via selection of active LXXLL coactivator peptides." *Anal Biochem* 304(1): 63-9.

Eberl, G. and D. R. Littman (2004). "Thymic origin of intestinal alphabeta T Cells revealed by fate mapping of RORgammat+ cells." *Science* 305(5681): 248-51.

Eberl, G., S. Marmon, et al. (2004). "An essential function for the nuclear receptor RORgamma(t) in the generation of fetal lymphoid tissue inducer cells." *Nat Immunol* 5(1): 64-73.

Elson, C. O., Y. Cong, et al. (2007). "Monoclonal anti-interleukin 23 reverses active colitis in a T cell-mediated model in mice." *Gastroenterology* 132(7): 2359-70.

Fu, M., T. Sun, et al. (2005). "A Nuclear Receptor Atlas: 3T3-L1 Adipogenesis." *Mol Endocrinol: me.* 2004-0539.

Gold, R., C. Linington, et al. (2006). "Understanding pathogenesis and therapy of multiple sclerosis via animal models: 70 years of merits and culprits in experimental autoimmune encephalomyelitis research." *Brain* 129(8): 1953-1971.

Gran, B., G. X. Zhang, et al. (2002). "IL-12p35-deficient mice are susceptible to experimental autoimmune encephalomyelitis: evidence for redundancy in the IL-12 system in the induction of central nervous system autoimmune demyelination." *J Immunol* 169(12): 7104-10.

Greiner, E. F., J. Kirfel, et al. (1996). "Functional analysis of retinoid Z receptor beta, a brain-specific nuclear orphan receptor." *Proc Natl Acad Sci USA* 93(19): 10105-10.

Groot, P. H. E., N. J. Pearce, et al. (2005). "Synthetic LXR agonists increase LDL in CETP species." *J. Lipid Res.* 46(10): 2182-2191.

Harrington, L. E., R. D. Hatton, et al. (2005). "Interleukin 17-producing CD4+ effector T cells develop via a lineage distinct from the T helper type 1 and 2 lineages." *Nat Immunol* 6(11): 1123-32.

Haynes, B. F., M. L. Markert, et al. (2000). "The role of the thymus in immune reconstitution in aging, bone marrow transplantation, and HIV-1 infection." *Annu Rev Immunol* 18: 529-60.

He, Y. W., M. L. Deftos, et al. (1998). "RORgamma t, a novel isoform of an orphan receptor, negatively regulates Fas ligand expression and IL-2 production in T cells." *Immunity* 9(6): 797-806.

Heery, D. G., E. Kalkhoven, et al. (1997). "A signature motif in transcriptional co-activators mediates binding to nuclear receptors." *Nature* 387: 733-736.

Hindinger, C., D. R. Hinton, et al. (2006). "Liver X receptor activation decreases the severity of experimental autoimmune encephalomyelitis." *J Neurosci Res* 84(6): 1225-1234.

Hiroi, Y., H.-H. Kim, et al. (2006). "Rapid nongenomic actions of thyroid hormone." *PNAS:* 0601600103.

Hoeve, M. A., N. D. Savage, et al. (2006). "Divergent effects of IL-12 and IL-23 on the production of IL-17 by human T cells." *Eur J Immunol* 36(3): 661-670.

Houck, K. A., K. M. Borchert, et al. (2004). "T0901317 is a dual LXR/FXR agonist." *Mol Genet Metab* 83(1-2): 184-7.

Iannone, M. A., T. G. Consler, et al. (2001). "Multiplexed molecular interactions of nuclear receptors using fluorescent microspheres." *Cytometry* 44(4): 326-37.

Itoh, M., T. Takahashi, et al. (1999). "Thymus and autoimmunity: production of CD25+CD4+ naturally anergic and suppressive T cells as a key function of the thymus in maintaining immunologic self-tolerance." *J Immunol* 162(9): 5317-26.

Ivanov, I. I. and D. R. Littman (2007). "Characterization of naturally occurring Th17 cells."*13th International Congress of Immunology, Rio di Janeiro Brazil* Aug. 21-25, 2007: P0273.

Ivanov, I. I. and D. R. Littman (2007). *Characterization of naturally occurring Th17 cells.* 13th International Congress of Immunology, R10 de Janiero, Brazil.

Ivanov, I. I., B. S. McKenzie, et al. (2006). "The orphan nuclear receptor RORγt directs the differentiation program of proinflammatory IL-17+ T helper cells." *Cell* 126: 1121-1133.

Iwakura, Y. and H. Ishigame (2006). "The IL-23/IL-17 axis in inflammation." *J Clin Invest* 116(5): 1218-22.

Jetten, A. M., S. Kurebayashi, et al. (2001). "The ROR nuclear orphan receptor subfamily: critical regulators of multiple biological processes." *Prog Nucleic Acid Res Mol Biol* 69: 205-47.

Kallen, J., J. M. Schlaeppi, et al. (2004). "Crystal structure of the human RORalpha ligand binding domain in complex with cholesterol sulfate at 2.2 A." *J Biol Chem* 279(14): 14033-8.

Kallen, J. A., J. M. Schlaeppi, et al. (2002). "X-Ray structure of the hRORα LBD at 1.63 A. Structural and functional data that cholesterol or a cholesterol derivative is the natural ligand of RORα." *Structure (Camb)* 10(12): 1697-707.

Kang, H. S., M. Angers, et al. (2007). "Gene expression profiling reveals a regulatory role for ROR{alpha} and ROR{gamma} in Phase I and Phase II Metabolism." *Physiol Genomics.*

Kebir, H., K. Kreymborg, et al. (2007). "Human T(H)17 lymphocytes promote blood-brain barrier disruption and central nervous system inflammation." *Nat. Med.*

Kirkham, B. W., M. N. Lassere, et al. (2006). "Synovial membrane cytokine expression is predictive of joint damage progression in rheumatoid arthritis: a two-year prospective study (the DAMAGE study cohort)." *Arthritis Rheum* 54(4): 1122-31.

Komiyama, Y., S, Nakae, et al. (2006). "IL-17 Plays an Important Role in the Development of Experimental Autoimmune Encephalomyelitis." *J Immunol* 177(1): 566-73.

Korn, T., E. Bettelli, et al. (2007). "IL-21 initiates an alternative pathway to induce proinflammatory T(H)17 cells." *Nature.*

Krueger, G. G., R. G. Langley, et al. (2007). "A human interleukin-12/23 monoclonal antibody for the treatment of psoriasis." *N Engl J Med* 356(6): 580-92.

Kurebayashi, S., E. Ueda, et al. (2000). "Retinoid-related orphan receptor γ (RORγ) is essential for lymphoid organogenesis and controls apoptosis during thymopoiesis." *Proc Natl Acad Sci USA* 97: 10132-10137.

Langrish, C. L., Y. Chen, et al. (2005). "IL-23 drives a pathogenic T cell population that induces autoimmune inflammation." *J Exp Med* 201(2): 233-40.

Laudet, V. (1999). "A unified nomenclature system for the nuclear receptor superfamily." *Cell* 97: 161-163.

Lee, G., F. Elwood, et al. (2002). "T0070907, a selective ligand for peroxisome proliferator-activated receptor gamma, functions as an antagonist of biochemical and cellular activities." *J Biol Chem* 277(22): 19649-57.

Li, Y., M. Choi, et al. (2005). "Structural and biochemical basis for selective repression of the orphan nuclear receptor liver receptor homolog 1 by small heterodimer partner." *Proc Natl Acad Sci USA* 102(27): 9505-10.

Li, Y., M. H. Lambert, et al. (2003). "Activation of nuclear receptors: a perspective from structural genomics." *Structure (Camb)* 11(7): 741-6.

Liang, S. C., X.-Y. Tan, et al. (2006). "Interleukin (IL)-22 and IL-17 are coexpressed by Th17 cells and cooperatively enhance expression of antimicrobial peptides." *J. Exp. Med.* 203(10): 2271-2279.

Littman, D. and G. Eberl (2006). Compositions and Methods for Modulation of RORγt. *World Intellectual Property Organization.*

Lock, C., G. Hermans, et al. (2002). "Gene-microarray analysis of multiple sclerosis lesions yields new targets validated in autoimmune encephalomyelitis." *Nat Med* 8(5): 500-8.

Lockhart, E., A. M. Green, et al. (2006). "IL-17 production Is dominated by {gamma} {delta} T cells rather than CD4 T cells during *Mycobacterium tuberculosis* infection." *J Immunol* 177(7): 4662-9.

Lubberts, E., M. Koenders, et al. (2005). "The role of T cell interleukin-17 in conducting destructive arthritis: lessons from animal models." *Arthritis Res Ther* 7(1): 29-37.

Lubberts, E., M. I. Koenders, et al. (2004). "Treatment with a neutralizing anti-murine interleukin-17 antibody after the onset of collagen-induced arthritis reduces joint inflammation, cartilage destruction, and bone erosion." *Arthritis Rheum* 50(2): 650-9.

Luckow, V. A. and M. D. Summers (1989). "High level expression of nonfused foreign genes with *Autographa californica* nuclear polyhedrosis virus expression vectors." *Virology* 170(1): 31-9.

Lundholt, B. K., K. M. Scudder, et al. (2003). "A simple technique for reducing edge effect in cell-based assays." *J Biomol Screen* 8(5): 566-70.

Mangan, P. R., L. E. Harrington, et al. (2006). "Transforming growth factor-beta induces development of the T(H) 17 lineage." *Nature* 441(7090): 231-4.

Mannon, P. J., I. J. Fuss, et al. (2004). "Anti-interleukin-12 antibody for active Crohn's disease." *N Engl J Med* 351(20): 2069-79.

Matusevicius, D., P. Kivisakk, et al. (1999). "Interleukin-17 mRNA expression in blood and CSF mononuclear cells is augmented in multiple sclerosis." *Mult Scler* 5(2): 101-4.

McKenna, N. J. and B. W. O'Malley (2002). "Combinatorial control of gene expression by nuclear receptors and coregulators." *Cell* 108(4): 465-74.

Medvedev, A., Z. H. Yan, et al. (1996). "Cloning of a cDNA encoding the murine orphan receptor RZR/ROR gamma and characterization of its response element." *Gene* 181 (1-2): 199-206.

Missbach, M., B. Jagher, et al. (1996). "Thiazolidine diones, specific ligands of the nuclear receptor retinoid Z receptor/retinoid acid receptor-related orphan receptor alpha with potent antiarthritic activity." *J Biol Chem* 271(23): 13515-22.

Moore, J. M., S. J. Galicia, et al. (2004). "Quantitative proteomics of the thyroid hormone receptor coregulator interactions." *J Biol Chem* 279(26): 27584-90.

Moraitis, A. N. and V. Giguere (2003). "The corepressor hairless protects RORa orphan nuclear receptor from proteasome-mediated degradation." *J Biol Chem* 278(52): 52511-8.

Murphy, C. A., C. L. Langrish, et al. (2003). "Divergent pro- and anti-inflammatory roles for IL-23 and IL-12 in joint autoimmune inflammation." *J. Exp. Med.* 198(12): 1951-1957.

Nakae, S., A. Nambu, et al. (2003). "Suppression of immune induction of collagen-induced arthritis in IL-17-deficient mice." *J Immunol* 171(11): 6173-7.

Nurieva, R., X. O. Yang, et al. (2007). "Essential autocrine regulation by IL-21 in the generation of inflammatory T cells." *Nature*.

O'Brien, J., I. Wilson, et al. (2000). "Investigation of the Alamar Blue (resazurin) fluorescent dye for the assessment of mammalian cell cytotoxicity." *Eur J Biochem* 267(17): 5421-6.

Papenfuss, T. L., C. J. Rogers, et al. (2004). "Sex differences in experimental autoimmune encephalomyelitis in multiple murine strains." *J Neuroimmunol* 150(1-2): 59-69.

Park, H., Z. Li, et al. (2005). "A distinct lineage of CD4 T cells regulates tissue inflammation by producing interleukin 17." *Nat Immunol* 6(11): 1133-41.

Powrie, F. and H. Uhlig (2004). "Animal models of intestinal inflammation: clues to the pathogenesis of inflammatory bowel disease." *Novartis Found Symp* 263: 164-74; discussion 174-8, 211-8.

Rolak, L. A. (2003). "Multiple sclerosis: it's not the disease you thought it was." *Clin Med Res* 1(1): 57-60.

Rudick, R. A., W. H. Stuart, et al. (2006). "Natalizumab plus interferon beta-1a for relapsing multiple sclerosis." *N Engl J Med* 354(9): 911-23.

Sato, K., A. Suematsu, et al. (2006). "Th17 functions as an osteoclastogenic helper T cell subset that links T cell activation and bone destruction." *J. Exp. Med.* 203(12): 2673-2682.

Savkur, R. S, and T. P. Burris (2004). "The coactivator LXXLL nuclear receptor recognition motif" *J Pept Res* 63(3): 207-12.

Schultz, J. R., H. Tu, et al. (2000). "Role of LXRs in control of lipogenesis." *Genes Dev* 14(22): 2831-8.

Shin, H. C., N. Benbernou, et al. (1999). "Expression of IL-17 in human memory CD45RO+ T lymphocytes and its regulation by protein kinase A pathway." *Cytokine* 11(4): 257-66.

Spahn, T. W., H. Herbst, et al. (2002). "Induction of colitis in mice deficient of Peyer's patches and mesenteric lymph nodes is associated with increased disease severity and formation of colonic lymphoid patches." *Am J Pathol* 161(6): 2273-82.

Stehlin, C., J. M. Wurtz, et al. (2001). "X-ray structure of the orphan nuclear receptor RORbeta ligand-binding domain in the active conformation." *EMBO J.* 20(21): 5822-5831.

Steinman, L. (2005). "Blocking adhesion molecules as therapy for multiple sclerosis: natalizumab." *Nat Rev Drug Discov* 4(6): 510-8.

Steinman, L. (2007). "A brief history of T(H)17, the first major revision in the T(H)1/T(H)2 hypothesis of T cell-mediated tissue damage." *Nat Med* 13(2): 139-45.

Stumhofer, J. S., A. Laurence, et al. (2006). "Interleukin 27 negatively regulates the development of interleukin 17-producing T helper cells during chronic inflammation of the central nervous system." *Nat Immunol* 7(9): 937-945.

Sun, Z., D. Unutmaz, et al. (2000). "Requirement for RORγ in thymocyte survival and lymphoid organ development." *Science* 288: 2369-2373.

Svensson, S., T. Ostberg, et al. (2003). "Crystal structure of the heterodimeric complex of LXR{alpha} and RXR{beta} ligand-binding domains in a fully agonistic conformation." *EMBO J.* 22(18): 4625-4633.

Thacher, S. M., J. Vasudevan, et al. (2000). "Therapeutic applications for ligands of retinoid receptors." *Current Pharmaceutical Design* 6: 25-58.

Vaknin-Dembinsky, A., K. Balashov, et al. (2006). "IL-23 Is Increased in Dendritic Cells in Multiple Sclerosis and Down-Regulation of IL-23 by Antisense Oligos Increases Dendritic Cell IL-10 Production." *J Immunol* 176(12): 7768-7774.

Veldhoen, M., R. J. Hocking, et al. (2006). "TGFbeta in the context of an inflammatory cytokine milieu supports de novo differentiation of IL-17-producing T cells." *Immunity* 24(2): 179-89.

Webster, N. J., S. Green, et al. (1988). "The hormone-binding domains of the estrogen and glucocorticoid receptors contain an inducible transcription activation function." *Cell* 54(2): 199-207.

Wiesenberg, I., M. Chiesi, et al. (1998). "Specific activation of the nuclear receptors PPARgamma and RORA by the antidiabetic thiazolidinedione BRL 49653 and the antiarthritic thiazolidinedione derivative CGP 52608." *Mol Pharmacol* 53(6): 1131-8.

Wilson, N. J., K. Boniface, et al. (2007). "Development, cytokine profile and function of human interleukin 17-producing helper T cells." *Nat. Immunol.*

Wu, Y., W. W. Chin, et al. (2002). "Ligand and coactivator identity determines the requirement of the charge clamp for coactivation of the peroxisome proliferator-activated receptor gamma." *J. Biol. Chem.* 278(10): 8637-8644.

Xu, H. E., T. B. Stanley, et al. (2002). "Structural basis for antagonist-mediated recruitment of nuclear co-repressors by PPARalpha." *Nature* 415(6873): 813-7.

Yao, Z., S. L. Painter, et al. (1995). "Human IL-17: a novel cytokine derived from T cells." *J Immunol* 155(12): 5483-6.

Yen, D., J. Cheung, et al. (2006). "IL-23 is essential for T cell-mediated colitis and promotes inflammation via IL-17 and IL-6." *J Clin Invest* 116(5): 1310-6.

Zavacki, A. M., J. M. Lehmann, et al. (1997). "Activation of the orphan receptor RIP14 by retinoids." *Proc Natl Acad Sci USA* 94(15): 7909-14.

Zelcer, N. and P. Tontonoz (2006). "Liver X receptors as integrators of metabolic and inflammatory signaling." *J. Clin. Invest.* 116(3): 607-614.

Zhang, G. X., B. Gran, et al. (2003). "Induction of experimental autoimmune encephalomyelitis in IL-12 receptor-beta 2-deficient mice: IL-12 responsiveness is not required in the pathogenesis of inflammatory demyelination in the central nervous system." *J Immunol* 170(4): 2153-60.

Zhang, N., J. Guo, et al. (2003). "Lymphocyte accumulation in the spleen of retinoic acid receptor-related orphan receptor gamma-deficient mice." *J Immunol* 171(4): 1667-75.

Zhang, Z., M. Zheng, et al. (2006). "Critical role of IL-17 receptor signaling in acute TNBS-induced colitis." *Inflamm Bowel Dis* 12(5): 382-388.

Zheng, Y., D. M. Danilenko, et al. (2007). "Interleukin-22, a TH17 cytokine, mediates IL-23-induced dermal inflammation and acanthosis." *Nature* 445(7128): 648-51.

Zhou, L., Ivanov, II, et al. (2007). "IL-6 programs T(H)-17 cell differentiation by promoting sequential engagement of the IL-21 and IL-23 pathways." *Nat. Immunol.*

Zubkova, I., H. Mostowski, et al. (2005). "Up-regulation of IL-7, stromal-derived factor-1 {alpha}, thymus-expressed chemokine, and secondary lymphoid tissue chemokine gene expression in the stromal cells in response to thymocyte depletion: implication for thymus reconstitution." *J Immunol* 175(4): 2321-30.

What is claimed is:

1. A method of inhibiting $T_H$-17 cell differentiation, function or activity in an individual afflicted with multiple sclerosis, psoriasis, Crohn's disease, asthma, rheumatoid arthritis, uveitis or psoriatic arthritis, comprising delivering to said individual an effective amount of a small organic molecule antagonist of RORγ such that said antagonist contacts cells of said individual in vivo, wherein said small organic molecule antagonist has a molecular weight of less than about 600 daltons, wherein said small organic molecule to be delivered has the ability to inhibit transcription from a Gal4 construct comprising a human RORγ ligand binding domain in a Chinese hamster ovary host cell, wherein its potency of inhibition of the transcription, measured as $EC_{50}$, is less than that of T0901317, and wherein said small organic molecule antagonist of RORγ is not T0901317.

2. The method of claim 1, wherein said $T_H$-17 cell function or activity is release of a cytokine.

3. The method of claim 2, wherein said cytokine is interleukin-17 or interleukin-22.

4. The method of claim 1, wherein the RORγ antagonist is orally administered.

5. The method of claim 1 wherein the RORγ antagonist is locally administered.

6. The method of claim 1 wherein said effective amount of a RORγ antagonist is administered on a daily basis without resulting in weight loss or hypertriglyceridemia.

7. A method of treating multiple sclerosis, psoriasis, Crohn's disease, asthma, rheumatoid arthritis, uveitis or psoriatic arthritis, in an individual, comprising identifying an individual in need of such treatment, and delivering to said individual an effective amount of a small organic molecule antagonist of RORγ such that said antagonist contacts cells of said individual in vivo, wherein said small organic molecule antagonist has a molecular weight of less than about 600 daltons, wherein said small organic molecule to be delivered has the ability to inhibit transcription from a Gal4 construct comprising a human RORγ ligand binding domain in a Chinese hamster ovary host, wherein its potency of inhibition of the transcription, measured as $EC_{50}$, is less than that of T0901317, and wherein said small organic molecule antagonist of RORγ is not T0901317.

8. The method of claim 7, wherein the RORγ antagonist is orally administered.

9. The method of claim 7, wherein said RORγ antagonist is locally administered.

10. The method of claim 7, wherein said effective amount of RORγ antagonist is administered on a daily basis without resulting in weight loss or hypertriglyceridemia.

11. The method of claim 1, wherein said RORγ antagonist does not activate an unrelated nuclear receptor selected from the group consisting of human FXR, human PPAR-α, human PPAR-δ, human PPAR-γ, mouse GR, human AR, mouse LXR-α, human RARα or human PR, wherein said RORγ antagonist has an EC50 at said unrelated nuclear receptor as determined by induction of transcription from a Gal4 construct comprising a nuclear receptor binding domain of said unrelated nuclear receptor in said Chinese hamster ovary host cell that is greater than the $EC_{50}$ of said antagonist at human RORγ.

12. The method of claim 7, wherein said RORγ antagonist does not activate an unrelated nuclear receptor selected from the group consisting of human FXR, human PPAR-α, human PPAR-δ, human PPAR-γ, mouse GR, human AR, mouse LXR-α, human RARα or human PR, wherein said RORγ antagonist has an EC50 at said unrelated nuclear receptor as determined by induction of transcription from a Gal4 construct comprising a nuclear receptor binding domain of said unrelated nuclear receptor in said Chinese hamster ovary host cell that is greater than the $EC_{50}$ of said antagonist at human RORγ.

13. The method of claim 1, wherein the potency of inhibition of said RORγ antagonist is at least that of OR-1050.

14. The method of claim 1, wherein the potency of inhibition of said RORγ antagonist is at least that of OR-2161.

15. The method of claim 1, wherein the potency of inhibition of said RORγ antagonist is at least that of OR-13571.

16. The method of claim 4, wherein said RORγ antagonist is administered in a dosage form selected from the group consisting of a tablet, pill, dragee, capsule, liquid, gel, slurry and suspension.

17. The method of claim 1, wherein said RORγ antagonist is topically administered.

18. The method of claim 17, wherein said RORγ antagonist is administered in a dosage form selected from an ointment, gel, cream, paste, salve, gel, cream, lotion and transdermal patch.

19. The method of claim 1, wherein said RORγ antagonist is administered by inhalation.

20. The method of claim 1, wherein said RORγ antagonist is administered as an aerosol spray.

21. The method of claim 7, wherein the potency of inhibition of said RORγ antagonist is at least that of OR-1050.

22. The method of claim 7, wherein the potency of inhibition of said RORγ antagonist is at least that of OR-2161.

23. The method of claim 7, wherein the potency of inhibition of said RORγ antagonist is at least that of OR-13571.

24. The method of claim 8, wherein said RORγ antagonist is administered in a dosage form selected from the group consisting of a tablet, pill, dragee, capsule, liquid, gel, slurry and suspension.

25. The method of claim 7, wherein said RORγ antagonist is topically administered.

26. The method of claim 25, wherein said RORγ antagonist is administered in a dosage form selected from an ointment, gel, cream, paste, salve, gel, cream, lotion and transdermal patch.

27. The method of claim 7, wherein said RORγ antagonist is administered by inhalation.

28. The method of claim 27, wherein said RORγ antagonist is administered as an aerosol spray.

* * * * *